US010369122B2

(12) United States Patent
Dong et al.

(10) Patent No.: US 10,369,122 B2
(45) Date of Patent: Aug. 6, 2019

(54) BENZENE-1,3,5-TRICARBOXAMIDE DERIVATIVES AND USES THEREOF

(71) Applicant: OHIO STATE INNOVATION FOUNDATION, Columbus, OH (US)

(72) Inventors: Yizhou Dong, Dublin, OH (US); Bin Li, Columbus, OH (US)

(73) Assignee: Ohio State Innovation Foundation, Columbus, OH (US)

( * ) Notice: Subject to any disclaimer, the term of this patent is extended or adjusted under 35 U.S.C. 154(b) by 0 days.

(21) Appl. No.: 15/575,919

(22) PCT Filed: May 20, 2016

(86) PCT No.: PCT/US2016/033514
§ 371 (c)(1),
(2) Date: Nov. 21, 2017

(87) PCT Pub. No.: WO2016/187531
PCT Pub. Date: Nov. 24, 2016

(65) Prior Publication Data
US 2018/0147166 A1 May 31, 2018

Related U.S. Application Data

(60) Provisional application No. 62/164,891, filed on May 21, 2015.

(51) Int. Cl.
*A61K 31/166* (2006.01)
*A61K 31/713* (2006.01)
*A61K 9/127* (2006.01)
*A61K 9/51* (2006.01)
*A61K 47/06* (2006.01)

(52) U.S. Cl.
CPC ............ *A61K 31/166* (2013.01); *A61K 9/127* (2013.01); *A61K 9/1272* (2013.01); *A61K 9/5123* (2013.01); *A61K 31/713* (2013.01); *A61K 47/06* (2013.01)

(58) Field of Classification Search
None
See application file for complete search history.

(56) References Cited

U.S. PATENT DOCUMENTS

2013/0158021 A1  6/2013  Dong et al.

FOREIGN PATENT DOCUMENTS

| CN | 1379053 A | 11/2002 | |
|---|---|---|---|
| EP | 0115771 a2 | 8/1984 | |
| EP | 076840 * | 3/1997 | ........... C07C 219/06 |
| WO | 00/55111 A2 | 9/2000 | |
| WO | 2006001835 | 1/2006 | |

OTHER PUBLICATIONS

Muth, Aaron. Polyamine Transport Inhibitors: Design, Syntesis, and Combination Therapies with Difluoromethylornithine. Journal of Medicinal Chemistry, 57, 348-363, 2014.*

Vasylyev, Maxym. Inorganic—organic hybrid materials based on keggin type polyoxometalates and organic polyammonium cations. Journal of Molecular Structure. 656 (2003) 27-35.*
Akins A, et al. (2008) "A combinatorial library of lipid-like materials for delivery of RNAi therapeutics", Nat Biotech. 26(5):561-9.
Altschul et al. (1990) "Basic Local Alignment Search Tool", J. Mol. Biol. 215:403-410.
Altschul et al. (1997) "Gapped BLAST and PSI-BLAST: a new generation of protein database search programs", Nuc. Acids Res. 25:3389-3402.
Andries, O. et. al. (2015) "Synthetic biology devices and circuits for RNA-based "smart vaccines": a propositional review", Expert Rev. Vaccines 14:313-331.
Barzel, A. et. al. (2015) "Promoterless gene targeting without nucleases ameliorates haemophilia B in mice", Nature 517:360-364.
Beaucage et al. (1981) "Deoxynucleoside phosphoramidites—a new class of key intermediates for deoxypolynucleotide synthesis", Tetrahedron Lett., 22:1859-1862.
Boshart et al, (1985) "A very strong enhancer is located upstream of an Immediate early gene of human cytomegalovirus", Cell, 41:521-530.
Broaders, K. E. et. al. (2011) "Acid-degradable solid-walled microcapsules for pH-responsive burst-release drug delivery", Chem. Commun. (Cambridge, U. K.), 47:665-667.
Burnett et al. (2011) "Current progress of siRNA/shRNA therapeutics in clinical trials", Biotechnol J. 6(9):1130-46.
Castanotto, D. et al. (2009) "The promises and pitfalls of RNA-interference-based therapeutics" Nature 457(7228):426-33.
Chen S, et al. (2015) "Genome-wide CRISPR screen in a mouse model of tumor growth and metastasis", Cell. 160(6):1246-60.
Chen, D. et. al. (2012) "Rapid Discovery of Potent siRNA-Containing Lipid Nanoparticles Enabled by Controlled Microfluidic Formulation", J. Am. Chem. Soc. 134:6948-6951.
Chen, Y. et al. (2008) Tumor-targeted delivery of siRNA by non-viral vector: safe and effective cancer therapy. Expert Opin Drug Deliv. 5(12):1301-11.
Cheng, C. et. al. (2012) "Multifunctional triblock copolymers for intracellular messenger RNA delivery", Biomaterials 2012, 33:6868-6876.
Coelho, T., (1996) "Familial amyloid polyneuropathy: new developments in genetics and treatment", Curr Opin Neurol, 9(5):355-9.
Coppola, A. et. al. (2010) "Treatment of hemophilia: a review of current advances and ongoing issues", J. Blood med. 1:183-195.
Cui, et. al. (2007) "Investigation on Process Parameters of Electrospinning System through Orthogonal Experimental Design", J. Appl. Polym. Sci. 103:3105-3112.
Dahlman et al. (2014) "In vivo endothelial siRNA delivery using polymeric nanoparticles with low molecular weight", Nat Nanotechnol. 9(8):648-55.
Damian et al. (2013) "A Crisper Look at Genome Editing: RNA-guided Genome Modification", Mol Ther. 21 (4):720-2.

(Continued)

*Primary Examiner* — Samantha L Shterengarts
(74) *Attorney, Agent, or Firm* — Meunier Carlin & Curfman LLC

(57) ABSTRACT

The present invention relates to compounds, compositions, lipid-like nanoparticles, and methods for delivery of therapeutic, diagnostic, or prophylactic agents (for example, a polynucleotide).

21 Claims, 12 Drawing Sheets

(56) References Cited

OTHER PUBLICATIONS

Davis, M. E., (2009) "The first targeted delivery of siRNA in humans via a self-assembling, cyclodextrin polymer-based nanoparticle: from concept to clinic" Mol Pharm, 6(3):659-68.
Day, et. al. (2004) "Murine thrombosis models", Thromb. Haemostasis 92:486-494.
Dong, et al. (2014) "Lipopeptide nanoparticles for potent and selective siRNA delivery in rodents and nonhuman primates", PNAS USA, 111 (11):3955-60.
Fenske, et al. (2009) "Liposomal nanomedicines", Expert Opin Drug Deliv, 2008. 5(1):25-44.
Fire, A., et al., (1998) Potent and specific genetic interference by double-stranded RNA in Caenorhabditis elegans. Nature, 391(6669):806-11.
Frank-Kamenetsky, M., et al., "Therapeutic RNAi targeting PCSK9 acutely lowers plasma cholesterol in rodents and LDL cholesterol in nonhuman primates", Proc Natl Acad Sci USA, 2008. 105(33):11915-20.
Geall, A. J. et. al. "Nonviral delivery of self-amplifying RNA vaccines", Proc. Natl. Acad. Sci. U. S. A. 2012, 109:14604-14609.
Henikoff and Henikoff (1989) "Amino acid substitution matrices from protein blocks", Proc. Natl. Acad. Sci. USA 89:10915-10919.
Hsu, P.D. et al. (2013) "DNA targeting specificity of RNA-guided Cas9 nucleases", Nat Biotechnol. 31 (9):827-32.
Juliano, R., et al. (2009) "Biological barriers to therapy with antisense and siRNA oligonucleotides", Mol Pharm, 2009. 6(3):686-95.
Karlin, S. et al. (1993) "Applications and statistics for multiple high-scoring segments in molecular sequences", Proc. Natl. Acad. Sci. USA 90:5873-5787.
Kim, H. et al. (2014) "A guide to genome engineering with programmable nucleases", Nat Rev Genet. 2014;15(5):321-34.
Leachman, S. A., et al. (2008), "Therapeutic siRNAs for dominant genetic skin disorders including pachyonychia congenita", J Dermatol Sci, 51(3): 151-7.
Liu, L. et. al. (2013) Abstract of "Optimal Activation of Carboxyl-Superparamagnetic Iron Oxide Nanoparticles Bioconjugated with Antibody Using Orthogonal Array Design", J. Nanosci. Nanotechnol. 13:8137-8143.
Love, T. et. al. (2010) "Lipid-like materials for low-dose, in vivo gene silencing", Proc. Natl. Acad. Sci. U. S. A. 107:1864-1869.
Lv, H. et. al. (2006) "Toxicity of cationic lipids and cationic polymers in gene delivery", J. Controlled Release 114:100-109.
Mali P, et al. (2013) "Cas9 as a versatile tool for engineering biology", Nat Methods. 10(10):957-63.
Mali P, et al. (2013), "RNA-Guided Human Genome Engineering via Cas9", Science. 339(6121):823-6.
Marks, J. R. et. al. (2011) "Spontaneous Membrane-Translocating Peptides by Orthogonal High-Throughput Screening", J. Am. Chem. Soc. 133:8995-9004.
Matsuura, K. et al. (2005) "Artificial Peptide-Nanospheres Self-Assembled from Three-Way Junctions of β-Sheet-Forming Peptides", J. Am. Chem. Soc. 127:10148-10149.
Matteucci, et al. (1981) "Synthesis of Deoxyoligonucleotides on a Polymer Support", J. Am. Chem. Soc., 103:3185-3191.
McClellan, J. et al. (2010) "Genetic heterogeneity in human disease" Cell. 141(2):210-7.
McIvor R.S. (2011) "Therapeutic Delivery of mRNA: The Medium Is the Message", Mol Ther. 19(5):622-3.
Meng, H. N. et. al. (2013) "Orthogonal optimization design for preparation of Fe3O4 nanoparticles via chemical coprecipitation", Appl. Surf. Sci. 280:679-685.
Mishra, S. et. al. (2004) "PEGylation significantly affects cellular uptake and intracellular trafficking of non-viral gene delivery particles", Eur. J. Cell Biol. 83:97-111.
Monahan P.E. et al. (2002) "Hemophilia gene therapy: Update", Current opinion in hematology. 9(5):430-6.

O'Hare K. et al. (1981) "Transformation of mouse fibroblasts to methotrexate resistance by a recombinant plasmid expressing a prokaryotic dihydrofolate reductase", Proc. Natl. Acad. Sci. USA., vol. 78(3):1527-31.
O'Connell M.R. et al. (2014) "Programmable RNA recognition and cleavage by CRISPR/Cas9", Nature. 516(7530):263-6.
Otsuka, H. et. al. (2003) "PEGylated nanoparticles for biological and pharmaceutical Applications", Adv. Drug Delivery Rev. 55:403-419.
Pascolo S. et al. (2008) Vaccination with Messenger RNA 9MRNA) Handb Exp Pharmacol. (183):221-35.
Phua, K. K. et. al. (2013) "Transfection efficiency and transgene expression kinetics of mRNA delivered in naked and nanoparticle format", J. Controlled Release 166:227-233.
Phua, K. K. et. al. (2014) "Messenger RNA (mRNA) nanoparticle tumour Vaccination", Nanoscale 6:7715-7729.
Ran F.A. et al. (2013) "Double Nicking by RNA-Guided CRISPR Cas9 for Enhanced Genome Editing Specificity", Cell. 154(6):1380-9.
Ran F.A. et al. (2015) "In vivo genome editing using *Staphylococcus aureus* Cas9", Nature. 520(7546):186-91.
Rittig, S. M. et. al. (2011) "Intradermal Vaccinations with RNA Coding for TAA Generate CD8+ and CD4+ Immune Responses and Induce Clinical Benefit in Vaccinated Patients", Mol. Ther. 19:990-999.
Ryan, D. et al. (2013) "Rational Design of Orthogonal Libraries of Protein Coding Genes", Acs Synth Biol 2:237-244.
Sabatino D.E. et al. (2012) "Animal models of hemophilia" Progress in molecular biology and translational science. 2012; 105: 151-209.
Sahin, U. et. al. (2014) "mRNA-based therapeutics-developing a new class of drugs", Nat. Rev. Drug Discov 13:759-780.
Sander J.D. et al. (2014) "CRI SPR-Cas systems for editing, regulating and targeting genomes", Nat Bio 32(4):347-55.
Shalem, O. et al. (2014) "Genome-Scale CRISPR-Cas9 Knockout Screening in Human Cells", Science. 343(6166):84-7.
Srivastava, A. et. al. (2013) "WFH Guidelines for the management of hemophilia", Haemophilia 19, e1-47.
Sternberg S.H. et al. (2014) "DNA interrogation by the CRISPR RNA-guided endonuclease Cas9", Nature. 507(7490):62-7.
Su X. et al. (2011) "In Vitro and in Vivo mRNA Delivery Using Lipid-Enveloped pH-Responsive Polymer Nanoparticles", Mol Pharm. 8(3):774-87.
Suwanmanee T. et al. (2014) "Integration-deficient Lentiviral Vectors Expressing Codon-optimized R338L Human FIX Restore Normal Hemostasis in Hemophilia B Mice", Mol Ther. 22(3):567-74.
Takebe Y. et al. (1988) "SR alpha promoter: an efficient and versatile mammalian cDNA expression system composed of the simian virus 40 early promoter and the R-U5 segment of human T-cell leukemia virus type 1 long terminal repeat", Mol. Cell. Biol., vol. 8(1):466-472.
Tan, S. J. et al. (2011) "Engineering Nanocarriers for siRNA Delivery" Small. 7(7):841-56.
Tavernier G. et al. (2011) "mRNA as gene therapeutic: How to control protein expression", J Control Release. 150(3):238-47.
Thiel, K. W. et al. (2009) "Therapeutic Applications of DNA and RNA aptamers", Oligonucleotides 19(3):209-22.
Van Hylckama Vlieg, A. et. al. (2000) "High levels of factor IX increase the risk of venous thrombosis", Blood 95:3678-3682.
Wang, L. et. al. (1997) "A factor IX-deficient mouse model for hemophilia B gene therapy", Proc. Natl. Acad. Sci. U. S. A. 94:11563-11566.
Wang, Y. et. al. (2013) "Systemic Delivery of Modified mRNA Encoding Herpes Simplex Virus 1 Thymidine Kinase for Targeted Cancer Gene Therapy", Mol. Ther. 21:358-367.
Weide, B. et. al. (2008) "Results of the First Phase I/II Clinical Vaccination Trial With Direct Injection of mRNA", J. Immunother. 2008, 31, 180-188.
Weide, B. et. al. (2009) "Direct Injection of Protamine-protected mRNA: Results of a Phase 1/2 Vaccination Trial in Metastatic Melanoma Patients", J. Immunother. 32:498-507.

(56) References Cited

OTHER PUBLICATIONS

Weinstein, S. et al. (2010) "RNAi nanomedicines: challenges and opportunities within the immune system", Nanotechnology 21(23):232001.

Whitehead, K. A. et al. (2009) "Knocking down barriers: advances in siRNA delivery" Nat. Rev. Drug Discovery 8(2):129-138.

Whitehead, K. A. et. al. (2014) "Degradable lipid nanoparticles with predictable in vivo siRNA delivery activity", Nat. commun. 5:4277.

Yin H. et al. (2014) "Genome editing with Cas9 in adult mice corrects a disease mutation and phenotype", Nat Biotechnol. 32(6):551-3.

Zhan, J. Y. et. al. (2011) "Chemical and Biological Assessment of Angelicae Sinensis Radix after Processing with Wine: An Orthogonal Array Design to Reveal the Optimized Conditions", J. Agric. Food Chem. 2011, 59, 6091-6098.

Zhang, Y. et. al. (2013) "Lipid-Modifi ed Aminoglycoside Derivatives for In Vivo siRNA Delivery", Adv. Mater. 25:4641-4645.

Zincarelli, C. et al. (2008) "Analysis of AAV Serotypes 1-9 Mediated Gene Expression and Tropism in Mice After Systemic Injection", Mol Ther. 16(6):1073-80.

Zuris, J.A. et al. (2015) "Cationic lipid-mediated delivery of proteins enables efficient protein-based genome editing in vitro and in vivo", Nat Biotechnol. 33(1):73-80.

International Search Report and Written Opinion issued for International Application No. PCT/US2016/033514, dated Aug. 17, 2016.

International Preliminary Report on Patentability issued for International Application No. PCT/US2016/033514, dated Nov. 30, 2017.

Pubchem CID 49870399 created on Feb. 22, 2011 (Feb. 22, 2011) pp. 1-9. p. 3.

Extended European Search Report and Search Opinion. Issued by the European Patent Office in application No. 16797375.9 dated Jan. 4, 2019. 27 pages.

Zhang, Xue-Qing, et al. "In vitro gene delivery using polyamidoamine dendrimers with a trimesyl core." Biomacromolecules 6.1 (2005): 341-350.

Sun, Shuguang, et al. "Recognition of flexible peptides in water by transition metal complexes." Organic letters 2.7 (2000): 911-914.

* cited by examiner (A)

| LEVELS | FORMULATION COMPONENTS (MOLAR RATIO) | | | |
|---|---|---|---|---|
| | TT3 | DOPE | CHOLESTEROL | DMG-PEG$_{2000}$ |
| 1 | 30 | 1.25 | 18.5 | 0.75 |
| 2 | 40 | 2.50 | 28.5 | 1.5 |
| 3 | 50 | 5.00 | 38.5 | 3 |
| 4 | 60 | 10.00 | 48.5 | 6 |

BENZENE-1,3,5-TRICARBOXAMIDE DERIVATIVES AND USES THEREOF

CROSS-REFERENCE TO RELATED APPLICATIONS

This application is a national stage application filed under 35 U.S.C. of PCT/US2016/033514 filed May 20, 2016, which claims the benefit of U.S. Provisional Patent Application Ser. No. 62/164,891 filed May 21, 2015, the disclosures of which are expressly incorporated herein by reference.

FIELD

The present invention relates to compounds, compositions, lipid-like nanoparticles, and methods for delivery of therapeutic, diagnostic, or prophylactic agents (for example, a polynucleotide).

BACKGROUND

Messenger RNA (mRNA) based therapeutics have shown great promise for expressing functional antibodies and proteins. Clinical studies have explored mRNA for use as vaccines through local administration of naked mRNA or mRNA-transfected dendritic cells in order to induce antigen-specific immune responses. Recently, extensive efforts have been devoted to achieving the systemic delivery of mRNA using liposomes, polymeric nanoparticles, and mRNA-protein complexes. Although significant advances have been made, new mRNA carriers are needed in order to improve delivery efficiency and maximize therapeutic windows of mRNA therapeutics in different human conditions.

Previously, lipid-like nanoparticles (LLNs) have demonstrated efficient delivery of small interfering RNA (siRNA) in rodents and nonhuman primates. siRNA and mRNA possess common physicochemical properties, including components of nucleic acids and negative charges; therefore, LLNs may also serve well as mRNA delivery materials. However, lipid-like nanoparticle (LLN)-assisted mRNA delivery is relatively unexplored and understanding of this system is very limited.

The compounds, compositions, and methods disclosed herein address these and other needs.

SUMMARY

The present invention provides benzene-1,3,5-tricarboxamide derivatives and uses thereof. Also provided are compositions including a compound of the invention and an agent (e.g., an mRNA). The present invention also provides methods and kits using the compositions for delivering an agent to a subject.

In one aspect, the invention provides compounds of Formula I:

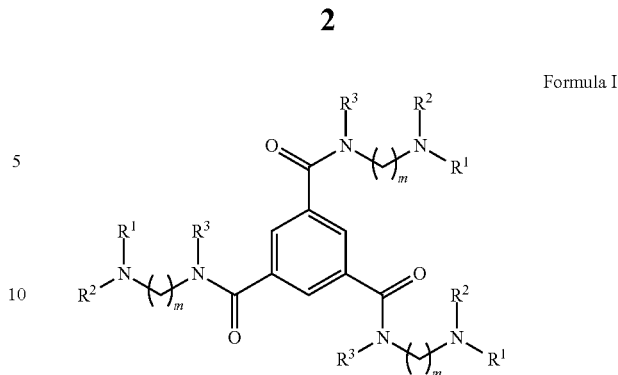

Formula I and salts thereof, wherein $R^1$, $R^2$, $R^3$, and m are as described herein.

In one embodiment, the invention provides compounds of Formula Ia:

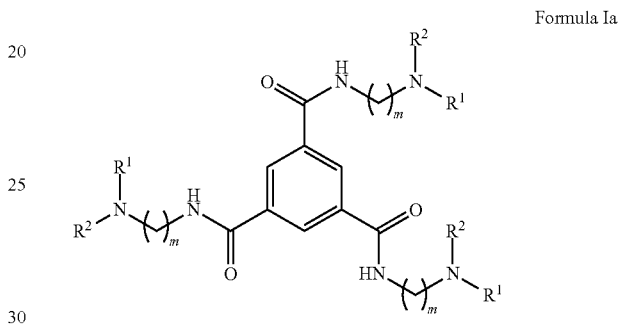

Formula Ia and salts thereof, wherein $R^1$, $R^2$, and m are as described herein.

In one aspect, the invention provides compounds of Formula II:

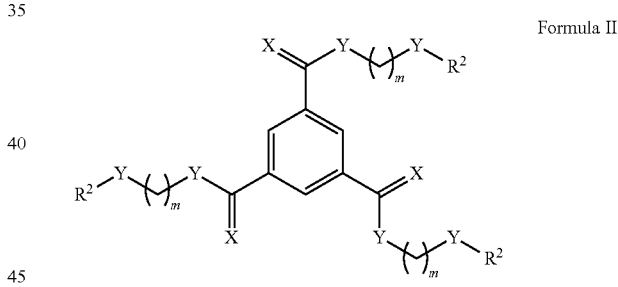

Formula II and salts thereof, wherein $R^2$, Y, and m are as described herein.

In one aspect, the invention provides compounds of Formula III.

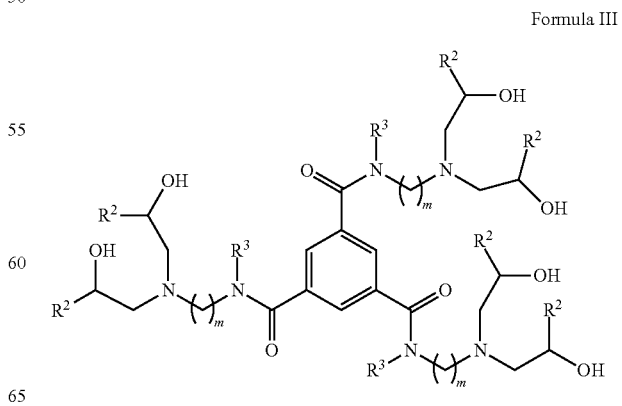

Formula III and salts thereof, wherein $R^2$, $R^3$, and in are as described herein.

In one aspect, the invention provides compounds of Formula IV:

Formula IV

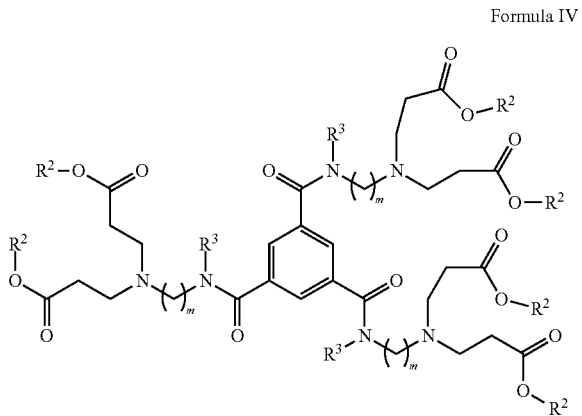

and salts thereof, wherein $R^2$, $R^3$, and m are as described herein.

In one aspect, the invention provides compounds of Formula V:

Formula V

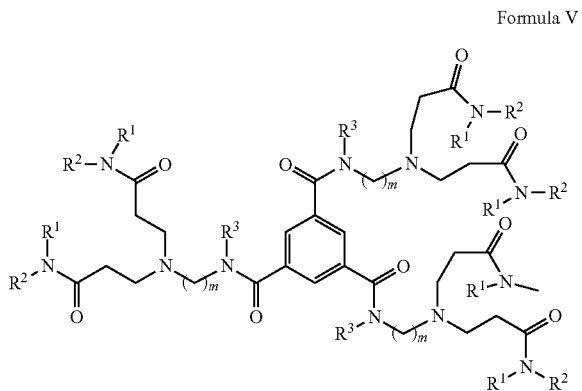

and salts thereof, wherein $R^1$, $R^2$, $R^3$, and m are as described herein.

In one embodiment, the compound is:

Compound TT3

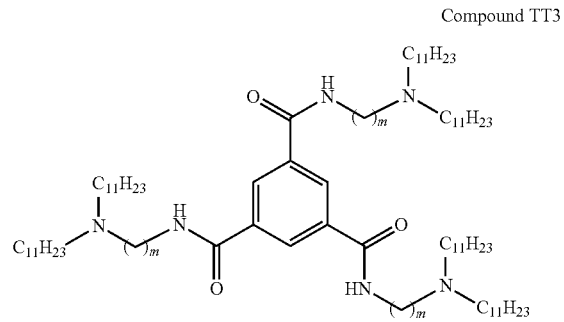

and salts thereof, wherein m=3.

In one aspect, the invention provides a nanoparticle comprising:
a compound of Formula I, II, III, IV, or V;
a non-cationic lipid;
a polyethylene glycol-lipid; and
a sterol.

In one embodiment, the invention provides a nanoparticle comprising:
a compound of Formula I, II, III, IV, or V;
1,2-dioleoyl-sn-glycero-3-phosphoethanolamine (DOPE);
1,2-dimyristoyl-sn-glycerol, methoxypolyethylene glycol (DMG-PEG$_{2000}$); and
a cholesterol.

In one aspect, provided herein is a method for the delivery of an agent (for example, a polynucleotide) into a cell comprising;
introducing into the cell a composition comprising;
i) a nanoparticle, comprising;
 a compound of Formula I, II, III, IV, or V;
 a non-cationic lipid;
 a polyethylene glycol-lipid;
 a sterol; and
ii) an agent.

In some embodiments, the agent is a therapeutic agent, diagnostic agent, or prophylactic agent. In some embodiments, the agent is a polynucleotide (for example, and mRNA).

In some embodiments, provided herein are methods for the delivery of polynucleotides. In some embodiments, provided herein are methods for the delivery of polynucleotides (for example, mRNA) to correct a mutation in a genome. For example, mRNAs can be delivered to correct mutations that cause hemophilia (due to mutations in the genes encoding Factor VIII (F8; hemophilia A) or Factor IX (F9; hemoglobin B).

BRIEF DESCRIPTION OF THE DRAWINGS

The accompanying figures, which are incorporated in and constitute a part of this specification, illustrate several aspects described below.

DETAILED DESCRIPTION OF THE INVENTION

Figure 1:
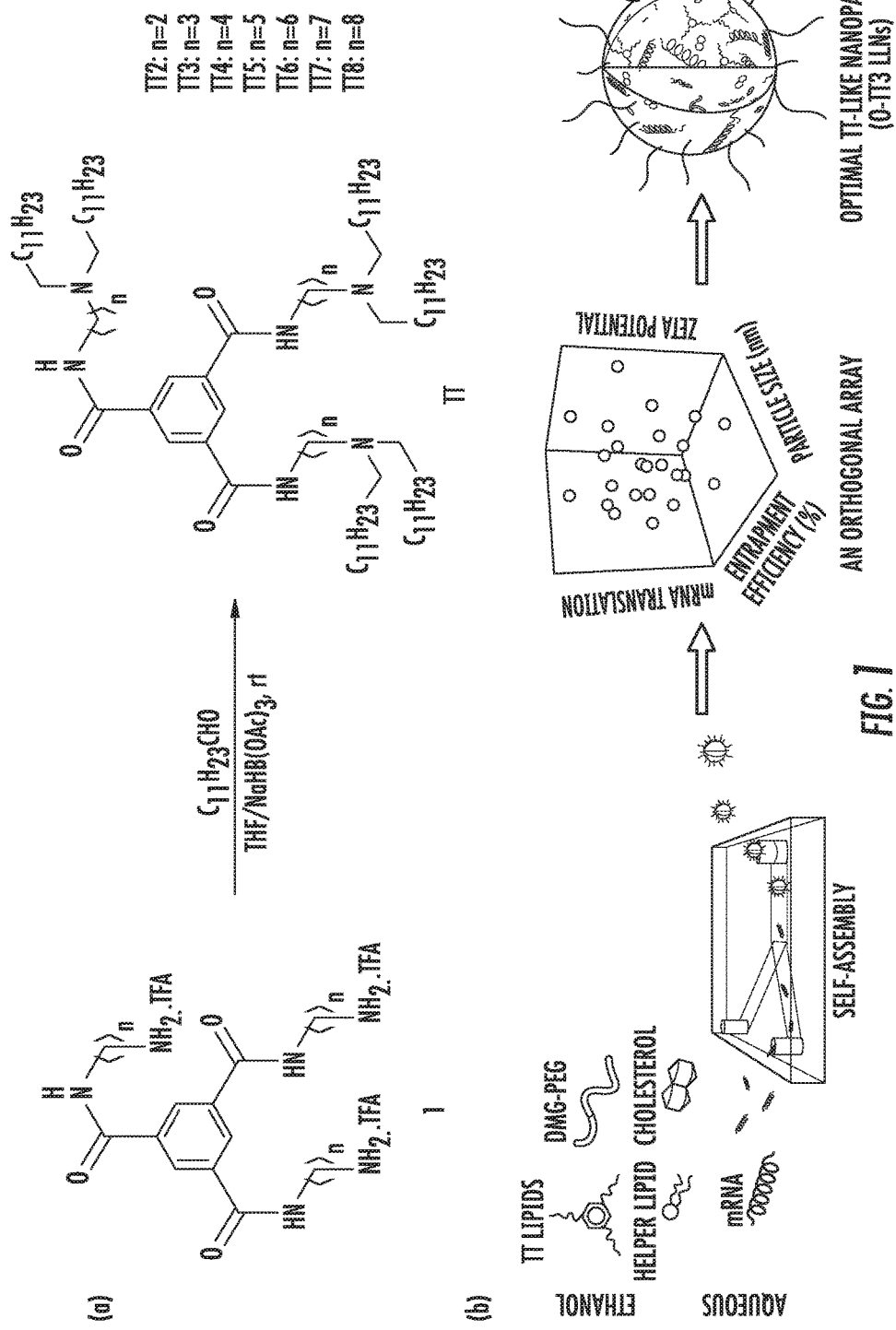
FIG. 1. Schematic for development of $N^1,N^3,N^5$-tris(2-aminoethyl)benzene-1,3,5-tricarboxamide lipid-like nanoparticles. (a) A synthetic route to $N^1,N^3,N^5$-tris(2-aminoethyl)benzene-1,3,5-tricarboxamide derivatives (TT2-TT8). Compound 1 underwent a reductive amination in order to afford desired products TT2-TT8. (b) Illustration of material development for mRNA delivery. TT2-TT8 were formulated with helper lipids, cholesterol (Chol), DMG-PEG$_{2000}$, and mRNA to form TT2-TT8 LLNs via pipetting for in vitro studies or using Precision NanoSystems for in vivo studies.

The present invention provides benzene-1,3,5-tricarboxamide derivatives and uses thereof. Also provided are compositions including a compound of the invention and an agent (e.g., an mRNA). The present invention also provides methods and kits using the compositions for delivering an agent to a subject.

Reference will now be made in detail to the embodiments of the invention, examples of which are illustrated in the drawings and the examples. This invention may, however, be embodied in many different forms and should not be construed as limited to the embodiments set forth herein.

Unless defined otherwise, all technical and scientific terms used herein have the same meaning as commonly understood to one of ordinary skill in the art to which this invention belongs. The following definitions are provided for the full understanding of terms used in this specification.

Terminology

As used herein, the article "a," "an," and "the" means "at least one," unless the context in which the article is used clearly indicates otherwise.

The term "nucleic acid" as used herein means a polymer composed of nucleotides, e.g. deoxyribonucleotides or ribonucleotides.

The terms "ribonucleic acid" and "RNA" as used herein mean a polymer composed of ribonucleotides.

The terms "deoxyribonucleic acid" and "DNA" as used herein mean a polymer composed of deoxyribonucleotides.

The term "oligonucleotide" denotes single- or double-stranded nucleotide multimers of from about 2 to up to about 100 nucleotides in length. Suitable oligonucleotides may be prepared by the phosphoramidite method described by Beaucage and Carruthers, *Tetrahedron Lett.*, 22:1859-1862 (1981), or by the triester method according to Matteucci, et al., *J. Am. Chem. Soc.*, 103:3185 (1981), both incorporated herein by reference, or by other chemical methods using either a commercial automated oligonucleotide synthesizer or VLSIPS™ technology. When oligonucleotides are referred to as "double-stranded," it is understood by those of skill in the art that a pair of oligonucleotides exist in a hydrogen-bonded, helical array typically associated with, for example, DNA. In addition to the 100% complementary form of double-stranded oligonucleotides, the term "double-stranded," as used herein is also meant to refer to those forms which include such structural features as bulges and loops, described more fully in such biochemistry texts as Shyer, *Biochemistry*, Third Ed., (1988), incorporated herein by reference for all purposes.

The term "polynucleotide" refers to a single or double stranded polymer composed of nucleotide monomers. In some embodiments, the polynucleotide is composed of nucleotide monomers of generally greater than 100 nucleotides in length and up to about 8,000 or more nucleotides in length.

The term "polypeptide" refers to a compound made up of a single chain of D- or L-amino acids or a mixture of D- and L-amino acids joined by peptide bonds.

The term "complementary" refers to the topological compatibility or matching together of interacting surfaces of a probe molecule and its target. Thus, the target and its probe can be described as complementary, and furthermore, the contact surface characteristics are complementary to each other.

The term "hybridization" refers to a process of establishing a non-covalent, sequence-specific interaction between two or more complementary strands of nucleic acids into a single hybrid, which in the case of two strands is referred to as a duplex.

The term "anneal" refers to the process by which a single-stranded nucleic acid sequence pairs by hydrogen bonds to a complementary sequence, forming a double-stranded nucleic acid sequence, including the reformation (renaturation) of complementary strands that were separated by heat (thermally denatured).

The term "melting" refers to the denaturation of a double-stranded nucleic acid sequence due to high temperatures, resulting in the separation of the double strand into two single strands by breaking the hydrogen bonds between the strands.

The term "target" refers to a molecule that has an affinity for a given probe. Targets may be naturally-occurring or man-made molecules. Also, they can be employed in their unaltered state or as aggregates with other species.

The term "promoter" or "regulatory element" refers to a region or sequence determinants located upstream or downstream from the start of transcription and which are involved in recognition and binding of RNA polymerase and other proteins to initiate transcription. Promoters need not be of bacterial origin, for example, promoters derived from viruses or from other organisms can be used in the compositions, systems, or methods described herein. The term "regulatory element" is intended to include promoters, enhancers, internal ribosomal entry sites (IRES), and other expression control elements (e.g. transcription termination signals, such as polyadenylation signals and poly-U sequences). Such regulatory elements are described, for example, in Goeddel, Gene Expression Technology: Methods in Enzymology 185, Academic Press, San Diego, Calif. (1990). Regulatory elements include those that direct constitutive expression of a nucleotide sequence in many types of host cell and those that direct expression of the nucleotide sequence only in certain host cells (e.g., tissue-specific regulatory sequences). A tissue-specific promoter may direct expression primarily in a desired tissue of interest, such as muscle, neuron, bone, skin, blood, specific organs (e.g. liver, pancreas), or particular cell types (e.g. lymphocytes). Regulatory elements may also direct expression in a temporal-dependent manner, such as in a cell-cycle dependent or developmental stage-dependent manner, which may or may not also be tissue or cell-type specific. In some embodiments, a vector comprises one or more pol III promoter (e.g. 1, 2, 3, 4, 5, or more pol I promoters), one or more pol II promoters (e.g. 1, 2, 3, 4, 5, or more pol II promoters), one or more pol I promoters (e.g. 1, 2, 3, 4, 5, or more pol I promoters), or combinations thereof. Examples of pol III promoters include, but are not limited to, U6 and H1 promoters. Examples of pol II promoters include, but are not limited to, the retroviral Rous sarcoma virus (RSV) LTR promoter (optionally with the RSV enhancer), the cytomegalovirus (CMV) promoter (optionally with the CMV enhancer) [see, e.g., Boshart et al, Cell, 41:521-530 (1985)], the SV40 promoter, the dihydrofolate reductase promoter, the β-actin promoter, the phosphoglycerol kinase (PGK) promoter, and the EF1α promoter. Also encompassed by the term "regulatory element" are enhancer elements, such as WPRE; CMV enhancers; the R-U5' segment in LTR of HTLV-I (Mol. Cell. Biol., Vol. 8(1), p. 466-472, 1988); SV40 enhancer; and the intron sequence between exons 2 and 3 of rabbit β-globin (Proc. Natl. Acad. Sci. USA., Vol. 78(3), p. 1527-31, 1981). It is appreciated by those skilled in the art that the design of the expression vector can depend on such factors as the choice of the host cell to be transformed, the level of expression desired, etc.

The term "recombinant" refers to a human manipulated nucleic acid (e.g. polynucleotide) or a copy or complement of a human manipulated nucleic acid (e.g. polynucleotide), or if in reference to a protein (i.e., a "recombinant protein"), a protein encoded by a recombinant nucleic acid (e.g. polynucleotide). In embodiments, a recombinant expression cassette comprising a promoter operably linked to a second nucleic acid (e.g. polynucleotide) may include a promoter that is heterologous to the second nucleic acid (e.g. polynucleotide) as the result of human manipulation (e.g., by methods described in Sambrook et al., *Molecular Cloning—A Laboratory Manual*, Cold Spring Harbor Laboratory, Cold Spring Harbor, N.Y., (1989) or Current Protocols in Molecular Biology Volumes 1-3, John Wiley & Sons, Inc. (1994-1998)). In another example, a recombinant expression cassette may comprise nucleic acids (e.g. polynucleotides) combined in such a way that the nucleic acids (e.g. polynucleotides) are extremely unlikely to be found in nature. For instance, human manipulated restriction sites or plasmid vector sequences may flank or separate the promoter from the second nucleic acid (e.g. polynucleotide). One of skill will recognize that nucleic acids (e.g. polynucleotides) can be manipulated in many ways and are not limited to the examples above.

The term "expression cassette" refers to a nucleic acid construct, which when introduced into a host cell, results in transcription and/or translation of a RNA or polypeptide, respectively. In embodiments, an expression cassette comprising a promoter operably linked to a second nucleic acid (e.g. polynucleotide) may include a promoter that is heterologous to the second nucleic acid (e.g. polynucleotide) as the result of human manipulation (e.g., by methods described in Sambrook et al., *Molecular Cloning—A Laboratory Manual*, Cold Spring Harbor Laboratory, Cold Spring Harbor, N.Y., (1989) or Current Protocols in Molecular Biology Volumes 1-3, John Wiley & Sons, Inc. (1994-1998)). In some embodiments, an expression cassette comprising a terminator (or termination sequence) operably linked to a second nucleic acid (e.g. polynucleotide) may include a terminator that is heterologous to the second nucleic acid (e.g., polynucleotide) as the result of human manipulation. In some embodiments, the expression cassette comprises a promoter operably linked to a second nucleic acid (e.g. polynucleotide) and a terminator operably linked to the second nucleic acid (e.g. polynucleotide) as the result of human manipulation. In some embodiments, the expression cassette comprises an endogenous promoter. In some embodiments, the expression cassette comprises an endogenous terminator. In some embodiments, the expression cassette comprises a synthetic (or non-natural) promoter. In some embodiments, the expression cassette comprises a synthetic (or non-natural) terminator.

The terms "identical" or percent "identity," in the context of two or more nucleic acids or polypeptide sequences, refer to two or more sequences or subsequences that are the same or have a specified percentage of amino acid residues or nucleotides that are the same (i.e., about 60% identity, preferably 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or higher identity over a specified region when compared and aligned for maximum correspondence over a comparison window or designated region) as measured using a BLAST or BLAST 2.0 sequence comparison algorithms with default parameters described below, or by manual alignment and visual inspection (see, e.g., NOBI web site or the like). Such sequences are then said to be "substantially identical." This definition also refers to, or may be applied to, the compliment of a test sequence. The definition also includes sequences that have deletions and/or additions, as well as those that have substitutions. As described below, the preferred algorithms can account for gaps and the like. Preferably, identity exists over a region that is at least about 10 amino acids or 20 nucleotides in length, or more preferably over a region that is 10-50 amino acids or 20-50 nucleotides in length. As used herein, percent (%) amino acid sequence identity is defined as the percentage of amino acids in a candidate sequence that are identical to the amino acids in a reference sequence, after aligning the sequences and introducing gaps, if necessary, to achieve the maximum percent sequence identity. Alignment for purposes of determining percent sequence identity can be achieved in various ways that are within the skill in the art, for instance, using publicly available computer software such as BLAST, BLAST-2, ALIGN, ALIGN-2 or Megalign (DNASTAR) software. Appropriate parameters for measuring alignment, including any algorithms needed to achieve maximal alignment over the full-length of the sequences being compared can be determined by known methods.

For sequence comparisons, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Preferably, default program parameters can be used, or alternative parameters can be designated. The sequence comparison algorithm then calculates the percent sequence identities for the test sequences relative to the reference sequence, based on the program parameters.

One example of an algorithm that is suitable for determining percent sequence identity and sequence similarity are the BLAST and BLAST 2.0 algorithms, which are described in Altschul et al. (1977) *Nuc. Acids Res.* 25:3389-3402, and Altschul et al. (1990) *J. Mol. Biol.* 215:403-410, respectively. Software for performing BLAST analyses is publicly available through the National Center for Biotechnology Information (http://www.ncbi.nlm.nih.gov/). This algorithm involves first identifying high scoring sequence pairs (HSPS) by identifying short words of length W in the query sequence, which either match or satisfy sonic positive-valued threshold score T when aligned with a word of the same length in a database sequence. T is referred to as the neighborhood word score threshold (Altschul et al. (1990) *J. Mol. Biol.* 215:403-410). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) or 10, M=5, N=−4 and a comparison of both strands. For amino acid sequences, the BLASTP program uses as defaults a wordlength of 3, and expectation (E) of 10, and the BLOSUM62 scoring matrix (see Henikoff and Henikoff (1989) *Proc. Natl. Acad. Sci. USA* 89:10915) alignments (B) of 50, expectation (F) of 10, M=5, N=−4, and a comparison of both strands.

The BLAST algorithm also performs a statistical analysis of the similarity between two sequences (see e.g., Karlin and Altschul (1993) *Proc. Natl. Acad. Sci. USA* 90:5873-5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01.

The phrase "codon optimized" as it refers to genes or coding regions of nucleic acid molecules for the transformation of various hosts, refers to the alteration of codons in the gene or coding regions of polynucleic acid molecules to reflect the typical codon usage of a selected organism without altering the polypeptide encoded by the DNA. Such optimization includes replacing at least one, or more than one, or a significant number, of codons with one or more codons that are more frequently used in the genes of that selected organism.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are near each other, and, in the case of a secretory leader, contiguous and in reading phase. However, operably linked nucleic acids (e.g. enhancers and coding sequences) do not have to be contiguous. Linking is accomplished by ligation at convenient restriction sites. If such sites do not exist, the synthetic oligonucleotide adaptors or linkers are used in accordance with conventional practice. In embodiments, a promoter is operably linked with a coding sequence when it is capable of affecting (e.g. modulating relative to the absence of the promoter) the expression of a protein from that coding sequence (i.e., the coding sequence is under the transcriptional control of the promoter).

The term "nucleobase" refers to the part of a nucleotide that bears the Watson/Crick base-pairing functionality. The most common naturally-occurring nucleobases, adenine (A), guanine (G), uracil (U), cytosine (C), and thymine (T) bear the hydrogen-bonding functionality that binds one nucleic acid strand to another in a sequence specific manner.

As used throughout, by a "subject" (or a "host") meant an individual. Thus, the "subject" can include, for example, domesticated animals, such as cats, dogs, etc., livestock (e.g., cattle, horses, pigs, sheep, goats, etc.), laboratory animals (e.g., mouse, rabbit, rat, guinea pig, etc.) mammals, non-human mammals, primates, non-human primates, rodents, birds, reptiles, amphibians, fish, and any other animal. The subject can be a mammal such as a primate or a human.

Chemical Definitions

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc.

"$Z^1$," "$Z^2$," "$Z^3$," and "$Z^4$" are used herein as generic symbols to represent various specific substituents. These symbols can be any substituent, not limited to those disclosed herein, and when they are defined to be certain substituents in one instance, they can, in another instance, be defined as some other substituents.

The term "aliphatic" as used herein refers to a non-aromatic hydrocarbon group and includes branched and unbranched, alkyl, alkenyl or alkynyl groups.

The term "alkyl" as used herein is a branched or unbranched saturated hydrocarbon group of 1 to 24 carbon atoms, such as methyl, ethyl, n-propyl, isopropyl, n-butyl, isobutyl, t-butyl, pentyl, hexyl, heptyl, octyl, nonyl, decyl, dodecyl, tetradecyl, hexadecyl, eicosyl, tetracosyl, and the like. The alkyl group can also be substituted or unsubstituted. The alkyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol, as described below.

Throughout the specification "alkyl" is generally used to refer to both unsubstituted alkyl groups and substituted alkyl groups; however, substituted alkyl groups are also specifically referred to herein by identifying the specific substituent(s) on the alkyl group. For example, the term "halogenated alkyl" specifically refers to an alkyl group that is substituted with one or more halide, e.g., fluorine, chlorine, bromine, or iodine. The term "alkoxyalkyl" specifically refers to an alkyl group that is substituted with one or more alkoxy groups, as described below. The term "alkylamino" specifically refers to an alkyl group that is substituted with one or more amino groups, as described below, and the like. When "alkyl" is used in one instance and a specific term such as "alkylalcohol" is used in another, it is not meant to imply that the term "alkyl" does not also refer to specific terms such as "alkylalcohol" and the like.

This practice is also used for other groups described herein. That is, while a term such as "cycloalkyl" refers to both unsubstituted and substituted cycloalkyl moieties, the substituted moieties can, in addition, be specifically identified herein; for example, a particular substituted cycloalkyl can be referred to as, e.g., an "alkylcycloalkyl." Similarly, a substituted alkoxy can be specifically referred to as, e.g., a "halogenated alkoxy," a particular substituted alkenyl can be, e.g., an "alkylalcohol," and the like. Again, the practice of using a general term, such as "cycloalkyl," and a specific term, such as "alkylcycloalkyl," is not meant to imply that the general term does not also include the specific term.

The term "alkoxy" as used herein is an alkyl group bound through a single, terminal ether linkage; that is, an "alkoxy" group can be defined as —$OZ^1$ where $Z^1$ is alkyl as defined above.

The term "alkenyl" as used herein is a hydrocarbon group of from 2 to 24 carbon atoms with a structural formula containing at least one carbon-carbon double bond. Asymmetric structures such as $(Z^1Z^2)C=C(Z^3Z^4)$ are intended to include both the and Z isomers. This can be presumed in structural formulae herein wherein an asymmetric alkene is present, or it can be explicitly indicated by the bond symbol C=C. The alkenyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol, as described below.

The term "alkynyl" as used herein is a hydrocarbon group of 2 to 24 carbon atoms with a structural formula containing at least one carbon-carbon triple bond. The alkynyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfa-oxo, sulfonyl, sulfone, sulfoxide, or thiol, as described below.

The term "aryl" as used herein is a group that contains any carbon-based aromatic group including, but not limited to, benzene, naphthalene, phenyl, biphenyl, phenoxybenzene, and the like. The term "heteroaryl" is defined as a group that contains an aromatic group that has at least one heteroatom incorporated within the ring of the aromatic group. Examples of heteroatoms include, but are not limited to, nitrogen, oxygen, sulfur, and phosphorus. The term "non-heteroaryl," which is included in the term "aryl," defines a group that contains an aromatic group that does not contain a heteroatom. The aryl or heteroaryl group can be substituted or unsubstituted. The aryl or heteroaryl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol as described herein. The term "biaryl" is a specific type of aryl group and is included in the definition of aryl. Biaryl refers to two aryl groups that are bound together via a fused ring structure, as in naphthalene, or are attached via one or more carbon-carbon bonds, as in biphenyl.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, etc. The term "heterocycloalkyl" is a cycloalkyl group as defined above where at least one of the carbon atoms of the ring is substituted with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol as described herein.

The term "cycloalkenyl" as used herein is a non-aromatic carbon-based ring composed of at least three carbon atoms and containing at least one double bound, i.e., C=C. Examples of cycloalkenyl groups include, but are not limited to, cyclopropenyl, cyclobutenyl, cyclopentenyl, cyclopentadienyl, cyclohexenyl, cyclohexadienyl, and the like. The term "heterocycloalkenyl" is a type of cycloalkenyl group as defined above, and is included within the meaning of the term "cycloalkenyl," where at least one of the carbon atoms of the ring is substituted with a heteroatom such as, but not limited to, nitrogen, oxygen, sulfur, or phosphorus. The cycloalkenyl group and heterocycloalkenyl group can be substituted or unsubstituted. The cycloalkenyl group and heterocycloalkenyl group can be substituted with one or more groups including, but not limited to, alkyl, alkoxy, alkenyl, alkynyl, aryl, heteroaryl, aldehyde, amino, carboxylic acid, ester, ether, halide, hydroxy, ketone, nitro, silyl, sulfa-oxo, sulfonyl, sulfone, sulfoxide, or thiol as described herein.

The term "cyclic group" is used herein to refer to either aryl groups, non-aryl groups (i.e., cycloalkyl, heterocycloalkyl, cycloalkenyl, and heterocycloalkenyl groups), or both. Cyclic groups have one or more ring systems that can be substituted or unsubstituted. A cyclic group can contain one or more aryl groups, one or more non-aryl groups, or one or more aryl groups and one or more non-aryl groups.

The term "aldehyde" as used herein is represented by the formula —C(O)H. Throughout this specification "C(O)" or "CO" is a short hand notation for C=O.

The terms "amine" or "amino" as used herein are represented by the formula —NZ$^1$Z$^2$, where Z$^1$ and Z$^2$ can each be substitution group as described herein, such as hydrogen, an alkyl, halogenated alkyl, alkenyl, alkynyl, aryl, heteroaryl, cycloalkyl, cycloalkenyl, heterocycloalkyl, or heterocycloalkenyl group described above.

The term "carboxylic acid" as used herein is represented by the formula —C(O)OH. A "carboxylate" or "carboxyl" group as used herein is represented by the formula —C(O)O$^-$.

The term "ester" as used herein is represented by the formula —OC(O)Z$^1$ or —C(O)OZ$^1$, where Z$^1$ can be an alkyl, halogenated alkyl, alkenyl, alkynyl, aryl, heteroaryl, cycloalkyl, cycloalkenyl, heterocycloalkyl, or heterocycloalkenyl group described above.

The term "ether" as used herein is represented by the formula Z$^1$OZ$^2$, where Z$^1$ and Z$^2$ can be, independently, an alkyl, halogenated alkyl, alkenyl, alkynyl, aryl, heteroaryl, cycloalkyl, cycloalkenyl, heterocycloalkyl, or heterocycloalkenyl group described above.

The term "ketone" as used herein is represented by the formula Z$^1$C(O)Z$^2$, where Z$^1$ and Z$^2$ can be, independently, an alkyl, halogenated alkyl, alkenyl, alkynyl, aryl, heteroaryl, cycloalkyl, cycloalkenyl, heterocycloalkyl, or heterocycloalkenyl group described above.

The term "halide" or "halogen" as used herein refers to the fluorine, chlorine, bromine, and iodine.

The term "hydroxyl" as used herein is represented by the formula —OH.

The term "nitro" as used herein is represented by the formula —NO$^2$.

The term "silyl" as used herein is represented by the formula —SiZ$^1$Z$^2$Z$^3$, where Z$^1$, Z$^2$, and Z$^3$ can be, independently, hydrogen, alkyl, halogenated alkyl, alkoxy, alkenyl, alkynyl, aryl, heteroaryl, cycloalkyl, cycloalkenyl, heterocycloalkyl, or heterocycloalkenyl group described above.

The term "sulfonyl" is used herein to refer to the sulfo-oxo group represented by the formula —S(O)$_2$Z$^1$, where Z$^1$ can be hydrogen, an alkyl, halogenated alkyl, alkenyl, alkynyl, aryl, heteroaryl, cycloalkyl, cycloalkenyl, heterocycloalkyl, or heterocycloalkenyl group described above.

The term "sulfonyl amino" or "sulfonamide" as used herein is represented by the formula —S(O)$_2$NH—.

The term "phosphonyl" is used herein to refer to the phospho-oxo group represented by the formula —P(O)(OZ$^1$)$_2$, where Z$^1$ can be hydrogen, an alkyl, halogenated alkyl, alkenyl, alkynyl, aryl, heteroaryl, cycloalkyl, cycloalkenyl, heterocycloalkyl, or heterocycloalkenyl group described above.

The term "thiol" as used herein is represented by the formula —SH.

The term "thio" as used herein is represented by the formula —S—.

"R$^1$," "R$^2$," "R$^3$," "R$^4$," etc., where n is some integer, as used herein can, independently, possess one or more of the groups listed above. For example, if R$^1$ is a straight chain alkyl group, one of the hydrogen atoms of the alkyl group can optionally be substituted with a hydroxyl group, an alkoxyl group, an amine group, an alkyl group, a halide, and the like. Depending upon the groups that are selected, a first group can be incorporated within second group or, alternatively, the first group can be pendant (i.e., attached) to the second group. For example, with the phrase "an alkyl group comprising an amino group," the amino group can be incorporated within the backbone of the alkyl group. Alternatively, the amino group can be attached to the backbone of the alkyl group. The nature of the group(s) that is (are) selected will determine if the first group is embedded or attached to the second group.

Unless stated to the contrary, a formula with chemical bonds shown only as solid lines and not as wedges or dashed lines contemplates each possible isomer, e.g., each enantiomer, diastereomer, and meso compound, and a mixture of isomers, such as a racemic or scalemic mixture.

Reference will now be made in detail to specific aspects of the disclosed materials, compounds, compositions, articles, and methods, examples of which are illustrated in the accompanying Examples and Figures.

Compounds

The present invention provides benzene-1,3,5-tricarboxamide derivatives and uses thereof. Also provided are compositions (e.g., pharmaceutical compositions) including a compound of the invention and an agent (e.g., an siRNA, mRNA, or plasmid DNA). The present invention also provides methods and kits using the compositions for delivering an agent to a subject.

In one aspect, the invention provides compounds of Formula I:

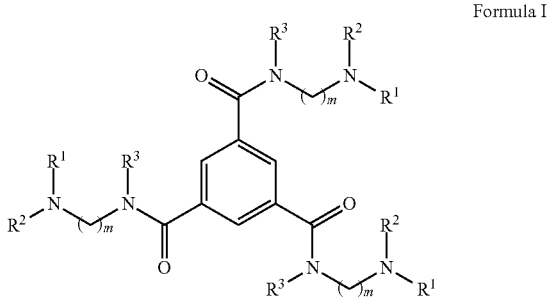

Formula I and salts thereof; wherein
each $R^1$ is independently hydrogen or substituted or unsubstituted alkyl;
each $R^2$ is independently substituted or unsubstituted alkyl;
each $R^3$ is independently hydrogen or substituted or unsubstituted alkyl; and
each m is independently 1, 2, 3, 4, 5, 6, 7, or 8.

In one embodiment, the invention provides compounds of Formula I, wherein:
each $R^1$ is independently substituted or unsubstituted alkyl;
each $R^2$ is independently substituted or unsubstituted alkyl;
each $R^3$ is independently hydrogen or substituted or unsubstituted alkyl; and
each m is independently 1, 2, 3, 4, 5, 6, 7, or 8.

In one embodiment, the invention provides compounds of Formula I, wherein:
each $R^1$ is independently hydrogen or substituted or unsubstituted alkyl;
each $R^2$ is independently substituted or unsubstituted alkyl;
each $R^3$ is independently hydrogen; and
each m is independently 1, 2, 3, 4, 5, 6, 7, or 8.

In one embodiment, the invention provides compounds of Formula I, wherein:
each $R^1$ is independently substituted or unsubstituted alkyl;
each $R^2$ is independently substituted or unsubstituted alkyl;
each $R^3$ is hydrogen; and
each m is independently 1, 2, 3, 4, 5, 6, 7, or 8.

In one embodiment, the invention provides compounds of Formula I, wherein:
each $R^1$ is independently unsubstituted alkyl;
each $R^2$ is independently unsubstituted alkyl;
each $R^3$ is hydrogen; and
each m is independently 1, 2, 3, 4, 5, 6, 7, or 8.

In one embodiment, the invention provides compounds of Formula I, wherein:
each $R^1$ is independently hydrogen or substituted or unsubstituted alkyl,
each $R^2$ is independently substituted or unsubstituted alkyl;
each $R^3$ is independently hydrogen or substituted or unsubstituted alkyl; and
each m is 3.

In one embodiment, the invention provides compounds of Formula I, wherein:
each $R^1$ is independently substituted or unsubstituted alkyl;
each $R^2$ is independently substituted or unsubstituted alkyl;
each $R^3$ is independently hydrogen or substituted or unsubstituted alkyl; and
each m is 3.

In one embodiment, the invention provides compounds of Formula I, wherein:
each $R^1$ is independently hydrogen or substituted or unsubstituted alkyl;
each $R^2$ is independently substituted or unsubstituted alkyl;
each $R^3$ is hydrogen; and
each m is 3.

In one embodiment, the invention provides compounds of Formula I, wherein:
each $R^1$ is independently substituted or unsubstituted alkyl;
each $R^2$ is independently substituted or unsubstituted alkyl;
each $R^3$ is hydrogen; and
each m is 3.

In one embodiment, the invention provides compounds of Formula I, wherein:
each $R^1$ is independently hydrogen or substituted or unsubstituted alkyl;
each $R^2$ is independently substituted or unsubstituted alkyl;
each $R^3$ is independently hydrogen or substituted or unsubstituted alkyl; and
each m is 3.

In one embodiment, the invention provides compounds of Formula I, wherein:
each $R^1$ is independently unsubstituted alkyl;
each $R^2$ is independently unsubstituted alkyl;
each $R^3$ is hydrogen; and
each m is 3.

In one aspect, the invention provides compounds of Formula Ia:

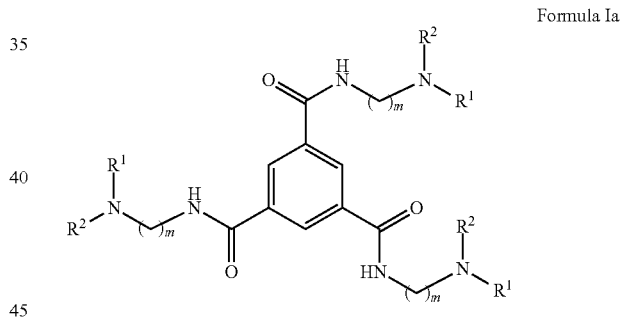

Formula Ia and salts thereof; wherein
each $R^1$ is independently hydrogen or substituted or unsubstituted alkyl;
each $R^2$ is independently substituted or unsubstituted alkyl; and
each m is independently 1, 2, 3, 4, 5, 6, 7, or 8.

In one embodiment, the invention provides compounds of Formula Ia, wherein:
each $R^1$ is independently substituted or unsubstituted alkyl;
each $R^2$ is independently substituted or unsubstituted alkyl; and
each m is independently 1, 2, 3, 4, 5, 6, 7, or 8.

In one embodiment, the invention provides compounds of Formula Ia, wherein:
each $R^1$ is independently unsubstituted alkyl;
each $R^2$ is independently unsubstituted alkyl; and
each m is independently 1, 2, 3, 4, 5, 6, 7, or 8.

In one embodiment, the invention provides compounds of Formula Ia, wherein:
each $R^1$ is independently hydrogen or substituted or unsubstituted alkyl;

each R² is independently substituted or unsubstituted alkyl; and each m is 3.

In one embodiment, the invention provides compounds of Formula Ia, wherein:
each R¹ is independently substituted or unsubstituted alkyl;
each R² is independently substituted or unsubstituted alkyl; and
each m is 3.

In one embodiment, the invention provides compounds of Formula Ia, wherein:
each R¹ is independently unsubstituted alkyl;
each R² is independently unsubstituted alkyl; and
each m is 3.

In one aspect, the invention provides compounds of Formula II:

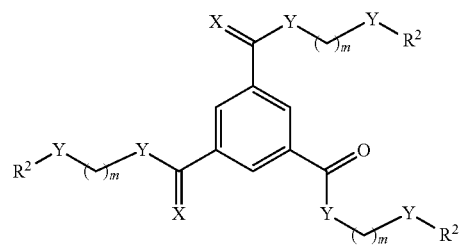

Formula II and salts thereof wherein
each X is independently O, S, or NR¹R²;
each Y is independently O, S, or NR¹;
each R¹ is independently hydrogen or substituted or unsubstituted alkyl,
each R² is independently substituted or unsubstituted alkyl; and
each m is independently 1, 2, 3, 4, 5, 6, 7, or 8.

In one embodiment, the invention provides compounds of Formula II, wherein:
each X is independently O, S, or NR¹R²;
each Y is independently O, S, or NR¹;
each R¹ is independently substituted or unsubstituted alkyl;
each R² is independently substituted or unsubstituted alkyl; and
each m is independently 1, 2, 3, 4, 5, 6, 7, or 8.

In one embodiment, the invention provides compounds of Formula II, wherein:
each X is independently O, S, or NR¹R²;
each Y is independently O, S, or NR¹;
each R¹ is independently unsubstituted alkyl;
each R² is independently unsubstituted alkyl; and
each m is independently 1, 2, 3, 4, 5, 6, 7, or 8.

In one embodiment, the invention provides compounds of Formula II, wherein:
each X is independently O, S, or NR¹R²;
each Y is independently O, S, or NR¹;
each R¹ is independently hydrogen or substituted or unsubstituted alkyl;
each R² is independently substituted or unsubstituted alkyl; and
each m is 3.

In one embodiment, the invention provides compounds of Formula II, wherein:
each X is independently O, S, or NR¹R²;
each Y is independently O, S, or NR¹;
each R¹ is independently substituted or unsubstituted alkyl;
each R² is independently substituted or unsubstituted alkyl; and
each m is 3.

In one embodiment, the invention provides compounds of Formula II, wherein:
each X is independently O, S, or NR¹R²;
each Y is independently O, S, or NR¹;
each R¹ is independently unsubstituted alkyl;
each R² is independently unsubstituted alkyl; and
each m is 3.

In one aspect, the invention provides compounds of Formula III:

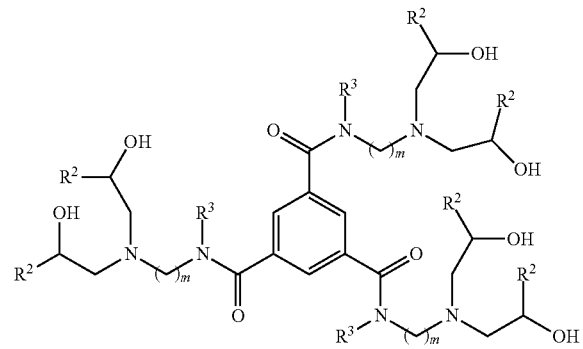

Formula III and salts thereof; wherein
each R² is independently substituted or unsubstituted alkyl;
each R³ is independently hydrogen or substituted or unsubstituted alkyl; and
each m is independently 1, 2, 3, 4, 5, 6, 7, or 8.

In one embodiment, the invention provides compounds of Formula III, wherein:
each R² is independently substituted or unsubstituted alkyl;
each R³ is independently substituted or unsubstituted alkyl; and
each m is independently 1, 2, 3, 4, 5, 6, 7, or 8.

In one embodiment, the invention provides compounds of Formula III, wherein:
each R² is independently unsubstituted alkyl;
each R³ is independently unsubstituted alkyl; and
each m is independently 1, 2, 3, 4, 5, 6, 7, or 8.

In one embodiment, the invention provides compounds of Formula III, wherein:
each R² is independently substituted or unsubstituted alkyl;
each R³ is independently hydrogen or substituted or unsubstituted alkyl; and
each m is 3.

In one embodiment, the invention provides compounds of Formula III, wherein:
each R² is independently substituted or unsubstituted alkyl;
each R³ is independently substituted or unsubstituted alkyl; and
each m is 3.

In one embodiment, the invention provides compounds of Formula III, wherein:
each R² is independently unsubstituted alkyl;
each R³ is independently unsubstituted alkyl; and
each m is 3.

In one aspect, the invention provides compounds of Formula IV:

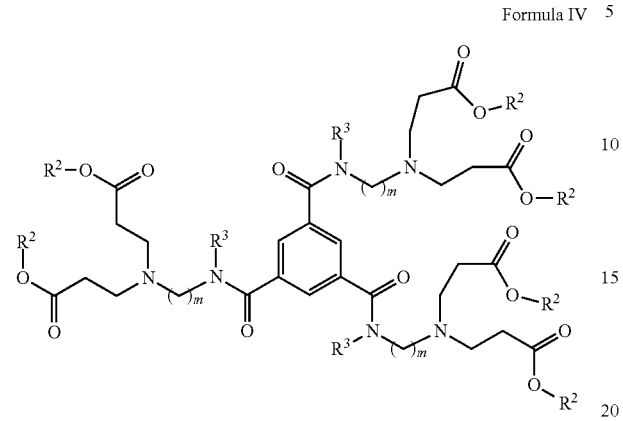

Formula IV and salts thereof; wherein each $R^2$ is independently substituted or unsubstituted alkyl;

each $R^3$ is independently hydrogen or substituted or unsubstituted alkyl; and each m is independently 1, 2, 3, 4, 5, 6, 7, or 8.

In one embodiment, the invention provides compounds of Formula IV, wherein:

each $R^2$ is independently substituted or unsubstituted alkyl;

each $R^3$ is independently substituted or unsubstituted alkyl; and each m is independently 1, 2, 3, 4, 5, 6, 7, or 8.

In one embodiment, the invention provides compounds of Formula IV, wherein:

each $R^2$ is independently unsubstituted alkyl;

each $R^3$ is independently unsubstituted alkyl; and each m is independently 1, 2, 3, 4, 5, 6, 7, or 8.

In one embodiment, the invention provides compounds of Formula IV, wherein:

each $R^2$ is independently substituted or unsubstituted alkyl;

each $R^3$ is independently hydrogen or substituted or unsubstituted alkyl; and each m is 3.

In one embodiment, the invention provides compounds of Formula IV, wherein:

each $R^2$ is independently substituted or unsubstituted alkyl;

each $R^3$ is independently substituted or unsubstituted alkyl; and each m is 3.

In one embodiment, the invention provides compounds of Formula IV, wherein:

each $R^2$ is independently unsubstituted alkyl;

each $R^3$ is independently unsubstituted alkyl; and each m is 3.

In one aspect, the invention provides compounds of Formula V:

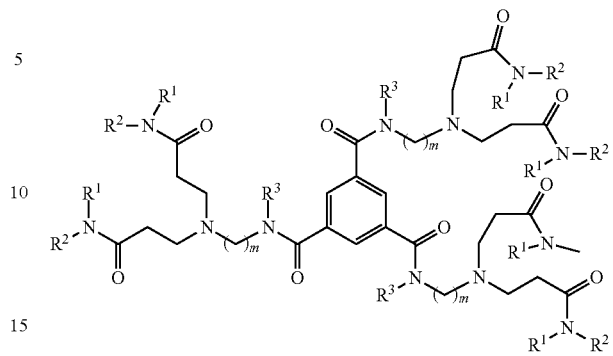

Formula V and salts thereof; wherein each $R^1$ is independently hydrogen or substituted or unsubstituted alkyl;

each $R^2$ is independently substituted or unsubstituted alkyl;

each $R^3$ is independently hydrogen or substituted or unsubstituted alkyl; and each m is independently 1, 2, 3, 4, 5, 6, 7, or 8.

In one embodiment, the invention provides compounds of Formula V, wherein:

each $R^1$ is independently substituted or unsubstituted alkyl;

each $R^2$ is independently substituted or unsubstituted alkyl;

each $R^3$ is independently hydrogen or substituted or unsubstituted alkyl; and each m is independently 1, 2, 3, 4, 5, 6, 7, or 8.

In one embodiment, the invention provides compounds of Formula V, wherein:

each $R^1$ is independently hydrogen or substituted or unsubstituted alkyl;

each $R^2$ is independently substituted or unsubstituted alkyl;

each $R^3$ is independently hydrogen; and each m is independently 1, 2, 3, 4, 5, 6, 7, or 8.

In one embodiment, the invention provides compounds of Formula V, wherein:

each $R^1$ is independently substituted or unsubstituted alkyl;

each $R^2$ is independently substituted or unsubstituted alkyl;

each $R^3$ is hydrogen; and each m is independently 1, 2, 4, 5, 6, 7, or 8.

In one embodiment, the invention provides compounds of Formula V, wherein:

each $R^1$ is independently unsubstituted alkyl;

each $R^2$ is independently unsubstituted each $R^3$ is hydrogen; and each in is independently 1, 2, 3, 4, 5, 6, 7, or 8.

In one embodiment, the invention provides compounds of Formula V wherein:

each $R^1$ is independently hydrogen or substituted or unsubstituted alkyl;

each $R^2$ is independently substituted or unsubstituted alkyl;

each $R^3$ is independently hydrogen or substituted or unsubstituted alkyl; and each m is 3.

In one embodiment, the invention provides compounds of Formula V wherein:

each $R^1$ is independently substituted or unsubstituted alkyl;

each $R^2$ is independently substituted or unsubstituted alkyl;

each $R^3$ is independently hydrogen or substituted or unsubstituted alkyl; and each m is 3.

In one embodiment, the invention provides compounds of Formula V, wherein:
each $R^1$ is independently hydrogen or substituted or unsubstituted alkyl;
each $R^2$ is independently substituted or unsubstituted alkyl;
each $R^3$ is hydrogen; and
each m is 3.

In one embodiment, the invention provides compounds of Formula V, wherein:
each $R^1$ is independently substituted or unsubstituted alkyl;
each $R^2$ is independently substituted or unsubstituted alkyl;
each $R^3$ is hydrogen; and
each m is 3.

In one embodiment, the invention provides compounds of Formula V, wherein:
each $R^1$ is independently hydrogen or substituted or unsubstituted alkyl;
each $R^2$ is independently substituted or unsubstituted alkyl;
each $R^3$ is independently hydrogen or substituted or unsubstituted alkyl; and
each m is 3.

In one embodiment, the invention provides compounds of Formula V wherein:
each $R^1$ is independently unsubstituted alkyl;
each $R^2$ is independently unsubstituted
each $R^3$ is hydrogen; and
each m is 3.

Exemplary compounds of the invention include, but are not limited to, the compounds in Table 1 below.

TABLE 1

Non-limiting examples of Compounds of Formula I

| Compound Name | Structure |
|---|---|
| TT2 | wherein all instances of m = 2 |
| TT3 | wherein all instances of m = 3 |
| TT4 | wherein all instances of m = 4 |

TABLE 1-continued
Non-limiting examples of Compounds of Formula I
| Compound Name | Structure |
| --- | --- |
| TT5 | 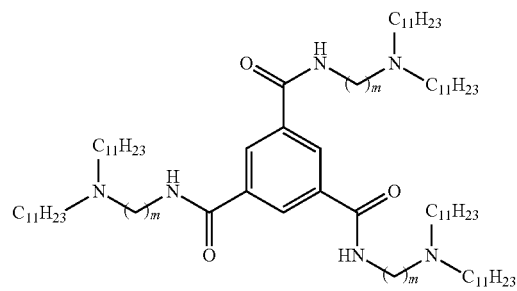
wherein all instances of m = 5 |
| TT6 | 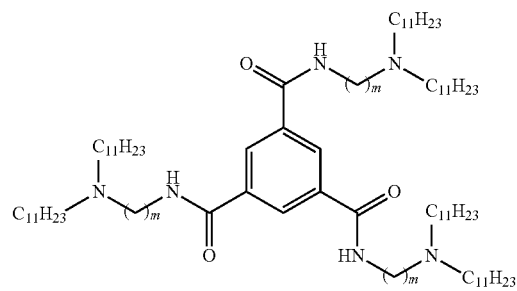
wherein all instances of m = 6 |
| TT7 | 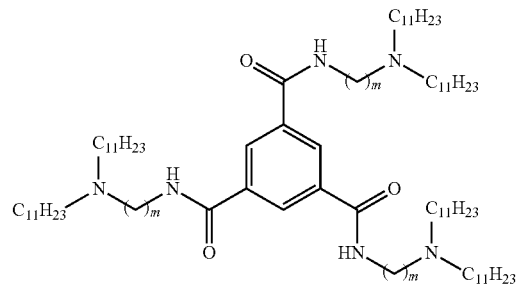
wherein all instances of m = 7 |

TABLE 1-continued
Non-limiting examples of Compounds of Formula I
| Compound Name | Structure |
|---|---|
| TT8 | 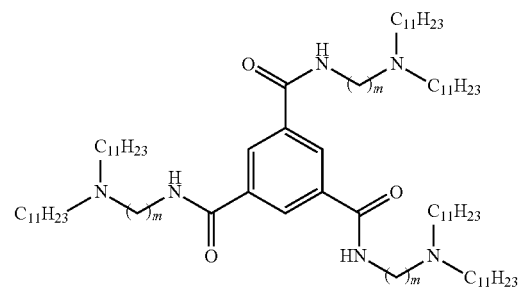<br>wherein all instances of m = 8 |
| III-1 | 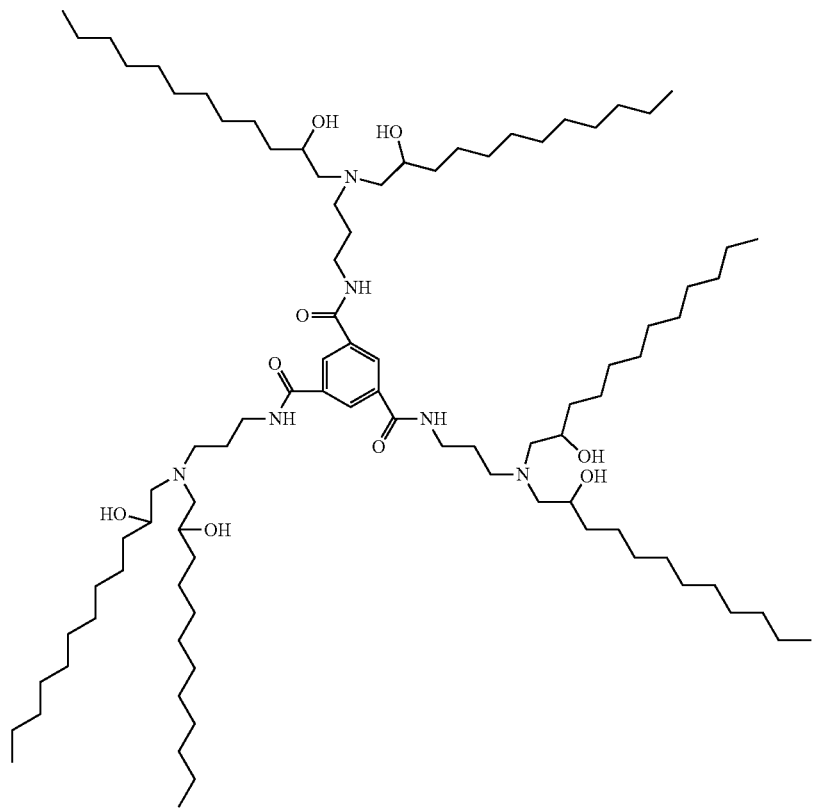 [SMILES: CCCCCCCCCCC(O)CN(CCCNC(=O)c1cc(C(=O)NCCCN(CC(O)CCCCCCCCCC)CC(O)CCCCCCCCCC)cc(C(=O)NCCCN(CC(O)CCCCCCCCCC)CC(O)CCCCCCCCCC)c1)CC(O)CCCCCCCCCC] |

TABLE 1-continued

Non-limiting examples of Compounds of Formula I

| Compound Name | Structure |
|---|---|
| IV-1 | 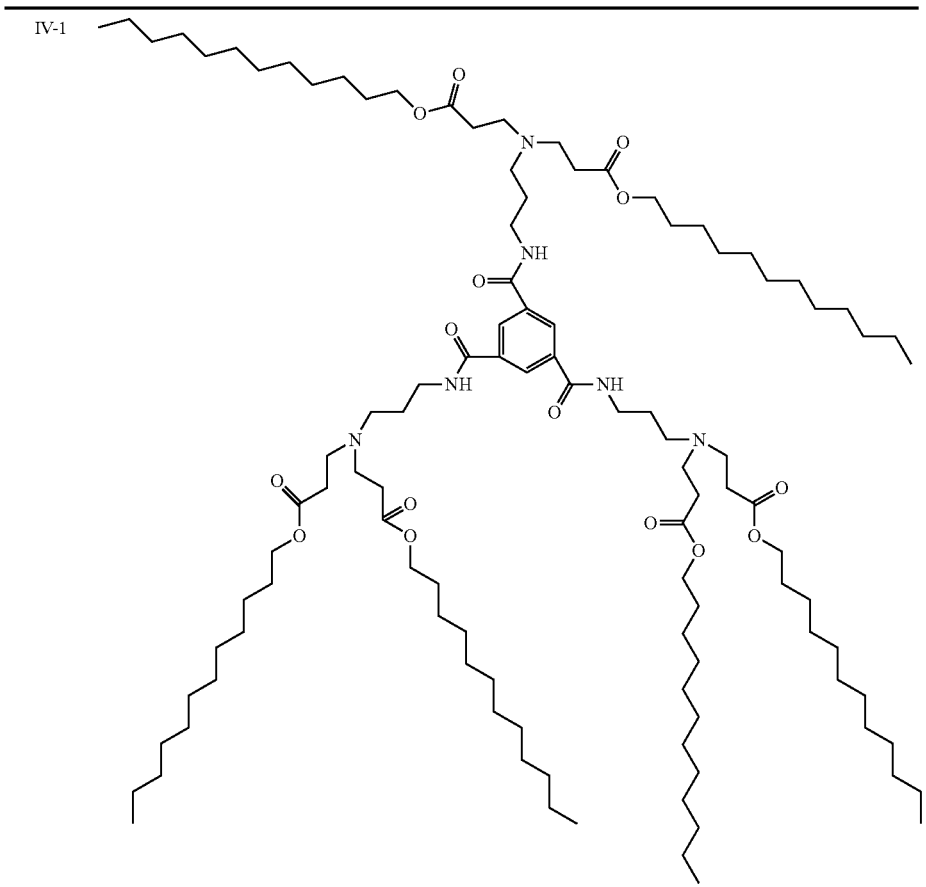 |

In some embodiments, at least one $R^1$ is substituted or unsubstituted $C_{1-24}$ alkyl. In some embodiments, at least one $R^1$ is substituted or unsubstituted $C_{1-18}$ alkyl. In some embodiments, at least one $R^1$ is substituted or unsubstituted $C_{1-12}$ alkyl. In some embodiments, at least one $R^1$ is substituted or unsubstituted $C_{6-18}$ alkyl. In some embodiments, at least one $R^1$ is substituted or unsubstituted $C_{6-12}$ alkyl. In some embodiments, at least one $R^1$ is substituted or unsubstituted $C_{8-12}$ alkyl. In some embodiments, at least one $R^1$ is substituted or unsubstituted $C_{10-12}$ alkyl. In some embodiments, at least one $R^1$ is substituted or unsubstituted $C_{11}$ alkyl.

In some embodiments, at least one $R^2$ is substituted or unsubstituted $C_{1-24}$ alkyl. In some embodiments, at least one $R^2$ is substituted or unsubstituted. $C_{1-18}$ alkyl. In some embodiments, at least one $R^2$ is substituted or unsubstituted $C_{1-12}$ alkyl. In some embodiments, at least one $R^2$ is substituted or unsubstituted $C_{6-18}$ alkyl. In some embodiments, at least one $R^2$ is substituted or unsubstituted $C_{6-12}$ alkyl. In some embodiments, at least one $R^2$ is substituted or unsubstituted $C_{8-12}$ alkyl. In some embodiments, at least one $R^2$ is substituted or unsubstituted $C_{10-12}$ alkyl. In some embodiments, at least one $R^2$ is substituted or unsubstituted $C_{11}$ alkyl.

In some embodiments, at least two $R^1$ are substituted or unsubstituted $C_{1-24}$ alkyl. In some embodiments, at least two $R^1$ are substituted or unsubstituted $C_{1-18}$ alkyl. In some embodiments, at least two $R^1$ are substituted or unsubstituted $C_{1-12}$ alkyl. In some embodiments, at least two $R^1$ are substituted or unsubstituted $C_{6-18}$ alkyl. In some embodiments, at least two $R^1$ are substituted or unsubstituted $C_{6-12}$ alkyl. In some embodiments, at least two $R^1$ are substituted or unsubstituted $C_{8-12}$ alkyl. In some embodiments, at least two $R^1$ are substituted or unsubstituted $C_{10-12}$ alkyl. In some embodiments, at least two $R^1$ are substituted or unsubstituted $C_{11}$ alkyl.

In some embodiments, at least two $R^2$ are substituted or unsubstituted. $C_{1-24}$ alkyl. In some embodiments, at least two $R^2$ are substituted or unsubstituted $C_{1-18}$ alkyl. In some embodiments, at least two $R^2$ are substituted or unsubstituted $C_{1-12}$ alkyl. In some embodiments, at least two $R^2$ are substituted or unsubstituted $C_{6-18}$ alkyl. In some embodiments, at least two $R^2$ are substituted or unsubstituted $C_{6-12}$ alkyl. In some embodiments, at least two $R^2$ are substituted or unsubstituted $C_{8-12}$ alkyl. In some embodiments, at least two $R^2$ are substituted or unsubstituted $C_{10-12}$ alkyl. In some embodiments, at least two $R^2$ are substituted or unsubstituted alkyl.

In some embodiments, all instances of $R^1$ are substituted or unsubstituted $C_{1-24}$ alkyl. In some embodiments, all instances of $R^1$ are substituted or unsubstituted $C_{1-18}$ alkyl. In some embodiments, all instances of $R^1$ are substituted or unsubstituted $C_{1-12}$ alkyl. In some embodiments, all instances of $R^1$ are substituted or unsubstituted $C_{6-18}$ alkyl. In some embodiments, all instances of $R^1$ are substituted or unsubstituted $C_{6-12}$ alkyl. In some embodiments, all instances of $R^1$ are substituted or unsubstituted $C_{8-12}$ alkyl. In some embodiments, all instances of $R^1$ are substituted or unsubstituted $C_{10-12}$ alkyl. In some embodiments, all instances of $R^1$ are substituted or unsubstituted $C_{11}$ alkyl.

In some embodiments, all instances of $R^2$ are substituted or unsubstituted $C_{1-24}$ alkyl. In some embodiments, all instances of $R^2$ are substituted or unsubstituted $C_{1-18}$ alkyl. In some embodiments, all instances of $R^2$ are substituted or unsubstituted $C_{1-12}$ alkyl. In some embodiments, all instances of $R^2$ are substituted or unsubstituted. $C_{6-18}$ alkyl. In some embodiments, all instances of $R^2$ are substituted or unsubstituted $C_{6-12}$ alkyl. In some embodiments, all instances of $R^2$ are substituted or unsubstituted. $C_{8-12}$ alkyl. In some embodiments, all instances of $R^2$ are substituted or unsubstituted $C_{10-12}$ alkyl. In some embodiments, all instances of $R^2$ are substituted or unsubstituted $C_{11}$ alkyl.

In some embodiments, at least one $R^1$ is substituted alkyl, wherein the substituted alkyl is substituted with a halogen. In some embodiments, at least one $R^1$ is substituted alkyl, wherein the substituted alkyl is substituted with fluorine. In some embodiments, at least one $R^1$ is substituted alkyl, wherein the substituted alkyl is substituted with halogenated alkyl.

In some embodiments, at least one $R^2$ is substituted alkyl, wherein the substituted alkyl is substituted with a halogen. In some embodiments, at least one $R^2$ is substituted alkyl, wherein the substituted alkyl is substituted with fluorine. In some embodiments, at least one $R^2$ is substituted alkyl, wherein the substituted alkyl is substituted with halogenated alkyl.

In some embodiments, at least two $R^1$ are substituted alkyl, wherein the substituted alkyl is substituted with a halogen. In some embodiments, at least two $R^1$ are substituted alkyl, wherein the substituted alkyl is substituted with fluorine. In some embodiments, at least two $R^1$ are substituted alkyl, wherein the substituted alkyl is substituted with halogenated alkyl.

In some embodiments, at least two $R^2$ are substituted alkyl, wherein the substituted alkyl is substituted with a halogen. In some embodiments, at least two $R^2$ are substituted alkyl, wherein the substituted alkyl is substituted with fluorine. In some embodiments, at least two $R^2$ are substituted alkyl, wherein the substituted alkyl is substituted with halogenated alkyl.

In some embodiments, all instances of $R^1$ are substituted alkyl, wherein the substituted alkyl is substituted with a halogen. In some embodiments, all instances of $R^1$ are substituted alkyl, wherein the substituted alkyl is substituted with fluorine. In some embodiments, all instances of $R^1$ are substituted alkyl, wherein the substituted alkyl is substituted with halogenated alkyl.

In some embodiments, all instances of $R^2$ are substituted alkyl, wherein the substituted alkyl is substituted with a halogen. In some embodiments, all instances of $R^2$ are substituted alkyl, wherein the substituted alkyl is substituted with fluorine. In some embodiments, all instances of $R^2$ are substituted alkyl, wherein the substituted alkyl is substituted with halogenated alkyl.

In some embodiments, at least one $R^3$ is hydrogen, in some embodiments, at least one $R^3$ is substituted or unsubstituted alkyl. In some embodiments, at least one $R^3$ is substituted or unsubstituted $C_{1-18}$ alkyl. In some embodiments, at least one $R^3$ is substituted or unsubstituted $C_{1-12}$ alkyl. In some embodiments, at least one $R^3$ is substituted or unsubstituted $C_{1-6}$ alkyl. In some embodiments, at least one $R^3$ is substituted or unsubstituted $C_{1-4}$ alkyl. In some embodiments, at least one $R^3$ is substituted or unsubstituted $C_{2-4}$ alkyl. In some embodiments, at least one $R^3$ is substituted or unsubstituted methyl.

In some embodiments, at least one $R^3$ is substituted alkyl, wherein the substituted alkyl is substituted with a halogen. In some embodiments, at least one $R^3$ is substituted alkyl, wherein the substituted alkyl is substituted with fluorine. In some embodiments, at least one $R^3$ is substituted alkyl, wherein the substituted alkyl is substituted with halogenated alkyl.

In some embodiments, at least two $R^3$ are hydrogen. In some embodiments, at least two $R^3$ are substituted or unsubstituted alkyl. In some embodiments, at least two $R^3$ are substituted or unsubstituted $C_{1-18}$ alkyl. In some embodiments, at least two $R^3$ are substituted or unsubstituted $C_{1-12}$ alkyl. In some embodiments, at least two $R^3$ are substituted or unsubstituted $C_{1-6}$ alkyl. In some embodiments, at least two $R^3$ are substituted or unsubstituted $C_{1-4}$ alkyl. In some embodiments, at least two $R^3$ are substituted or unsubstituted $C_{2-4}$ alkyl. In some embodiments, at least two $R^3$ are substituted or unsubstituted methyl.

In some embodiments, at least two $R^3$ are substituted alkyl, wherein the substituted alkyl is substituted with a halogen. In some embodiments, at least two $R^3$ are substituted alkyl, wherein the substituted alkyl is substituted with fluorine. In some embodiments, at least two $R^3$ are substituted alkyl, wherein the substituted alkyl is substituted with halogenated alkyl.

In some embodiments, all instances of $R^3$ are hydrogen. In some embodiments, all instances of $R^3$ are substituted or unsubstituted alkyl. In some embodiments, all instances of $R^3$ are substituted or unsubstituted $C_{1-18}$ alkyl. In some embodiments, all instances of $R^3$ are substituted or unsubstituted $C_{1-12}$ alkyl. In some embodiments, all instances of $R^3$ are substituted or unsubstituted $C_{1-6}$ alkyl. In some embodiments, all instances of $R^3$ are substituted or unsubstituted $C_{1-4}$ alkyl. In some embodiments, all instances of $R^3$ are substituted or unsubstituted $C_{2-4}$ alkyl. In some embodiments, all instances of $R^3$ are substituted or unsubstituted methyl.

In some embodiments, all instances of $R^3$ are substituted alkyl, wherein the substituted alkyl is substituted with a halogen. In some embodiments, all instances of $R^3$ are substituted alkyl, wherein the substituted alkyl is substituted with fluorine. In some embodiments, all instances of $R^3$ are substituted alkyl, wherein the substituted alkyl is substituted with halogenated alkyl.

In some embodiments, at least one m is 1, In some embodiments, at least one m is 2. In some embodiments, at least one m is 3. In some embodiments, at least one m is 4. In some embodiments, at least one m is 5. In some embodiments, at least one m is 6. In some embodiments, at least one m is 7. In some embodiments, at least one m is 8.

In some embodiments, at least two m are 1. In some embodiments, at least two m are 2. In some embodiments, at least two m are 3. In some embodiments, at least two m are 4. In some embodiments, at least two m are 5. In some embodiments, at least two m are 6. In some embodiments, at least two m are 7. In some embodiments, at least two m are 8.

In some embodiments, all instances of m are 1. In some embodiments, all instances of m are 2. In some embodiments, all instances of m are 3. In some embodiments, all instances of m are 4. In some embodiments, all instances of m are 5. In some embodiments, all instances of m are 6. In some embodiments, all instances of m are 7. In some embodiments, all instances of m are 8.

In one aspect, the invention provides compounds of Formula I:

*Formula I* and salts thereof; wherein
all instances of $R^1$ are hydrogen or substituted or unsubstituted alkyl;
all instances of $R^2$ are substituted or unsubstituted alkyl;
all instances of $R^3$ are hydrogen or substituted or unsubstituted alkyl; and
all instances of m are 1, 2, 3, 4, 5, 6, 7, or 8.

In one embodiment, the invention provides compounds of Formula I, wherein:
all instances of $R^1$ are substituted or unsubstituted alkyl;
all instances of $R^2$ are substituted or unsubstituted alkyl;
all instances of $R^3$ are hydrogen or substituted or unsubstituted alkyl; and
all instances of m are 1, 2, 3, 4, 5, 6, 7, or 8.

In one embodiment, the invention provides compounds of Formula I, wherein:
all instances of $R^1$ are hydrogen or substituted or unsubstituted alkyl;
all instances of $R^1$ are substituted or unsubstituted alkyl;
all instances of $R^3$ are hydrogen; and
all instances of m are 1, 2, 3, 4, 5, 6, 7, or 8.

In one embodiment, the invention provides compounds of Formula I, wherein:
all instances of $R^1$ are substituted or unsubstituted alkyl;
all instances of $R^2$ are substituted or unsubstituted alkyl;
all instances of $R^3$ are hydrogen; and
all instances of m are 1, 2, 3, 4, 5, 6, 7, or 8.

In one embodiment, the invention provides compounds of Formula I, wherein:
all instances of $R^1$ are unsubstituted alkyl;
all instances of $R^2$ are unsubstituted alkyl;
all instances of $R^3$ are hydrogen; and
all instances of m are 1, 3, 4, 5, 6, 7, or 8.

In one embodiment, the invention provides compounds of Formula I, wherein:
all instances of $R^1$ are hydrogen or substituted or unsubstituted alkyl;
all instances of $R^2$ are substituted or unsubstituted alkyl;
all instances of $R^3$ are hydrogen or substituted or unsubstituted alkyl; and
all instances of m are 3.

In one embodiment, the invention provides compounds of Formula I, wherein:
all instances of $R^1$ are substituted or unsubstituted alkyl;
all instances of $R^2$ are substituted or unsubstituted alkyl;
all instances of $R^3$ are hydrogen or substituted or unsubstituted alkyl; and
all instances of m are 3.

In one embodiment, the invention provides compounds of Formula I, wherein:
all instances of $R^1$ are hydrogen or substituted or unsubstituted alkyl;
all instances of $R^2$ are substituted or unsubstituted alkyl;
all instances of $R^3$ are hydrogen; and
all instances of m are 3.

In one embodiment, the invention provides compounds of Formula I, wherein:
all instances of $R^1$ are substituted or unsubstituted alkyl;
all instances of $R^2$ are substituted or unsubstituted alkyl;
all instances of $R^3$ are hydrogen; and
all instances of m are 3.

In one embodiment, the invention provides compounds of Formula I, wherein:
all instances of $R^1$ are hydrogen or substituted or unsubstituted alkyl;
all instances of $R^1$ are substituted or unsubstituted alkyl;
all instances of $R^3$ are hydrogen or substituted or unsubstituted alkyl; and
all instances of m are 3.

In one embodiment, the invention provides compounds of Formula I, wherein:
all instances of $R^1$ are unsubstituted alkyl;
all instances of $R^2$ are unsubstituted alkyl;
all instances of $R^3$ are hydrogen; and
all instances of m are 3.

In one aspect, the invention provides compounds of Formula Ia:

*Formula Ia* and salts thereof; wherein
all instances of $R^1$ are hydrogen or substituted or unsubstituted alkyl;
all instances of $R^2$ are substituted or unsubstituted alkyl; and
all instances of m are 1, 2, 3, 4, 5, 6, 7, or 8.

In one embodiment, the invention provides compounds of Formula Ia, wherein:
all instances of $R^1$ are substituted or unsubstituted alkyl;
all instances of $R^2$ are substituted or unsubstituted alkyl; and
all instances of m are 1, 2, 3, 4, 5, 7, or 8.

In one embodiment, the invention provides compounds of Formula Ia, wherein:
all instances of $R^1$ are unsubstituted alkyl;
all instances of $R^2$ are unsubstituted alkyl; and
all instances of m are 1, 2, 3, 4, 5, 7, or 8.

In one embodiment, the invention provides compounds of Formula Ia, wherein:
all instances of $R^1$ are hydrogen or substituted or unsubstituted alkyl;
all instances of $R^2$ are substituted or unsubstituted alkyl; and
all instances of m are 3.

In one embodiment, the invention provides compounds of Formula Ia, wherein:
all instances of $R^1$ are substituted or unsubstituted alkyl;
all instances of $R^2$ are substituted or unsubstituted alkyl; and
all instances of m are 3.

In one embodiment, the invention provides compounds of Formula Ia, wherein:
all instances of $R^1$ are unsubstituted alkyl;
all instances of $R^2$ are unsubstituted alkyl; and
all instances of m are 3.

In one aspect, the invention provides compounds of Formula II:

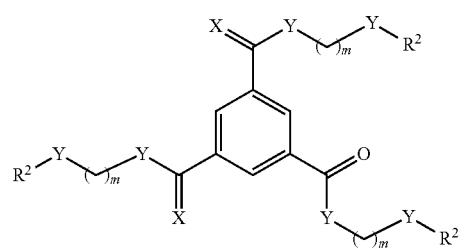

Formula II and salts thereof; wherein
all instances of X are O, S, or $NR^1R_2$; and
all instances of Y are O, S, or $NR^1$,
all instances of $R^1$ are hydrogen or substituted or unsubstituted alkyl.
all instances of $R^2$ are substituted or unsubstituted alkyl; and
all instances of m are 1, 2, 3, 4, 5, 6, 7, or 8.

In one embodiment, the invention provides compounds of Formula II, wherein:
all instances of X are O, S, or $NR^1R^2$; and
all instances of Y are O, S, or $NR^1$,
all instances of $R^1$ are substituted or unsubstituted alkyl.
all instances of $R^2$ are substituted or unsubstituted alkyl; and
all instances of m are 1, 2, 3, 4, 5, 6, 7, or 8.

In one embodiment, the invention provides compounds of Formula II, wherein:
all instances of X are O, S, or $NR^1R^2$; and
all instances of Y are O, S, or $NR^1$;
all instances of $R^1$ are unsubstituted alkyl.
all instances of $R^2$ are unsubstituted alkyl; and
all instances of m are 1, 2, 3, 4, 5, 6, 7, or 8.

In one embodiment, the invention provides compounds of Formula II, wherein:
all instances of X are O, S, or $NR^1R^2$; and
all instances of Y are O, S, or $NR^1$,
all instances of $R^1$ are hydrogen or substituted or unsubstituted alkyl.
all instances of $R^2$ are substituted or unsubstituted alkyl; and
all instances of m are 3.

In one embodiment, the invention provides compounds of Formula II, wherein:
all instances of X are O, S, or $NR^1R^2$; and
all instances of Y are O, S, or
all instances of $R^1$ are substituted or unsubstituted alkyl.
all instances of $R^2$ are substituted or unsubstituted alkyl; and
all instances of m are 3.

In one embodiment, the invention provides compounds of Formula II, wherein:
all instances of X are O, S, or $NR^1R^2$; and
all instances of Y are O, S, or $NR^1$,
all instances of $R^1$ are unsubstituted alkyl.
all instances of $R^2$ are unsubstituted alkyl; and
all instances of m are 3.

In one aspect, the invention provides compounds of Formula III:

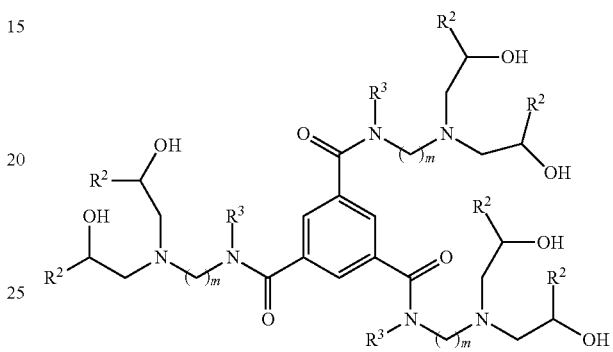

Formula III and salts thereof; wherein
all instances of $R^2$ are substituted or unsubstituted alkyl;
all instances of $R^3$ are independently hydrogen or substituted or unsubstituted alkyl; and
all instances of m are independently 1, 2, 3, 4, 5, 6, 7, or 8.

In one embodiment, the invention provides compounds of Formula III, wherein:
all instances of $R^2$ are substituted or unsubstituted alkyl;
all instances of $R^3$ are substituted or unsubstituted alkyl; and
all instances of m are independently 1, 2, 3, 4, 5, 6, 7, or 8.

In one embodiment, the invention provides compounds of Formula III, wherein:
all instances of $R^2$ are unsubstituted alkyl;
all instances of $R^3$ are unsubstituted alkyl; and
all instances of m are independently 1, 2, 3, 4, 5, 6, 7, or 8.

In one embodiment, the invention provides compounds of Formula III, wherein:
all instances of $R^2$ are substituted or unsubstituted alkyl;
all instances of $R^3$ are hydrogen or substituted or unsubstituted alkyl; and
all instances of m are 3.

In one embodiment, the invention provides compounds of Formula III, wherein:
all instances of $R^2$ substituted or unsubstituted alkyl;
all instances of $R^3$ are substituted or unsubstituted alkyl; and
all instances of m are 3.

In one embodiment, the invention provides compounds of Formula III, wherein:
all instances of $R^2$ are independently unsubstituted alkyl;
all instances of $R^3$ are unsubstituted alkyl; and
all instances of m are 3.

In one aspect, the invention provides compounds of Formula IV:

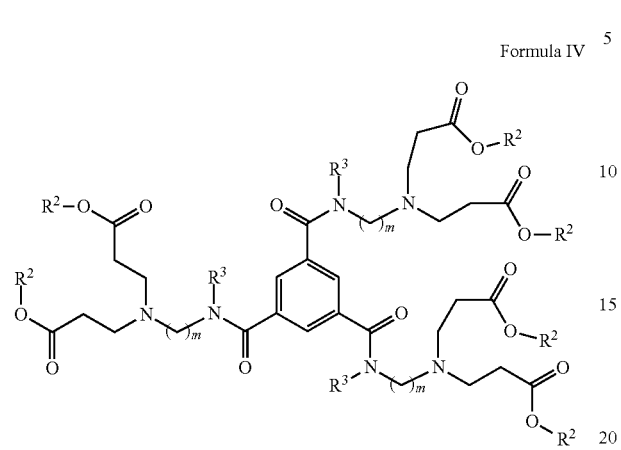

Formula IV and salts thereof; wherein all instances of $R^2$ are substituted or unsubstituted alkyl;

all instances of $R^3$ are hydrogen or substituted or unsubstituted alkyl; and all instances of m are 1, 2, 3, 4, 5, 6, 7, or 8.

In one embodiment, the invention provides compounds of Formula IV, wherein:

all instances of $R^2$ are substituted or unsubstituted alkyl;

all instances of $R^3$ are substituted or unsubstituted alkyl; and all instances of m are 1, 2, 3, 4, 5, 6, 7, or 8.

In one embodiment, the invention provides compounds of Formula IV, wherein:

all instances of $R^2$ are unsubstituted alkyl;

all instances of $R^3$ are unsubstituted alkyl; and all instances of m are 1, 2, 3, 4, 5, 6, 7, or 8.

In one embodiment, the invention provides compounds of Formula IV, wherein:

all instances of $R^2$ are substituted or unsubstituted alkyl;

all instances of $R^3$ are hydrogen or substituted or unsubstituted alkyl; and all instances of m are 3.

In one embodiment, the invention provides compounds of Formula IV, wherein:

all instances of $R^2$ are substituted or unsubstituted alkyl;

all instances of $R^3$ are substituted or unsubstituted alkyl; and all instances of m are 3.

In one embodiment, the invention provides compounds of Formula IV, wherein:

all instances of $R^2$ are unsubstituted alkyl;

all instances of $R^3$ are unsubstituted alkyl; and all instances of m are 3.

In one aspect, the invention provides compounds of Formula V:

Formula V and salts thereof; wherein all instances of $R^1$ are hydrogen or substituted or unsubstituted alkyl;

all instances of $R^2$ are substituted or unsubstituted alkyl;

all instances of $R^3$ are hydrogen or substituted or unsubstituted alkyl; and all instances of m are 1, 2, 3, 4, 5, 6, 7, or 8.

In one embodiment, the invention provides compounds of Formula I, wherein:

all instances of $R^1$ are substituted or unsubstituted alkyl;

all instances of $R^2$ are substituted or unsubstituted alkyl;

all instances of $R^3$ are hydrogen or substituted or unsubstituted alkyl; and all instances of m are 1, 2, 3, 4, 5, 6, 7, or 8.

In one embodiment, the invention provides compounds of Formula I, wherein:

all instances of $R^1$ are hydrogen or substituted or unsubstituted alkyl;

all instances of $R^1$ are substituted or unsubstituted alkyl;

all instances of $R^3$ are hydrogen; and all instances of m are 1, 2, 3, 4, 5, 6, 7, or 8.

In one embodiment, the invention provides compounds of Formula I, wherein:

all instances of IV are substituted or unsubstituted alkyl;

all instances of $R^2$ are substituted or unsubstituted alkyl;

all instances of $R^1$ are hydrogen; and all instances of m are 1, 2, 3, 4, 5, 6, 7, or 8.

In one embodiment, the invention provides compounds of Formula I, wherein:

all instances of $R^1$ are unsubstituted alkyl;

all instances of $R^2$ are unsubstituted alkyl;

all instances of $R^1$ are hydrogen; and all instances of m are 1, 3, 4, 5, 6, 7, or 8.

In one embodiment, the invention provides compounds of Formula I, wherein:

all instances of $R^1$ are hydrogen or substituted or unsubstituted alkyl;

all instances of $R^2$ are substituted or unsubstituted alkyl;

all instances of $R^3$ are hydrogen or substituted or unsubstituted alkyl; and all instances of m are 3.

In one embodiment, the invention provides compounds of Formula I, wherein:

all instances of $R^1$ are substituted or unsubstituted alkyl;

all instances of $R^2$ are substituted or unsubstituted alkyl;

all instances of $R^3$ are hydrogen or substituted or unsubstituted alkyl; and all instances of m are 3.

In one embodiment, the invention provides compounds of Formula I, wherein:
all instances of $R^1$ are hydrogen or substituted or unsubstituted alkyl;
all instances of $R^2$ are substituted or unsubstituted alkyl;
all instances of $R^3$ are hydrogen; and
all instances of m are 3.

In one embodiment, the invention provides compounds of Formula I, wherein:
all instances of $R^1$ are substituted or unsubstituted alkyl;
all instances of $R^2$ are substituted or unsubstituted alkyl;
all instances of $R^3$ are hydrogen; and
all instances of m are 3.

In one embodiment, the invention provides compounds of Formula I, wherein:
all instances of $R^1$ are hydrogen or substituted or unsubstituted alkyl;
all instances of $R^2$ are substituted or unsubstituted alkyl;
all instances of $R^3$ are hydrogen or substituted or unsubstituted alkyl; and
all instances of m are 3.

In one embodiment, the invention provides compounds of Formula I, wherein:
all instances of $R^1$ are unsubstituted alkyl;
all instances of $R^2$ are unsubstituted alkyl;
all instances of $R^3$ are hydrogen; and
all instances of m are 3.

Lipid-Like Nanoparticles (LLNs)

In one aspect, the invention provides a nanoparticle comprising:
a compound of Formula I, II, III, IV, or V;
a non-cationic lipid;
a polyethylene glycol-lipid; and
a sterol.

The various compounds of Formula I, II, III, IV, or V are described in the Compounds section above. In some embodiments, the nanoparticle comprises a compound of Formula I, II, III, IV, or V in a molar ratio of about 10% to about 40%. In some embodiments, the nanoparticle comprises a compound of Formula I, II, III, IV, or V in a molar ratio of about 10%, about 15%, about 20%, about 25%, about 30%, about 35%, or about 40%. In one embodiment, the nanoparticle comprises a compound of Formula I, II, III, IV, or V in a molar ratio of about 20%.

In some embodiments, the nanoparticle comprises a non-cationic lipid. IN some embodiments, the non-cationic lipid interacts with TT lipids as a helper lipid. In some embodiments, the non-cationic lipid can include, but is not limited to, 1,2-dioleoyl-sn-glycero-3-phosphoethanolamine (DOPE), 1-palmitoyl-2-oleoyl-sn-glycero-3-phosphoethanolamine (POPE), 1,2-distearoyl-sn-glycero-3-phosphocholine (DSPC), 1-stearoyl-2-oleoyl-sn-glycero-3-phosphoethanolamine (SOPE), (1,2-dipalmitoyl-sn-glycero-3-phosphocholine), 1,2-dioleyl-sn-glycero-3-phosphotidycholine (DOPC), 1,2-dipalmitoyl-sn-glycero-3-phosphoethanolamine (DPPE), 1,2-dimyristoyl-sn-glycero-3-phosphoethanolamine (DMPE), 1,2-dioleoyl-5/7-glycero-3-phospho-(1'-rac-glycerol) (DOPG), or combinations thereof. In one embodiment, the non-cationic lipid is 1,2-dioleoyl-sn-glycero-3-phosphoethanolamine (DOPE). In one embodiment, the non-cationic lipid is 1-palmitoyl-2-oleoyl-sn-glycero-3-phosphoethanolamine (POPE). In one embodiment, the non-cationic lipid is 1,2-distearoyl-sn-gtycero-3-phosphocholine (DSPC). In one embodiment, the non-cationic lipid is 1-stearoyl-2-oleoyl-sn-glycero-3-phosphoethanolamine (SOPE).

In some embodiments, the nanoparticle comprises a non-cationic lipid in a molar ratio of about 10% to about 40%. In some embodiments, the nanoparticle comprises a non-cationic lipid in a molar ratio of about 10%, about 15%, about 20%, about 25%, about 30%, about 35%, or about 40%. In one embodiment, the nanoparticle comprises a non-cationic lipid in a molar ratio of about 30%.

In some embodiments, the nanoparticle of invention includes a polyethylene glycol-lipid (PEG-lipid). PEG-lipid is incorporated to form a hydrophilic outer layer and stabilize the particles. Nonlimiting examples of polyethylene glycol-lipids include PEG-modified lipids such as PEG-modified phosphatidylethanolamines, PEG-modified phosphatidic acids, PEG-modified ceramides, PEG-modified dialkylamines, PEG-modified diacylglycerols, and PEG-modified dialkylglycerols. Representative polyethylene glycol-lipids include DMG-PEG, DLPE-PEGs, DMPE-PEGS, DPPC-PEGS, and DSPE-PEGs. In one embodiment, the polyethylene is 1,2-dimyristoyl-sn-glycerol, methoxypolyethylene glycol (DMG-PEG). In one embodiment, the polyethylene glycol-lipid is 1,2-dimyristoyl-sn-glycerol, methoxypolyethylene glycol-2000 (DMG-PEG2000). DMG-PEGXXXX means 1,2-dimyristoyl-sn-glycerol, methoxypolyethylene glycol-XXXX, wherein XXXX signifies the molecular weight of the polyethylene glycol moiety, e.g. DMG-PEG2000 or DMG-PEG5000.

In some embodiments, the nanoparticle comprises a polyethylene glycol-lipid in a molar ratio of about 0% to about 5%. In some embodiments, the nanoparticle comprises a polyethylene glycol-lipid in a molar ratio of about 0%, about 0.25%, about 0.5%, about 0.75%, about 1%, about 1.5%, about 2%, about 3%, about 4%, or about 5%. In one embodiment, the nanoparticle comprises a polyethylene glycol-lipid in a molar ratio of about 0.75%.

In some embodiments, the nanoparticle of invention includes a sterol. Sterols are well known to those skilled in the art and generally refers to those compounds having a perhydrocyclopentanophenanthrene ring system and having one or more OH substituents. Examples of sterols include, but are not limited to, cholesterol, campesterol, ergosterol, sitosterol, and the like.

In some embodiments, the sterol is selected from a cholesterol-based lipids. In some embodiments, the one or more cholesterol-based lipids are selected from cholesterol, PEGylated cholesterol, DC-Choi (N,N-dimethyl-N-ethyl-carboxamidocholesterol), 1,4-bis(3-N-oleylamino-propyl)piperazine, or combinations thereof.

The sterol can be used to tune the particle permeability and fluidity base on its function in cell membranes. In one embodiment, the sterol is cholesterol.

In some embodiments, the nanoparticle comprises a sterol in a molar ratio of about 25% to about 50%. In some embodiments, the nanoparticle comprises a sterol in a molar ratio of about 25%, about 30%, about 35%, about 40%, about 45%, or about 50%. In one embodiment, the nanoparticle comprises a sterol in a molar ratio of about 40%.

In one embodiment, the invention provides a nanoparticle comprising:
a compound of Formula I, II, III, IV, or V at a molar ratio of about 20%;
a non-cationic lipid at a molar ratio of about 30%;

a polyethylene glycol-lipid at a molar ratio of about 0.75%; and a sterol at a molar ratio of about 40%.

In one embodiment, the invention provides a nanoparticle comprising:

a compound of Formula I, II, III, IV, or V;

1,2-dioleoyl-sn-glycero-3-phosphoethanolamine (DOPE);

methoxypolyethylene glycol (DM-PEG$_{2000}$), and cholesterol.

In one embodiment, the invention provides a nanoparticle comprising:

compound TT3;

1,2-dioleoyl-sn-glycero-3-phosphoethanolamine (DOPE);

1,2-dimyristoyl-sn-glycerol, methoxypolyethylene glycol (DMG-PEG$_{2000}$); and cholesterol.

In one embodiment, the nanoparticle further comprises an agent. In one embodiment, the nanoparticle further comprises a therapeutic agent. In one embodiment, the nanoparticle further comprises a diagnostic agent.

The agents delivered into cells can be a polynucleotide. Polynucleotides or oligonucleotides that can be introduced according to the invention methods include DNA, cDNA, and RNA sequences of all types. For example, the polynucleotide can be double stranded DNA, single-stranded DNA, complexed DNA, encapsulated DNA, naked RNA, encapsulated RNA, messenger RNA (mRNA), tRNA, short interfering RNA (siRNA), double stranded RNA (dsRNA), micro-RNA (miRNA), antisense RNA (asRNA) and combinations thereof. The polynucleotides can also be DNA constructs, such as expression vectors, expression vectors encoding a desired gene product (e.g., a gene product homologous or heterologous to the subject into which it is to be introduced), and the like. In one embodiment, the agent is an mRNA. The term "nanoparticle" and "lipid-like nanoparticle (LLN)" are used interchangeably in the present disclosure.

Compositions

Compositions, as described herein, comprising an active compound and an excipient of some sort may be useful in a variety of medical and non-medical applications. For example, pharmaceutical compositions comprising an active compound (active compounds include those compounds of Formula I, II, III, IV, or V) and an excipient may be useful in the delivery of an effective amount of an agent to a subject in need thereof. Nutraceutical compositions comprising an active compound and an excipient may be useful in the delivery of an effective amount of a nutraceutical, e.g., a dietary supplement, to a subject in need thereof. Cosmetic compositions comprising an active compound and an excipient may be formulated as a cream, ointment, balm, paste, film, or liquid, etc., and may be useful in the application of make-up, hair products, and materials useful for personal hygiene, etc. Compositions comprising an active compound and an excipient may be useful for non-medical applications, e.g., such as an emulsion or emulsifier, useful, for example, as a food component, for extinguishing fires, for disinfecting surfaces, for oil cleanup, etc.

In certain embodiments, the composition further comprises an agent, as described herein. For example, in certain embodiments, the agent is a small molecule, organometallic compound, nucleic acid, protein, peptide, polynucleotide, metal, targeting agent, an isotopically labeled chemical compound, drug, vaccine, immunological agent, or an agent useful in bioprocessing. In certain embodiments, the agent is a polynucleotide. In certain embodiments, the polynucleotide is DNA or RNA. In certain embodiments, the RNA is RNAi, dsRNA, siRNA, shRNA, miRNA, or antisense RNA. In certain embodiments, the polynucleotide and the one or more active compounds are not covalently attached.

In one aspect, the invention provides a composition comprising:

a compound of Formula I, II, III, IV, or V; and an agent.

In one aspect, the invention provides a composition comprising:

a nanoparticle, comprising a compound of Formula I, II, III, IV, or V; and an agent.

In some embodiments, the composition further comprises a non-cationic lipid (helper lipid). In some embodiments, the composition further comprises a polyethylene glycol-lipid (PEG modified lipid). In some embodiments, the composition further comprises a sterol.

In some embodiments, the composition further comprises a non-cationic lipid (helper lipid); and/or a polyethylene glycol-lipid (PEG modified lipid); and/or a sterol.

"Excipients" include any and all solvents, diluents or other liquid vehicles, dispersion or suspension aids, surface active agents, isotonic agents, thickening or emulsifying agents, preservatives, solid binders, lubricants and the like, as suited to the particular dosage form desired. General considerations in formulation and/or manufacture can be found, for example, in *Remington's Pharmaceutical Sciences*, Sixteenth Edition, E. W. Martin (Mack Publishing Co., Easton, Pa., 1980), and *Remington: The Science and Practice of Pharmacy,* 21st Edition (Lippincott Williams & Wilkins, 2005).

Exemplary excipients include, but are not limited to, any non-toxic, inert solid, semi-solid or liquid filler, diluent, encapsulating material or formulation auxiliary of any type. Some examples of materials which can serve as excipients include, but are not limited to, sugars such as lactose, glucose, and sucrose; starches such as corn starch and potato starch; cellulose and its derivatives such as sodium carboxymethyl cellulose, ethyl cellulose, and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols such as propylene glycol; esters such as ethyl oleate and ethyl laurate; agar; detergents such as Tween 80; buffering agents such as magnesium hydroxide and aluminum hydroxide; alginic acid; pyrogen-free water; isotonic saline; Ringer's solution; ethyl alcohol; and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. As would be appreciated by one of skill in this art, the excipients may be chosen based on what the composition is useful for. For example, with a pharmaceutical composition or cosmetic composition, the choice of the excipient will depend on the route of administration, the agent being delivered, time course of delivery of the agent, etc., and can be administered to humans and/or to animals, orally, rectally, parenterally, intracisternally, intravaginally, intranasally, intraperitoneally, topically (as by powders, creams, ointments, or drops), bucally, or as an oral or nasal spray.

Exemplary diluents include calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, etc., and combinations thereof.

Exemplary granulating and/or dispersing agents include potato starch, corn starch, tapioca starch, sodium starch glycolate, clays, alginic acid, guar gum, citrus pulp, agar, bentonite, cellulose and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, etc., and combinations thereof.

Exemplary surface active agents and/or emulsifiers include natural emulsifiers (e.g. acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g. bentonite [aluminum silicate] and Veegum [magnesium aluminum silicate]), long chain amino acid derivatives, high molecular weight alcohols (e.g. stearyl alcohol, cetyl alcohol, oleyl alcohol, triacetin monostearate, ethylene glycol distearate, glyceryl monostearate, and propylene glycol monostearate, polyvinyl alcohol), carbomers (e.g. carboxy polymethylene, polyacrylic acid, acrylic acid polymer, and carboxyvinyl polymer), carrageenan, cellulosic derivatives (e.g. carboxymethylcellulose sodium, powdered cellulose, hydroxymethyl cellulose, hydroxypropyl cellulose, hydroxypropyl methylcellulose, methylcellulose), sorbitan fatty acid esters (e.g. polyoxyethylene sorbitan monolaurate [Tween 20], polyoxyethylene sorbitan [Tween 60], polyoxyethylene sorbitan monooleate [Tween 80], sorbitan monopalmitate [Span 40], sorbitan monostearate [Span 60], sorbitan tristearate [Span 65], glyceryl monooleate, sorbitan monooleate [Span 80]), polyoxyethylene esters (e.g. polyoxyethylene monostearate [Myrj 45], polyoxyethylene hydrogenated castor oil, polyethoxylated castor oil, polyoxymethylene stearate, and Solutol), sucrose fatty acid esters, polyethylene glycol fatty acid esters (e.g. Cremophor), polyoxyethylene ethers, (e.g. polyoxyethylene lauryl ether [Brij 30]), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic F 68, Poloxamer 188, cetrimonium bromide, cetylpyridinium chloride, benzalkonium chloride, docusate sodium, etc. and/or combinations thereof.

Exemplary binding agents include starch (e.g. cornstarch and starch paste), gelatin, sugars (e.g. sucrose, glucose, dextrose, dextrin, molasses, lactose, lactitol, mannitol, etc.), natural and synthetic gums (e.g. acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum), and larch arabogalactan), alginates, polyethylene oxide, polyethylene glycol, inorganic calcium salts, silicic acid, polymethacrylates, waxes, water, alcohol, etc., and/or combinations thereof.

Exemplary preservatives include antioxidants, chelating agents, antimicrobial preservatives, antifungal preservatives, alcohol preservatives, acidic preservatives, and other preservatives.

Exemplary antioxidants include alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfate, sodium metabisulfite, and sodium sulfite.

Exemplary chelating agents include ethylenediaminetetraacetic acid (EDTA) and salts and hydrates thereof (e.g., sodium edetate, disodium edetate, trisodium edetate, calcium disodium edetate, dipotassium edetate, and the like), citric acid and salts and hydrates thereof (e.g., citric acid monohydrate), fumaric acid and salts and hydrates thereof, malic acid and salts and hydrates thereof, phosphoric acid and salts and hydrates thereof, and tartaric acid and salts and hydrates thereof. Exemplary antimicrobial preservatives include benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal.

Exemplary antifungal preservatives include butyl paraben, methyl paraben, ethyl paraben, propyl paraben, benzoic acid, hydroxybenzoic acid, potassium benzoate, potassium sorbate, sodium benzoate, sodium propionate, and sorbic acid.

Exemplary alcohol preservatives include ethanol, polyethylene glycol, phenol, phenolic compounds, bisphenol, chlorobutanol, hydroxybenzoate, and phenylethyl alcohol.

Exemplary acidic preservatives include vitamin A, vitamin C, vitamin E, beta-carotene, citric acid, acetic acid, dehydroacetic acid, ascorbic acid, sorbic acid, and physic acid.

Other preservatives include tocopherol, tocopherol acetate, deteroxime mesylate, cetrimide, butylated hydroxyanisol (BHA) butylated hydroxytoluened (BHT), ethylenediamine, sodium lauryl sulfate (SLS), sodium lauryl ether sulfate (SLES), sodium bisulfate, sodium metabisulfite, potassium sulfite, potassium metabisulfite, Glydant Plus, Phenonip, methylparaben, German 115, Gertnaben II, Neolone, Kathon, and Euxyl. In certain embodiments, the preservative is an anti-oxidant. In other embodiments, the preservative is a chelating agent.

Exemplary buffering agents include citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, etc., and combinations thereof.

Exemplary lubricating agents include magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, etc., and combinations thereof.

Exemplary natural oils include almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, eucalyptus, evening primrose, fish, flaxseed, geraniol, gourd, grape seed, hazel nut, hyssop, isopropyl myristate, jojoba, kukui nut, lavandin, lavender, lemon, litsea cubeba, macademia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary synthetic oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and combinations thereof.

Additionally, the composition may further comprise a polymer. Exemplary polymers contemplated herein include, but are not limited to, cellulosic polymers and copolymers, for example, cellulose ethers such as methylcellulose (MC), hydroxyethylcellulose (HEC), hydroxypropyl cellulose (HPC), hydroxypropyl methyl cellulose (HPMC), methylhydroxyethylcellulose (MHEC), methyl hydroxypropylcellulose (MHPC), carboxymethyl cellulose (CMC) and its various salts, including, e.g., the sodium salt, hydroxyethylcarboxymethylcellulose (HECMC) and its various salts, carboxymethylhydroxyethylcellulose (CMHEC) and its various salts, other polysaccharides and polysaccharide derivatives such as starch, dextran, dextran derivatives, chitosan, and alginic acid and its various salts, carageenan, various gums, including xanthan gum, guar gum, gum arabic, gum karaya, gum ghatti, konjac and gum tragacanth, glycosaminoglycans and proteoglycans such as hyaluronic acid and its salts, proteins such as gelatin, collagen, albumin, and fibrin, other polymers, for example, polyhydroxyacids such as polylactide, polygtycolide, polyl(lactide-co-glycolide) and poly(.epsilon.-caprolactone-co-glycolide)-, carboxyvinyl polymers and their salts (e.g., carbomer), potyvinylpyrrolidone (PVP), polyacrylic acid and its salts, polyacrylamide, polyacilic acid/acrylamide copolymer, polyalkylene oxides such as polyethylene oxide, polypropylene oxide, poly(ethylene oxide-propylene oxide), and a Plutonic polymer, polyoxyethylene (polyethylene glycol), polyanhydrides, polyvinylalchol, polyethyleneamine and polypyrridine, polyethylene glycol (PEG) polymers, such as PEGylated lipids (e.g., PEG-stearate, 1,2-Distearoyl-sn-glycero-3-Phosphoethanolamine-N-[Methoxy(Polyethylene glycol)-1000], 1,2-Distearoyl-sn-glycero-3-Phosphoethanolamine-N-[Methoxy(Polyethylene glycol)-2000], and 1,2-Distearoyl-sn-glycero-3-Phosphoethanol amine-N-[Methoxy(Polyethylene glycol)-5000]), copolymers and salts thereof.

Additionally, the composition may further comprise an emulsifying agent. Exemplary emulsifying agents include, but are not limited to, a polyethylene glycol (PEG), a polypropylene glycol, a polyvinyl alcohol, a poly-N-vinyl pyrrolidone and copolymers thereof, poloxamer nonionic surfactants, neutral water-soluble polysaccharides (e.g., dextran, Ficoll, celluloses), non-cationic poly(meth)acrylates, non-cationic polyacrylates, such as poly(meth)acrylic acid, and esters amide and hydroxyalkyl amides thereof, natural emulsifiers (e.g. acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g. bentonite [aluminum silicate] and Veegum [magnesium aluminum silicate]), long chain amino acid derivatives, high molecular weight alcohols (e.g. stearyl alcohol, cetyl alcohol, oleyl alcohol, triacetin monostearate, ethylene glycol distearate, glyceryl monostearate, and propylene glycol monostearate, polyvinyl alcohol), carbomers (e.g. carboxy polymethylene, polyacrylic acid, acrylic acid polymer, and carboxyvinyl polymer), carrageenan, cellulosic derivatives (e.g. carboxymethylcellulose sodium, powdered cellulose, hydroxymethyl cellulose, hydroxypropyl cellulose, hydroxypropyl methylcellulose, methylcellulose), sorbitan fatty acid esters polyoxyethylene sorbitan monolaurate [Tween 20], polyoxyethylene sorbitan [Tween 60], polyoxyethylene sorbitan monooleate [Tween 80], sorbitan monopalmitate [Span 40], sorbitan monostearate [Span 60], sorbitan tristearate [Span 65], glyceryl monooleate, sorbitan monooleate [Span 80]), polyoxyethylene esters (e.g. polyoxyethylene monostearate [Myrj 45], polyoxyethylene hydrogenated castor oil, polyethoxylated castor oil, polyoxymethylene stearate, and Solutol), sucrose fatty acid esters, polyethylene glycol fatty acid esters (e.g. Cremophor), polyoxyethylene ethers, (e.g. polyoxyethylene lauryl ether [Brij 30]), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic F 68, Poloxamer 188, cetrimonium bromide, cetylpyridinium chloride, benzalkonium chloride, docusate sodium, etc. and/or combinations thereof. In certain embodiments, the emulsifying agent is cholesterol.

Liquid compositions include emulsions, microemulsions, solutions, suspensions, syrups, and elixirs. In addition to the active compound, the liquid composition may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable compositions, for example, injectable aqueous or oleaginous suspensions may be formulated according to the known art using suitable dispersing or wetting agents and suspending agents. The sterile injectable preparation may also be a injectable solution, suspension, or emulsion in a nontoxic parenterally acceptable diluent or solvent, for example, as a solution in 1,3-butanediol. Among the acceptable vehicles and solvents for pharmaceutical or cosmetic compositions that may be employed are water, Ringer's solution, U.S.P. and isotonic sodium chloride solution. In addition, sterile, fixed oils are conventionally employed as a solvent or suspending medium. Any bland fixed oil can be employed including synthetic mono- or diglycerides. In addition, fatty acids such as oleic acid are used in the preparation of injectables. In certain embodiments, the particles are suspended in a carrier fluid comprising 1% (w/v) sodium carboxymethyl cellulose and 0.1% v/v) Tween 80. The injectable composition can be sterilized, for example, by filtration through a bacteria-retaining filter, or by incorporating sterilizing agents in the form of sterile solid compositions which can be dissolved or dispersed in sterile water or other sterile injectable medium prior to use.

Compositions for rectal or vaginal administration may be in the form of suppositories which can be prepared by mixing the particles with suitable non-irritating excipients or carriers such as cocoa butter, polyethylene glycol, or a suppository wax which are solid at ambient temperature but liquid at body temperature and therefore melt in the rectum or vaginal cavity and release the particles.

Solid compositions include capsules, tablets, pills, powders, and granules. In such solid compositions, the particles are mixed with at least one excipient and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets, and pills, the dosage form may also comprise buffering agents. Solid compositions of a similar type may also be employed as fillers in soft and hard-filled gelatin capsules using such excipients as lactose or milk sugar as well as high molecular weight polyethylene glycols and the like.

Tablets, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

Solid compositions of a similar type may also be employed as fillers in soft and hard-filled gelatin capsules using such excipients as lactose or milk sugar as well as high molecular weight polyethylene glycols and the like.

Compositions for topical or transdermal administration include ointments, pastes, creams, lotions, gels, powders, solutions, sprays, inhalants, or patches. The active compound is admixed with an excipient and any needed preservatives or buffers as may be required. Ophthalmic formulation, ear drops, and eye drops are also contemplated as being within the scope of this invention.

The ointments, pastes, creams, and gels may contain, in addition to the active compound, excipients such as animal and vegetable fats, oils, waxes, paraffins, starch, tragacanth, cellulose derivatives, polyethylene glycols, silicones, bentonites, silicic acid, talc, and zinc oxide, or mixtures thereof.

Powders and sprays can contain, in addition to the active compound, excipients such as lactose, talc, silicic acid, aluminum hydroxide, calcium silicates, and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the nanoparticles in a proper medium. Absorption enhancers can also be used to increase the flux of the compound across the skin. The rate can be controlled by either providing a rate controlling membrane or by dispersing the particles in a polymer matrix or gel.

Agents

Agents to be delivered by the systems described herein may be therapeutic, diagnostic, or prophylactic agents. Any chemical compound to be administered to a subject may be delivered using the particles or nanoparticles described herein. The agent may be an organic molecule (e.g., a therapeutic agent, a drug), inorganic molecule, nucleic acid, protein, amino acid, peptide, polypeptide, polynucleotide, targeting agent, isotopically labeled organic or inorganic molecule, vaccine, immunological agent, etc.

In certain embodiments, the agents are organic molecules with pharmaceutical activity, e.g., a drug. In certain embodiments, the drug is an antibiotic, anti-viral agent, anesthetic, steroidal agent, anti-inflammatory agent, anti-neoplastic agent, anti-cancer agent, antigen, vaccine, antibody, decongestant, antihypertensive, sedative, birth control agent, progestational agent, anti-cholinergic, analgesic, anti-depressant, anti-psychotic, f3-adrenergic blocking agent, diuretic, cardiovascular active agent, vasoactive agent, non-steroidal anti-inflammatory agent, nutritional agent, etc.

In certain embodiments of the present invention, the agent to be delivered may be a mixture of agents.

Diagnostic agents include gases; metals; commercially available imaging agents used in positron emissions tomography (PET), computer assisted tomography (CAT), single photon emission computerized tomography, x-ray, fluoroscopy, and magnetic resonance imaging (MRI); and contrast agents. Examples of suitable materials for use as contrast agents in MRI include gadolinium chelates, as well as iron, magnesium, manganese, copper, and chromium. Examples of materials useful for CAT and x-ray imaging include iodine-based materials.

Therapeutic and prophylactic agents include, but are not limited to, antibiotics, nutritional supplements, and vaccines. Vaccines may comprise isolated proteins or peptides, inactivated organisms and viruses, dead organisms and viruses, genetically altered organisms or viruses, and cell extracts. Therapeutic and prophylactic agents may be combined with interleukins, interferon, cytokines, and adjuvants such as cholera toxin, alum, Freund's adjuvant, etc. Prophylactic agents include antigens of such bacterial organisms as *Streptococccus pneumoniae, Haemophilus influenzae, Staphylococcus aureus, Streptococcus pyrogenes, Corynebacterium diphtheriae, Listeria monocytogenes, Bacillus anthracis, Clostridium tetani, Clostridium botulinum, Clostridium perfringens, Neisseria meningitidis, Neisseria gonorrhoeae, Streptococcus mutants, Pseudomonas aeruginosa, Salmonella typhi, Haemophilus parainfluenzae, Bordetella pertussis, Francisella tularensis, Yersinia pestis, Vibrio cholerae, Legionella pneumophila, Mycobacterium tuberculosis, Mycobacterium leprae, Treponema pallidum, Leptospirosis interrogans, Borrelia burgdorferi, Camphylobacter jejuni*, and the like; antigens of such viruses as smallpox, influenza A and B, respiratory syncytial virus, parainfluenza, measles, HIV, varicella-zoster, herpes simplex 1 and 2, cytomegalovirus, Epstein-Barr virus, rotavirus, rhinovirus, adenovirus, papillomavirus, poliovirus, mumps, rabies, rubella, coxsackieviruses, equine encephalitis, Japanese encephalitis, yellow fever, Rift Valley fever, hepatitis A, B, C, D, and E virus, and the like; antigens of fungal, protozoan, and parasitic organisms such as *Cryptococcus neoformans, Histoplasma capsulatum, Candida albicans, Candida tropicalis, Nocardia asieroides, Rickettsia ricketsii, Rickettsia typhi, Mycoplasma pneumoniae, Chlamydial psit-* taci, Chlamydial trachomatis, Plasmodium falciparum, Topanosoma brucei, Entamoeba histolytica, Toxoplasma gondii, Trichomonas vaginalis, Schistosoma mansoni, and the like. These antigens may be in the form of whole killed organisms, peptides, proteins, glycoproteins, carbohydrates, or combinations thereof.

In certain embodiments, the the agent is a small molecule, organometallic compound, nucleic acid, protein, peptide, polynucleotide, metal, targeting agent, an isotopically labeled chemical compound, drug, vaccine, immunological agent, or an agent useful in bioprocessing. In certain embodiments, the agent is a polynucleotide. In certain embodiments, the polynucleotide is DNA or RNA. In certain embodiments, the RNA is RNAi, dsRNA, siRNA, shRNA, miRINA, or antisense RNA. In certain embodiments, the polynucleotide and the one or more active compounds are not covalently attached. In one embodiment, the agent is an RNA. In one embodiment, the agent is an mRNA.

Genetic Diseases and Methods of Treatment

It is estimated that over 10,000 human diseases are caused by genetic disorders, which are abnormalities in genes or chromosomes. See, e.g., McClellan, J. and M. C. King, *Genetic heterogeneity in human disease*. Cell 141(2): p. 210-7; Leachman, S. A., et al., *Therapeutic siRNAs for dominant genetic skin disorders including pachyonychia congenita*, J Dermatol Sci, 2008. 51(3): p. 151-7. Many of these diseases are fatal, such as cancer, severe hypercholesterolemia, and familial amyloidotic polyneuropathy. See, e.g., Frank-Kamenetsky, M., et al., *Therapeutic RNAi targeting PCSK9 acutely lowers plasma cholesterol in rodents and LDL, cholesterol in nonhuman primates*. Proc Natl Acad Sci USA, 2008. 105(33): p. 11915-20; Coelho, T., *Familial amyloid polyneuropathy: new developments in genetics and treatment*. Curr Opin Neurol, 1996, 9(5): p. 355-9. Since the discovery of gene expression silencing via RNA interference (RNAi) by Fire and Mello (Fire, A., et al., *Potent and specific genetic interference by double-stranded RNA in Caenorhabditis elegans*. Nature, 1998. 391(6669): p. 806-11), there has been extensive effort toward developing therapeutic Applications for RNAi in humans, See, e.g., Davis, M. E., *The first targeted delivery of siRNA in humans via a self-assembling, cyclodextrin polymer-based nanoparticle: from concept to clinic*. Mol Pharm, 2009. 6(3): p. 659-68; Whitehead, K. A., R. Langer, and D. G. Anderson, *Knocking down barriers: advances in siRNA delivery*. Nat. Rev. Drug Discovery, 2009. 8(2): p. 129-138; Tan, S. J., et al., *Engineering Nanocarriers for siRNA Delivery*. Small 7(7): p. 841-56; Castanotto, D. and J. J. Rossi, *The promises and pitfalls of RNA-interference-based therapeutics*. Nature, 2009. 457(7228): p. 426-33; Chen, Y. and L. Huang, *Tumor-targeted delivery of siRNA by non-viral vector: safe and effective cancer therapy*. Expert Opin Drug Deliv, 2008, 5(12): p. 1301-11; Weinstein, S, and D. Peer, *RNAi nanomedicines: challenges and opportunities within the immune system*. Nanotechnology. 21(23): p. 232001; Fenske, D. B. and P. R. Cullis, *Liposomal nanomedicines*. Expert Opin Drug Deliv, 2008. 5(1): p. 25-44; and Thiel, K. W. and P. H. Giangrande, *Therapeutic Applications of DNA and RNA aptamers*. Oligonucleotides, 2009. 19(3): p. 209-22. Currently, there are more than 20 clinical trials ongoing or completed involving siRNA therapeutics, which have shown promising results for the treatment of various diseases. See, e.g., Burnett, J. C., J. J. Rossi, and K. Tiemann, *Current progress of siRNA/shRNA therapeutics in clinical trials*. Biotechnol J. 6(9): p. 1130-46. However, the efficient and safe delivery of siRNA is still a key challenge in the development of siRNA therapeutics. See, e.g., Juliano, R., et al., *Biological barriers to therapy with antisense and siRNA oligonucleotides*. Mol Pharm, 2009. 6(3): p. 686-95.

Thus, in another aspect, provided are methods of using active compounds, e.g., for the treatment of a disease, disorder or condition from which a subject suffers. It is contemplated that active compounds will be useful in the treatment of a variety of diseases, disorders, or conditions, especially a system for delivering agents useful in the treatment of that particular disease, disorder, or condition, "Disease," "disorder," and "condition" are used interchangeably herein. In certain embodiments, the disease, disorder or condition from which a subject suffers is caused by an abnormality in a gene or chromosome of the subject.

For example, in one embodiment, provided is a method of treating disease, disorder, or condition from which a subject suffers, comprising administering to a subject in need thereof an effective amount of a composition comprising an active compound, or salt thereof. Exemplary disease, disorder, or conditions contemplated include, but are not limited to, proliferative disorders, inflammatory disorders, autoimmune disorders, painful conditions, liver diseases, and amyloid neuropathies.

As used herein, an "active ingredient" is any agent which elicits the desired biological response. For example, the active compound may be the active ingredient in the composition. Other agents, e.g., therapeutic agents, as described herein may also be classified as an active ingredient. In certain embodiments, the composition further comprises, in addition to the active compound, a therapeutic agent useful in treating the disease, disorder, or condition. In certain embodiments, the active compound encapsulates the other (therapeutic) agent. In certain embodiments, the active compound and the other (therapeutic) agent form a particle (e.g., a nanoparticle).

In certain embodiments, the condition is a proliferative disorder and, in certain embodiments, the composition further includes an anti-cancer agent. Exemplary proliferative diseases include, but are not limited to, tumors, begnin neoplasms, pre-malignant neoplasms (carcinoma in situ), and malignant neoplasms (cancers).

Exemplary cancers include, but are not limited to, acoustic neuroma, adenocarcinoma, adrenal gland cancer, anal cancer, angiosarcoma (e.g., lymphangiosarcoma, lymphangioendotheliosarcoma, hemangiosarcoma), appendix cancer, benign monoclonal gatnmopathy, biliary cancer (e.g., cholangiocarcinoma), bladder cancer, breast cancer (e.g., adenocarcinoma of the breast, papillary carcinoma of the breast, mammary cancer, medullary carcinoma of the breast), brain cancer (e.g., meningioma; glioma, e.g., astrocytoma, oligodendroglioma; medulloblastoma), bronchus cancer, carcinoid tumor, cervical cancer (e.g., cervical adenocarcinoma), choriocarcinoma, chordoma, craniopharyngioma, colorectal cancer (e.g., colon cancer, rectal cancer, colorectal adenocarcinoma), epithelial carcinoma, ependymoma, endotheliosarcoma (e.g., Kaposi's sarcoma, multiple idiopathic hemorrhagic sarcoma), endometrial cancer (e.g., uterine cancer, uterine sarcoma), esophageal cancer adenocarcinoma of the esophagus, Barrett's adenocarinoma), Ewing's sarcoma, eye cancer (e.g., intraocular melanoma, retinoblastoma), familiar hypereosinophilia, gall bladder cancer, gastric cancer (e.g., stomach adenocarcinoma), gastrointestinal stromal tumor (GIST), head and neck cancer (e.g., head and neck squamous cell carcinoma, oral cancer (e.g., oral squamous cell carcinoma (OSCC), throat cancer (e.g., laryngeal cancer, pharyngeal cancer, nasopharyngeal cancer, oropharyngeal cancer)), hematopoietic cancers (e.g., leukemia such as acute lymphocytic leukemia (ALL) (e.g., B-cell ALL, T-cell ALL), acute myelocytic leukemia (AML) (e.g., B-cell AML, T-cell AML), chronic myelocytic leukemia (CML) (e.g., B-cell CML, T-cell CML), and chronic lymphocytic leukemia (CLL) (e.g., B-cell CLL, T-cell CLL); lymphoma such as Hodgkin lymphoma (HL) (e.g., B-cell HL) and non-Hodgkin lymphoma (NHL) (e.g., B-cell NHL such as diffuse large cell lymphoma (DLCL) (e.g., diffuse large B-cell lymphoma (DLBCL)), follicular lymphoma, chronic lymphocytic leukemia/small lymphocytic lymphoma (CLL/SLL), mantle cell lymphoma (MCL), marginal zone B-cell lymphomas (e.g., mucosa-associated lymphoid tissue (MALT) lymphomas, nodal marginal zone B-cell lymphoma, splenic marginal zone B-cell lymphoma), primary mediastinal B-cell lymphoma, Burkitt lymphoma, lymphoplasmacytic lymphoma (i.e., "Waldenstrom's macroglobulinemia"), hairy cell leukemia (HCL), immunoblastic large cell lymphoma, precursor B-lymphoblastic lymphoma and primary central nervous system (CNS) lymphoma; and T-cell NHL such as precursor T-lymphoblastic lymphomalleukemia, peripheral T-cell lymphoma (PTCL) (e.g., cutaneous T-cell lymphoma (CTCL) (e.g., mycosis fungiodes, Sezary syndrome), angioimmunoblastic T-cell lymphoma, extranodal natural killer T-cell lymphoma, enteropathy type T-cell lymphoma, subcutaneous panniculitis-like T-cell lymphoma, anaplastic large cell lymphoma); a mixture of one or more leukemia/lymphoma as described above; and multiple myeloma (MM)), heavy chain disease (e.g., alpha chain disease, gamma chain disease, mu chain disease), hemangioblastoma, inflammatory myofibroblastic tumors, immunocytic amyloidosis, kidney cancer (e.g., nephroblastoma Wilms' tumor, renal cell carcinoma), liver cancer (e.g., hepatocellular cancer (HCC), malignant hepatoma), lung cancer (e.g., bronchogenic carcinoma, small cell lung cancer (SCLC), non-small cell lung cancer (NSCLC), adenocarcinoma of the lung), leiomyosarcoma (LMS), mastocytosis (e.g., systemic mastocytosis), myelodysplastic syndrome (MDS), mesothelioma, myeloproliferative disorder (MPD) (e.g., polycythemia Vera (PV), essential thrombocytosis (ET), agnogenic myeloid metaplasia (AMM) a.k.a. myelofibrosis (MF), chronic idiopathic myelofibrosis, chronic myelocytic leukemia (CML), chronic neutrophilic leukemia (CNL), hypereosinophilic syndrome (HES)), neuroblastoma, neurofibroma (e.g., neurofibromatosis (NF) type 1 or type 2, schwannomatosis neuroendocrine cancer (e.g., gastroenteropancreatic neuroendoctrine tumor (GEP-NET), carcinoid tumor), osteosarcoma, ovarian cancer (e.g., cystadenocarcinoma, ovarian embryonal carcinoma, ovarian adenocarcinoma), papillary adenocarcinoma, pancreatic cancer (e.g., pancreatic andenocarcinoma, intraductal papillary mucinous neoplasm (IPMN), Islet cell tumors), penile cancer (e.g., Paget's disease of the penis and scrotum), pinealoma, primitive neuroectodermal tumor (PNT), prostate cancer (e.g., prostate adenocarcinoma), rectal cancer, rhabdomyosarcoma, salivary gland cancer, skin cancer (e.g., squamous cell carcinoma (SCC), keratoacanthoma (KA), melanoma, basal cell carcinoma (BCC)), small bowel cancer (e.g., appendix cancer), soft tissue sarcoma (e.g., malignant fibrous histiocytoma (MFH), liposarcoma, malignant peripheral nerve sheath tumor (MPNST), chondrosarcoma, fibrosarcoma, myxosarcoma), sebaceous gland carcinoma, sweat gland carcinoma, synovioma, testicular cancer (e.g., seminoma, testicular embryonal carcinoma), thyroid cancer (e.g., papillary carcinoma of the thyroid, papillary thyroid carcinoma (PTC), medullary thyroid cancer), urethral cancer, vaginal cancer and vulvar cancer (e.g., Paget's disease of the vulva).

Anti-cancer agents encompass biotherapeutic anti-cancer agents as well as chemotherapeutic agents.

Exemplary biotherapeutic anti-cancer agents include, but are not limited to, interferons, cytokines (e.g., tumor necrosis factor, interferon α, interferon γ), vaccines, hematopoietic growth factors, monoclonal serotherapy, immunostimulants and/or imtnunodulatory agents (e.g., IL-1, 2, 4, 6, or 12), immune cell growth factors (e.g., GM-CSF) and antibodies (e.g. HERCEPTIN (trastuzumab), T-DM1, AVASTIN (bevacizumab), ERBITUX (cetuximab), VECTIBIX (panitumumab), RITUXAN (rituximab), BEXXAR (tositumomab)).

Exemplary chemotherapeutic agents include, but are not limited to, anti-estrogens (e.g. tamoxifen, raloxifene, and megestrol), LHRH agonists (e.g. goscrelin and leuprolide), anti-androgens (e.g., flutamide and bicalutamide), photodynamic therapies (e.g. vertoporfin (BPD-MA), phthalocyanine, photosensitizer Pc4, and demethoxy-hypocrellin A (2BA-2-DMHA)), nitrogen mustards (e.g. cyclophosphamide, ifosfamide, trofosfamide, chlorambucil, estramustine, and melphalan), nitrosoureas (e.g. carmustine (BCNU) and lomustine (CCNU)), alkylsulphonates busulfan and treosulfan), triazenes dacarbazine, temozolomide), platinum containing compounds (e.g. cisplatin, carboplatin, oxaliplatin), vinca alkaloids (e.g. vincristine, vinblastine, vindesine, and vinorelbine), taxoids (e.g. paclitaxel or a paclitaxel equivalent such as nanoparticle albumin-bound paclitaxel (ABRAXANE), docosahexaenoic acid bound-paclitaxel (DHA-paclitaxel, Taxoprexin), polyglutamate bound-paclitaxel (PG-paclitaxel, paclitaxel poliglumex, CT-2103, XYOTAX), the tumor-activated prodrug (TAP) ANG1005 (Angiopep-2 bound to three molecules of paclitaxel), paclitaxel-EC-1 (paclitaxel bound to the erbB2-recognizing peptide EC-1), and glucose-conjugated paclitaxel, e.g., 2'-paclitaxel methyl 2-glucopyranosyl succinate; docetaxel, taxol), epipodophyllins (e.g. etoposide, etoposide phosphate, teniposide, topotecan, 9-aminocamptothecin, camptoirinotecan, irinotecan, crisnatol, mytomycin C), anti-metabolites, DHFR inhibitors (e.g. methotrexate, dichloromethotrexate, trimetrexate, edatrexate), IMP dehydrogenase inhibitors (e.g. mycophenolic acid, tiazofurin, ribavirin, and EICAR), ribonucleotide reductase inhibitors (e.g. hydroxyurea and deferoxamine), uracil analogs (e.g. 5-fluorouracil (5-FU), floxuridine, doxifluridine, ratitrexed, tegafur-uracil, capecitabine), cytosine analogs (e.g. cytarabine (ara C), cytosine arabinoside, and fludarabine), purine analogs (e.g. mercaptopurine and Thioguanine), Vitamin D3 analogs (e.g. EB 1089, CB 1093, and KH 1060), isoprenylation inhibitors (e.g. lovastatin), dopaminergic neurotoxins 1-methyl-4-phenylpyridinium ion), cell cycle inhibitors (e.g. staurosporine), actinomycin (e.g. actinotnycin D, dactinomycin), bleomycin (e.g. bleomycin A2, bleomycin B2, peplomycin), anthracycline (e.g. daunorubicin, doxorubicin, pegylated liposomal doxonthicin, idarubicin, epirubicin, pirarubicin, zorubicin, mitoxantrone), MDR inhibitors (e.g. verapamil), $Ca^{2+}$ ATPase inhibitors (e.g. thapsigargin), imatinib, thalidomide, lenalidomide, tyrosine kinase inhibitors (e.g., axitinib (AG013736), bosutinib (SKI-606), cediranib (RECENTIN™, AZD2171), dasatinib (SPRYCEL®, BMS-354825), erlotinib (TARCEVA®), gefitinib (IRESSA®), imatinib (Gleevec®, CGP57148B, STI-571), lapatinib (TYKEKB®, TYVVERB®), lestaurtinib (CEP-701), neratinib (HKI-272), nilotinib (TASIGNA®), semaxanib (semaxinib, SU5416), sunitinib (SUTENT®, SU11248), toceranib (PALLADIA®), vandetanib (ZACTIMA®, ZD6474), vatalanib (PTK787, PTK/ZK), trastuzumab (HERCEPTIN®), bevacizumab (AVASTIN®), rituximab (RITUXAN®), cetuximab (ERBITUX®), panitumumab (VECTIBIX®), ranibizumab (Lucentis®), nilotinib (TASIGNA®), sorafenib (NEXAVAR®), everolimus (AFINITOR®), alemtuzumab (CAMPATH®), gemtuzumab ozogamicin (MYLOTARG®), temsirolimus (TORISEL®), ENMD-2076, PCI-32765, AC220, dovitinib lactate (TK1258, CHIR-258), BIBW 2992 (TOVOK™), SGX523, PF-04217903, PF-02341066, PF-299804, BMS-777607, ABT-869, MP470, BIBF 1120 (VARGATEF®), AP24534, JNJ-26483327, MGCD265, DCC-2036, BMS-690154, CEP-11981, tivozanib (AV-951), OSI-930, MM-121, XL-184, XL-647, and/or XL228), proteasome inhibitors (e.g., bortezomib (VELCADE)), mTOR inhibitors (e.g., rapamycin, temsirolimus (CCI-779), everolimus (RAD-001), ridaforolimus, AP23573 (Ariad), AZD8055 (AstraZeneca), BEZ235 (Novartis), BGT226 (Norvartis), XL765 (Sanofi Aventis), PF-4691502 (Pfizer). GDC0980 (Genetech), SF1126 (Semafoe) and OSI-027 (OSI)), oblimersen, gemcitabine, caminomycin, leucovorin, pemetrexed, cyclophosphamide, dacarbazine, procarbizine, prednisolone, dexamethasone, campathecin, plicamycin, asparaginase, aminopterin, methopterin, porfiromycin, melphalan, leurosidine, leurosine, chlorambucil, trabectedin, procarbazine, discodermolide, catninotnycin, aminopterin, and hexamethyl melamine.

In certain embodiments, the condition is an inflammatory disorder and, in certain embodiments, the composition further includes an anti-inflammatory agent. The term "inflammatory disorder" refers to those diseases, disorders or conditions that are characterized by signs of pain (dolor, from the generation of noxious substances and the stimulation of nerves), heat (calor, from vasodilatation), redness (rubor, from vasodilatation and increased blood flow), swelling (tumor, from excessive inflow or restricted outflow of fluid), and/or loss of function (functio laesa, which can be partial or complete, temporary or permanent. Inflammation takes on many forms and includes, but is not limited to, acute, adhesive, atrophic, catarrhal, chronic, cirrhotic, diffuse, disseminated, exudative, fibrinous, fibrosing, focal, granulomatous, hyperplastic, hypertrophic, interstitial, metastatic, necrotic, obliterative, parenchymatous, plastic, productive, proliferous, pseudomembranous, purulent, sclerosing, seroplastic, serous, simple, specific, subacute, suppurative, toxic, traumatic, and/or ulcerative inflammation.

Exemplary inflammatory disorders include, but are not limited to, inflammation associated with acne, anemia (e.g., aplastic anemia, haemolytic autoimmune anaemia), asthma, arteritis (e.g., polyarteritis, temporal arteritis, periarteritis nodosa, Takayasu's arteritis), arthritis (e.g., crystalline arthritis, osteoarthritis, psoriatic arthritis, gouty arthritis, reactive arthritis, rheumatoid arthritis and Reiter's arthritis), ankylosing spondylitis, amylosis, amyotrophic lateral sclerosis, autoimmune diseases, allergies or allergic reactions, atherosclerosis, bronchitis, bursitis, chronic prostatitis, conjunctivitis, Chagas disease, chronic obstructive pulmonary disease, cermatomyositis, diverticulitis, diabetes (e.g., type 1 diabetes mellitus, type 2 diabetes mellitus), a skin condition (e.g., psoriasis, eczema, burns, dermatitis, pruritus (itch)), endometriosis, Guillain-Barre syndrome, infection, ischaemic heart disease, Kawasaki disease, glomerulonephritis, gingivitis, hypersensitivity, headaches (e.g., migraine headaches, tension headaches), ileus (e.g., postoperative ileus and ileus during sepsis), idiopathic thrombocytopenic purpura, interstitial cystitis (painful bladder syndrome), gastrointestinal disorder (e.g., selected from peptic ulcers, regional enteritis, diverticulitis, gastrointestinal bleeding, eosinophilic gastrointestinal disorders (e.g., eosinophilic esophagitis, eosinophilic gastritis, eosinophilic gastroenteritis, eosinophilic colitis), gastritis, diarrhea, gastroesophageal reflux disease (GORD, or its synonym GERD), inflammatory bowel disease (IBD) (e.g., Crohn's disease, ulcerative colitis, collagenous colitis, lymphocytic colitis, ischaemic colitis, diversion colitis, Behcet's syndrome, indeterminate colitis) and inflammatory bowel syndrome (IBS)), lupus, multiple sclerosis, morphea, myeasthenia gravis, myocardial ischemia, nephrotic syndrome, pemphigus vulgaris, pernicious aneaemia, peptic ulcers, polymyositis, primary biliary cirrhosis, neuroinflammation associated with brain disorders (e.g., Parkinson's disease, Huntington's disease, and Alzheimer's disease), prostatitis, chronic inflammation associated with cranial radiation injury, pelvic inflammatory disease, reperfusion injury, regional enteritis, rheumatic fever, systemic lupus erythematosus, schleroderma, scierodoma, sarcoidosis, spondyloarthopathies, Sjogren's syndrome, thyroiditis, transplantation rejection, tendonitis, trauma or injury (e.g., frostbite, chemical irritants, toxins, scarring, burns, physical injury), vasculitis, vitiligo and Wegener's granulomatosis.

In certain embodiments, the inflammatory disorder is inflammation associated with a proliferative disorder, e.g., inflammation associated with cancer.

In certain embodiments, the condition is an autoimmune disorder and, in certain embodiments, the composition further includes an immunomodulatory agent. Exemplary autoimmune disorders include, but are not limited to, arthritis (including rheumatoid arthritis, spondyloarthopathies, gouty arthritis, degenerative joint diseases such as osteoarthritis, systemic lupus erythematosus, Sjogren's syndrome, ankylosing spondylitis, undifferentiated spondylitis, Behcet's disease, haemolytic autoimmune anaemias, multiple sclerosis, amyotrophic lateral sclerosis, amylosis, acute painful shoulder, psoriatic, and juvenile arthritis), asthma, atherosclerosis, osteoporosis, bronchitis, tendonitis, bursitis, skin condition (e.g., psoriasis, eczema, burns, dermatitis, pruritus (itch)), enuresis, eosinophilic disease, gastrointestinal disorder (e.g., selected from peptic ulcers, regional enteritis, diverticulitis, gastrointestinal bleeding, eosinophilic gastrointestinal disorders (e.g., eosinophilic esophagitis, eosinophilic gastritis, eosinophilic gastroenteritis, eosinophilic colitis), gastritis, diarrhea, gastroesophageal reflux disease (GORD, or its synonym GERD), inflammatory bowel disease (IBD) (e.g., Crohn's disease, ulcerative colitis, collagenous colitis, lymphocytic colitis, ischaemic colitis, diversion colitis, Behcet's syndrome, indeterminate colitis) and inflammatory bowel syndrome (IBS)), and disorders ameliorated by a gastroprokinetic agent (e.g., ileus, postoperative ileus and ileus during sepsis; gastroesophageal reflux disease (GORD, or its synonym GERD); eosinophilic esophagitis, gastroparesis such as diabetic gastroparesis; food intolerances and food allergies and other functional bowel disorders, such as non-ulcerative dyspepsia (NUD) and non-cardiac chest pain (NCCP, including costo-chondritis)).

In certain embodiments, the condition is a painful condition and, in certain embodiments, the composition further includes an analgesic agent. A "painful condition" includes, but is not limited to, neuropathic pain (e.g., peripheral neuropathic pain), central pain, deafferentiation pain, chronic pain (e.g., chronic nociceptive pain, and other forms of chronic pain such as post-operative pain, e.g., pain arising after hip, knee, or other replacement surgery), pre-operative pain, stimulus of nociceptive receptors (nociceptive pain), acute pain (e.g., phantom and transient acute pain), noninflammatory pain, inflammatory pain, pain associated with cancer, wound pain, burn pain, postoperative pain, pain associated with medical procedures, pain resulting from pruritus, painful bladder syndrome, pain associated with premenstrual dysphoric disorder and/or premenstrual syndrome, pain associated with chronic fatigue syndrome, pain associated with pre-term labor, pain associated with drawl symptoms from drug addiction, joint pain, arthritic pain (e.g., pain associated with crystalline arthritis, osteoarthritis, psoriatic arthritis, gouty arthritis, reactive arthritis, rheumatoid arthritis or Reiter's arthritis), lumbosacral pain, musculo-skeletal pain, headache, migraine, muscle ache, lower back pain, neck pain, toothache, dental/maxillofacial pain, visceral pain and the like. One or more of the painful conditions contemplated herein can comprise mixtures of various types of pain provided above and herein (e.g. nociceptive pain, inflammatory pain, neuropathic pain, etc.). In some embodiments, a particular pain can dominate. In other embodiments, the painful condition comprises two or more types of pains without one dominating. A skilled clinician can determine the dosage to achieve a therapeutically effective amount for a particular subject based on the painful condition.

In certain embodiments, the painful condition is inflammatory pain. In certain embodiments, the painful condition (e.g., inflammatory pain) is associated with an inflammatory disorder and/or an autoimmune disorder.

In certain embodiments, the condition is a liver disease and, in certain embodiments, the composition further includes an agent useful in treating liver disease. Exemplary liver diseases include, but are not limited to, drug-induced liver injury (e.g., acetaminophen-induced liver injury), hepatitis (e.g., chronic hepatitis, viral hepatitis, alcohol-induced hepatitis, autoimmune hepatitis, steatohepatitis), non-alcoholic fatty liver disease, alcohol-induced liver disease (e.g., alcoholic fatty liver, alcoholic hepatitis, alcohol-related cirrhosis), hypercholesterolemia (e.g., severe hypercholesterolemia), transthyretin-related hereditary amyloidosis, liver cirrhosis, liver cancer, primary biliary cirrhosis, cholestatis, cystic disease of the liver, and primary sclerosing cholangitis. In certain embodiments the liver disease is associated with inflammation.

In certain embodiments, the condition is a familial amyloid neuropathy and, in certain embodiments, the composition further includes an agent useful in a familial amyloid neuropathy.

The active ingredient may be administered in such amounts, time, and route deemed necessary in order to achieve the desired result. The exact amount of the active ingredient will vary from subject to subject, depending on the species, age, and general condition of the subject, the severity of the infection, the particular active ingredient, its mode of administration, its mode of activity, and the like. The active ingredient, whether the active compound itself, or the active compound in combination with an agent, is preferably formulated in dosage unit form for ease of administration and uniformity of dosage. It will be understood, however, that the total daily usage of the active ingredient will be decided by the attending physician within the scope of sound medical judgment. The specific therapeutically effective dose level for any particular subject will depend upon a variety of factors including the disorder being treated and the severity of the disorder; the activity of the active ingredient employed; the specific composition employed; the age, body weight, general health, sex and diet of the patient; the time of administration, route of administration, and rate of excretion of the specific active ingredient employed; the duration of the treatment; drugs used in combination or coincidental with the specific active ingredient employed; and like factors well known in the medical arts.

The active ingredient may be administered by any route. In some embodiments, the active ingredient is administered via a variety of routes, including oral, intravenous, intramuscular, intra-arterial, intramedullary, intrathecal, subcutaneous, intraventricular, transdermal, interdermal, rectal, intravaginal, intraperitoneal, topical (as by powders, ointments, creams, and/or drops), mucosal, nasal, bucal, enteral, sublingual; by intratracheal instillation, bronchial instillation, and/or inhalation; and/or as an oral spray, nasal spray, and/or aerosol. In general the most appropriate route of administration will depend upon a variety of factors including the nature of the active ingredient (e.g., its stability in the environment of the gastrointestinal tract), the condition of the subject (e.g., whether the subject is able to tolerate oral administration), etc.

The exact amount of an active ingredient required to achieve a therapeutically or prophylactically effective amount will vary from subject to subject, depending on species, age, and general condition of a subject, severity of the side effects or disorder, identity of the particular compound(s), mode of administration, and the like. The amount to be administered to, for example, a child or an adolescent can be determined by a medical practitioner or person skilled in the art and can be lower or the same as that administered to an adult.

Methods

In one aspect, provided herein is a method for the delivery of an agent (for example, a polynucleotide) into a cell comprising;

introducing into the cell a composition comprising;

i) a nanoparticle comprising;
    a compound of Formula I, II, III, IV, or V;
    a non-cationic lipid;
    a polyethylene glycol-lipid;
    a sterol; and
ii) an agent.

In one embodiment, the agent is a therapeutic agent. In one embodiment, the agent is a diagnostic agent.

In one embodiment, the agent delivered into cells can be a polynucleotide. Polynucleotides or oligonucleotides that can be introduced according to the invention methods include DNA, cDNA, and RNA sequences of all types. For example, the polynucleotide can be double stranded DNA, single-stranded DNA, complexed DNA, encapsulated DNA, naked RNA, encapsulated RNA, messenger RNA (mRNA), tRNA, short interfering RNA (siRNA), double stranded RNA (dsRNA), micro-RNA (miRNA), antisense RNA (as-RNA) and combinations thereof. The polynucleotides can also be DNA constructs, such as expression vectors, expression vectors encoding a desired gene product (e.g., a gene product homologous or heterologous to the subject into which it is to be introduced), and the like. In one embodiment, the agent is an mRNA.

In one embodiment, the cell is a mammalian cell. In one embodiment, the cell is a human cell. In one embodiment, the cell is a liver cell. In one embodiment, the cell is a blood cell.

In some embodiments, provided herein are methods for delivery polynucleotides (for example, mRNA) to correct a mutation in a genome. For example, mRNAs can be delivered to correct mutations that cause hemophilia (due to mutations in the genes encoding Factor VIII (FS; hemophilia A) or Factor IX (F9; hemoglobin B).

In one aspect of the invention, disclosed herein is a method of treating hemophilia in a subject comprising:
i) administering a composition to the subject, wherein the composition comprises:
a nanoparticle comprising;
  a compound of Formula I, II, III, IV, or V;
  a non-cationic lipid;
  a polyethylene glycol-lipid;
  a sterol; and
an agent;
and
ii) introducing the agent into the cell of the subject, wherein the agent comprises:
a) a guide RNA that hybridizes with a target sequence of a DNA molecule in a eukaryotic cell that contains the DNA molecule,
b) an mRNA encoding a Cpf1 protein, and
c) an isolated nucleic acid comprising a donor sequence comprising a nucleic acid encoding a truncated FM polypeptide;
wherein the cell of the subject contains a genetic mutation in the F8 gene;
wherein the guide RNA hybridizes with the target sequence,
wherein the target sequence is in the F8 gene,
wherein the Cpf1 protein creates a double stranded break in the DNA molecule,
wherein the nucleic acid encoding the truncated FVIII polypeptide is flanked by nucleic acid sequences homologous to the nucleic acid sequences upstream and downstream of the double stranded break in the DNA molecule, and
wherein the resultant repaired gene, upon expression, confers improved coagulation functionality to the encoded FVIII protein of the subject compared to the non-repaired F8 gene.

In one aspect of the invention, disclosed herein is a method of treating hemophilia in a subject comprising:
i) administering a composition to the subject, wherein the composition comprises:
a nanoparticle comprising;
  a compound of Formula I, II, III, IV, or V;
  a non-cationic lipid;
  a polyethylene glycol-lipid;
  a sterol; and
an agent;
and
ii) introducing the agent into the cell of the subject, wherein the agent comprises:
a) a guide RNA that hybridizes with a target sequence of a DNA molecule in a eukaryotic cell that contains the DNA molecule,
b) an mRNA encoding a Cpf1 protein, and
c) an isolated nucleic acid comprising a donor sequence comprising a nucleic acid encoding a truncated FIX polypeptide;
wherein the cell of the subject contains a genetic mutation in the F9 gene;
wherein the guide RNA hybridizes with the target sequence,
wherein the target sequence is in the F9 gene,
wherein the Cpf1 protein creates a double stranded break in the DNA molecule,
wherein the nucleic acid encoding the truncated FVIII polypeptide is flanked by nucleic acid sequences homologous to the nucleic acid sequences upstream and downstream of the double stranded break in the DNA molecule, and
wherein the resultant repaired gene, upon expression, confers improved coagulation functionality to the encoded FIX protein of the subject compared to the non-repaired F9 gene.

In additional embodiments, the snRNA delivery system and nanoparticles can be used to repair point mutations, truncations, deletions, inversions, or other genetic mutations that are identified as the causal mutation for a genetic disease.

EXAMPLES

The following examples are set forth below to illustrate the compounds, compositions, methods and results according to the disclosed subject matter. These examples are not intended to be inclusive of all aspects of the subject matter disclosed herein, but rather to illustrate representative compounds, compositions, methods and results. These examples are not intended to exclude equivalents and variations of the present invention which are apparent to one skilled in the art.

Example 1. Lipid-Like Nanoparticles for mRNA Delivery In Vivo

Messenger RNA (mRNA) based therapeutics have shown great promise for expressing functional antibodies and proteins (Pascolo, S. *Handb. Exp. Pharmacol.* 2008, 183, 221-235; Sahin, U. et. al. *Nat. Rev. Drug Discov* 2014, 13, 759-780; Andries, O. et. al, *Expert Rev. Vaccines* 2015, 14, 313-331; Phua, K. K. et. al. W. *Nanoscale* 2014, 6, 7715-7729; Tavernier, G. et. al. *J. Controlled Release* 2011, 150, 238-247). Clinical studies have explored mRNA for use as vaccines through local administration of naked mRNA or mRNA-transfected dendritic cells in order to induce antigen-specific immune responses (Pascolo, S. *Handb. Exp. Pharmacol.* 2008, 183, 221-235; Weide, B. et. al. *J. Immunother.* 2008, 31, 180-188; Weide, B. et. al. *J. Immunother.* 2009, 32, 498-507; Rittig, S. M. et. al. *Mol. Ther.* 2011, 19, 990-999). Recently, extensive efforts have been devoted to achieving the systemic delivery of mRNA using liposomes, polymeric nanoparticles, and mRNA-protein complexes (Wang, Y. et. al. *Mol. Ther.* 2013, 21, 358-367; Phua, K. K. et. al. *J. Controlled Release* 2013, 166, 227-233; Su, X. et. al. *Mol. Pharm.* 2011, 8, 774-787; Geall, A, J. et. al. *Proc. Nall. Acad. Sci. U.S.A.* 2012, 109, 14604-14609; Cheng, C. et. al. *Biomaterials* 2012, 33, 6868-6876). Although significant advances have been made, new mRNA carriers are needed in order to improve delivery efficiency and maximize therapeutic windows of mRNA therapeutics in different human conditions.

Previously, lipid-like nanoparticles (LLNs) have demonstrated efficient delivery of small interfering RNA (siRNA) in rodents and nonhuman primates (Dong, Y. et. al. *Proc. Natl. Acad. Sci. U.S.A.* 2014, 111, 3955-3960; Love Kevin, T. et. al. *Proc. Natl. Acad. Sci. U.S.A.* 2010, 107, 1864-1869; Akinc, A. et. al, *Nat. Biotechnol.* 2008. 26, 561-569; Zhang, Y. et, al. *Adv. Mater.* 2013, 25, 4641-4645; Whitehead, K. A. et. al. *Nat. commun.* 2014, 5, 4277). siRNA and mRNA possess common physicochemical properties, including components of nucleic acids and negative charges; therefore, LLNs may also serve well as mRNA delivery materials. However, LLNs-assisted mRNA delivery is relatively unexplored and understanding of this system is very limited.

Disclosed herein is a new class of $N^1,N^3,N^5$-tris(2-aminoethyl)benzene-1,3,5-tricarboxamide (TT) derived LLNs for mRNA delivery (FIG. 1). TTs are designed to consist of a phenyl ring, three amide linkers, and three amino lipid chains (FIG. 1(a)). An orthogonal experimental design was utilized to experiment with the formulation TT3 LLNs, which improved delivery efficiency over 350-fold. Moreover, correlation analysis of TT LLN properties and mRNA translation identified key determinants of LLN properties for mRNA delivery. In addition, PEGylation of TT3 LLNs showed dramatic effects on particle stability, particle size and mRNA delivery efficiency. Consistent with in vitro observations, an optimized TT3 LLN (O-TT3 LLNs) efficiently delivered mRNA encoding human factor IX, (hFIX) and produced hFIX at a therapeutically relevant level in both wild-type and FIX-knockout mice. This example offers new insights into the development of mRNA delivery materials.

First, a synthetic route to $N^1,N^3,N^5$-tris(2-aminoethyl)benzene-1,3,5-tricarboxamide (TT) derivatives was designed.

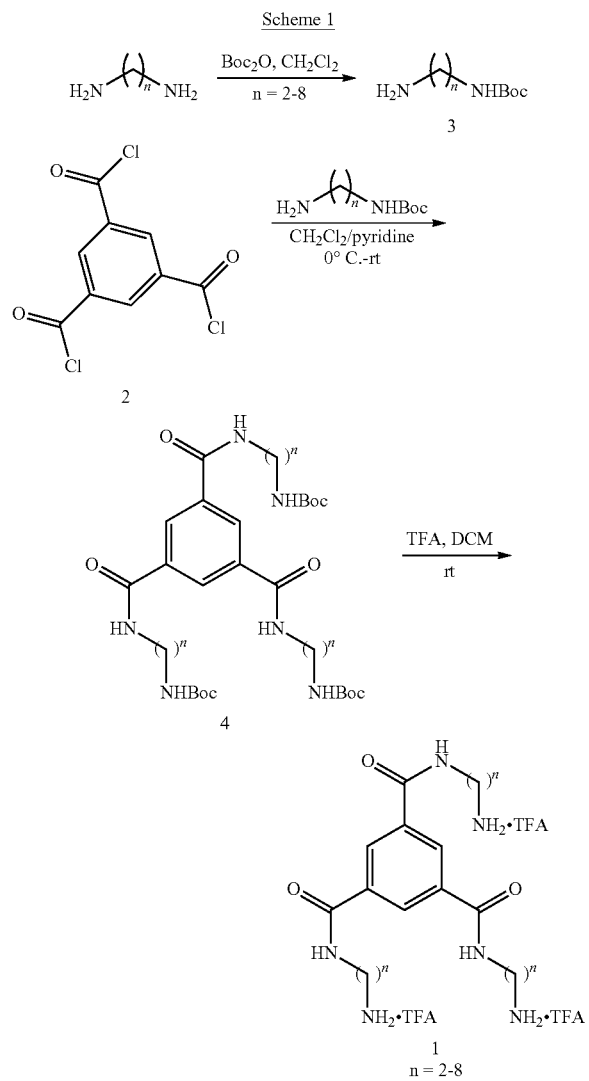

Benzene-1,3,5-tricarbonyl trichloride (2) was reacted with Boc-protected diamine (3) in order to produce the intermediates (4) (Broaders, K. E. et. al. *Chem. Commun.* (Cambridge, U. K.) 2011, 4:7, 665-667). Deprotection of (4) gave compound (1), which underwent reductive amination to afford the desired products TT2 through TT8 (See FIG. 1(a)) (Dong, Y. et. al. *Proc. Natl. Acad. Sci, U.S.A.* 2014, 111, 3955-3960). The structures of TT2-TT8 were confirmed by NMR spectroscopy and mass spectrometry (See methods section below). Newly synthesized TT2-TT8 were then formulated with 1,2-distearoyl-sn-glycero-3-phosphocholine (DSPC), cholesterol (Chol), 1,2-dimyristoy-sn-gtycerol, methoxy polyethylene glycol (DMG-PEG$_{2000}$) (TT/DSPC/Chol/DMG-PEG$_{2000}$=50/10/38.5/1.5, mole ratio) as well as mRNA encoding firefly luciferase (FLuc mRNA) in order to form TT2-TT8 LLNs (FIG. 1(b)). Meanwhile, particle properties including size, zeta potential, and entrapment efficiency of TT2-TT8 LLNs were measured using a dynamic light-scattering instrument and a ribogreen assay (FIG. 8) (Love Kevin, I. et. al. *Proc. Natl. Acad. Sci. U.S.A.* 2010, 107, 1864-1869; Chen, D. et. al. *J. Am. Chem. Soc.* 2012, 134, 6948-6951). Particle size of TT2-TT8 LLNs ranged from 99±2 to 178±1 nm with PDI<0.2. Most TT LLNs were positively charged and entrapment efficiency of mRNA was in the range of 15-82%.

Figure 8:
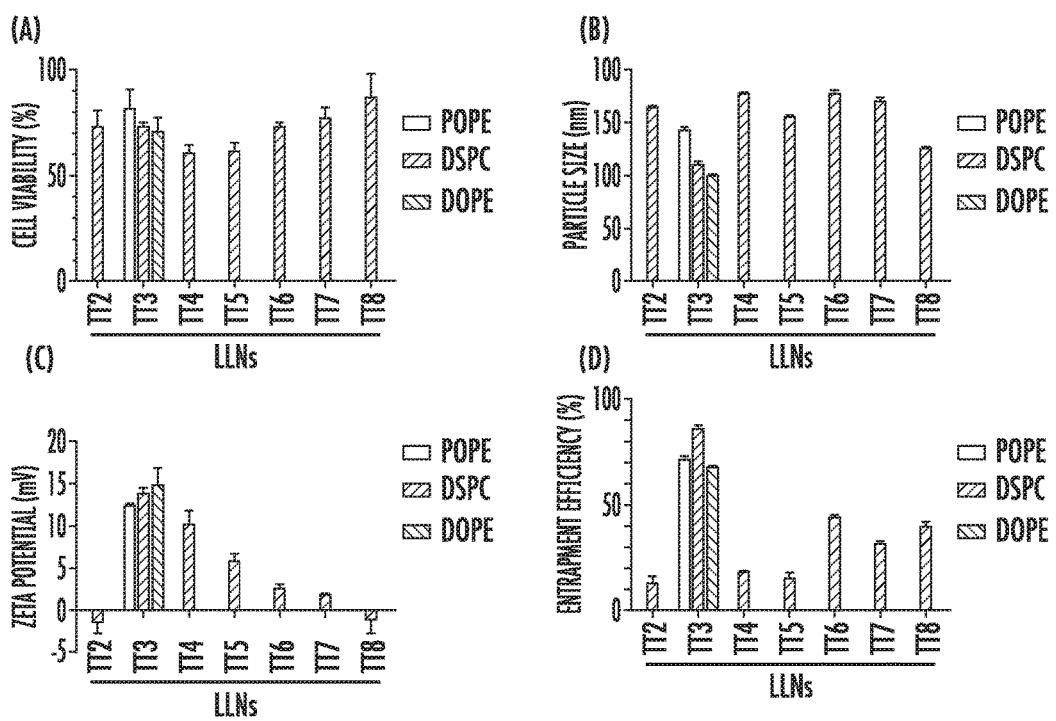
FIG. 8. The cell viability (a), particle size (b), zeta potential (c), and entrapment efficiency (d) of LLNs.

Next, delivery efficiency and cytotoxicity of TT2-TT8 LLNs-FLuc mRNA was evaluated in Hep3B cells, a human hepatoma cell line. As shown in FIG. 2(a), TT3 LLNs showed significantly higher expression of the firefly luciferase compared to other TT LLNs at a dose of 1.2 µg/mL of FLuc mRNA. In addition, TT2-TT8 LLNs showed minimal to moderate inhibitory effects on Hep3B cells (FIG. 8). A correlation analysis was then performed between transfection efficiency and particle size, surface charge, entrapment efficiency and cell viability (FIG. 2(c)-2(e)). A significant positive correlation between transfection efficiency and entrapment efficiency was observed, while there was no significant correlation between transfection efficiency and particle size, surface charge, and cell viability.

To study the effects of helper lipids on delivery efficiency, the lead material, TT3, was formulated with 2-dioleoyl-sn-glycero-3-phosphoethanolamine (DOPE) or 1-palmitoyl-2-oleoyl-sn-glycero-3-phosphoethanolamine (POPE) in the presence of other formulation components. DOPE formulated TT3 LLNs were more potent than DSPC and POPE formulated TT3 LLNs (FIG. 2(f)). On the basis of the above results, the formulation components of TT3 LLNs were determined as TT3, DOPE, cholesterol, and DMG-PEG$_{2000}$.

Figure 3:
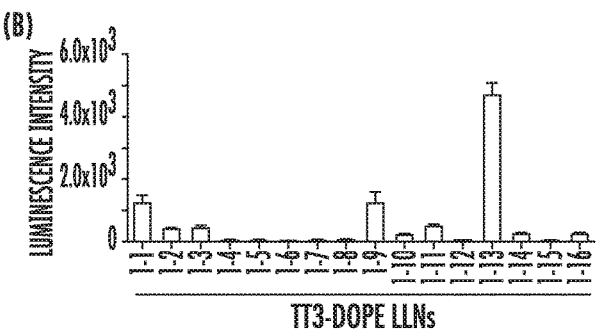
FIG. 3. A first round of orthogonal experimental design and analysis. (a) Four levels for each formulation component: TT3, DOPE, cholesterol, and DMG-PEG$_{2000}$, (1)) Sixteen combinations (1-1 to 1-16) were evaluated with Hep3B cells for their relative luminescence intensity through the first orthogonal array. (c-f) The impact trend of TT3 (c), DOPE (d), cholesterol (e), and DMG-PEG$_{2000}$ (f) on delivery efficiency. Increased TTS and DMG-PEG$_{2000}$ reduced mRNA delivery efficiency, while increased DOPE facilitated mRNA delivery efficiency. The optimal ratio for cholesterol ranged from 20 to 40.
Figure 3:
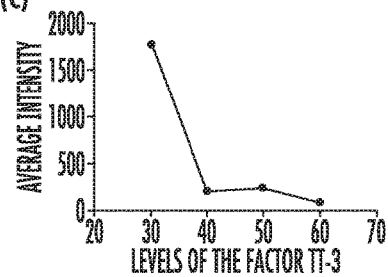
Figure 3:
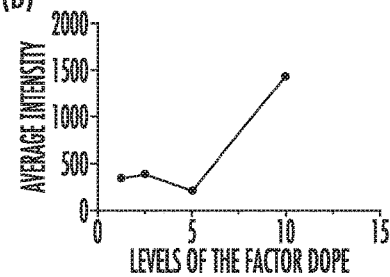
Figure 3:
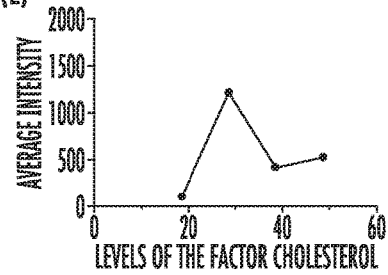
Figure 3:
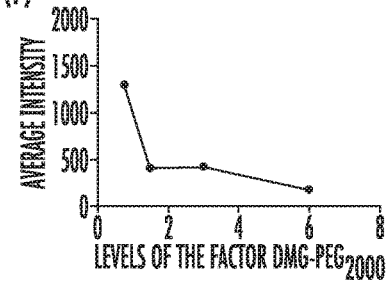
Figure 9:
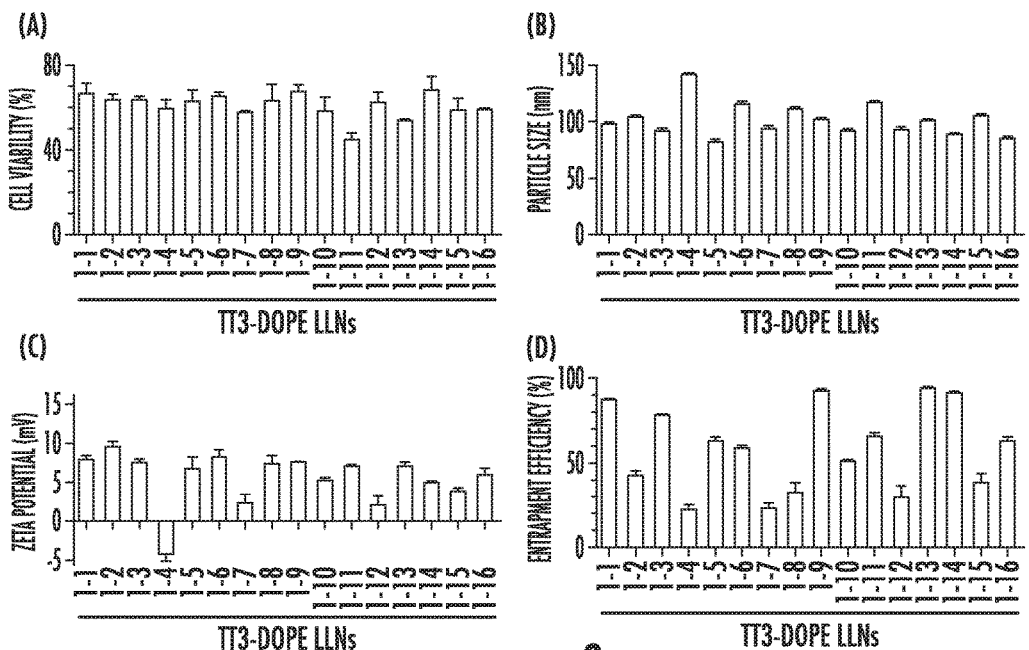
FIG. 9. The cell viability (a), particle size (b), zeta potential (c), and entrapment efficiency (d) of TT3-DOPE LLNs formulated through the first orthogonal array.

In order to experiment with the formulation of TT3 LLNs, an orthogonal experimental design was applied, which has been used for biomedical studies (Cui, W. G. et. al. *J. Appl. Polym. Sci.* 2007, 103, 3105-3112; Marks, J. R. et. al. *J. Am. Chem. Soc.* 2011, 133, 8995-9004; Ryan, D.; Papamichail, D. *Acs Synth Biol* 2013, 2, 237-244; Zhan, J. Y. et. al. *J. Agric. Food Chem.* 2011, 59, 6091-6098; Meng, H. N. et. al. *Appl. Surf Sci.* 2013, 280, 679-685; Liu, L. et. al. *J. Nanosci. Nanotechnol.* 2013, 13, 8137-8143). This approach allowed experimentation with the formulation ratios with a minimum number of experiments. As shown in FIG. 3(a), four levels for each formulation component were investigated: TT3, DOPE, cholesterol, and DMG-PEG$_{2000}$. Theoretically, four levels of four formulation components can yield 256 combinations. By utilizing the orthogonal experimental design, the effects of the 4 components with only 16 combinations were evaluated (Table 2 and FIG. 9).

TABLE 2

Orthogonal array table $L_{16}(4^4)$ for the first round of TT3-DOPE LLNs.

| TT3-DOPE LLNs | Formulation components (mole ratio) | | | | Relative luminescence intensity |
|---|---|---|---|---|---|
| | TT3 | DOPE | Cholesterol | DMG-PEG$_{2000}$ | |
| 1-1 | 30 | 2.5 | 38.5 | 3 | 1216 |
| 1-2 | 40 | 10 | 18.5 | 1.5 | 351 |
| 1-3 | 50 | 10 | 38.5 | 6 | 418 |
| 1-4 | 60 | 2.5 | 18.5 | 0.75 | 20 |
| 1-5 | 30 | 5 | 18.5 | 6 | 28 |
| 1-6 | 40 | 1.25 | 38.5 | 0.75 | 28 |
| 1-7 | 50 | 1.25 | 18.5 | 3 | 34 |
| 1-8 | 60 | 5 | 38.5 | 1.5 | 51 |
| 1-9 | 30 | 1.25 | 48.5 | 1.5 | 1207 |
| 1-10 | 40 | 5 | 28.5 | 3 | 203 |
| 1-11 | 50 | 5 | 48.5 | 0.75 | 469 |
| 1-12 | 60 | 1.25 | 28.5 | 6 | 30 |
| 1-13 | 30 | 10 | 28.5 | 0.75 | 4663 |
| 1-14 | 40 | 2.5 | 48.5 | 6 | 220 |
| 1-15 | 50 | 2.5 | 28.5 | 1.5 | 20 |
| 1-16 | 60 | 10 | 48.5 | 3 | 243 |

The impact of the four components on mRNA delivery (ΔK): TT3 DOPE>Cholesterol=DMG-PEG$_{2000}$.

Figure 2:
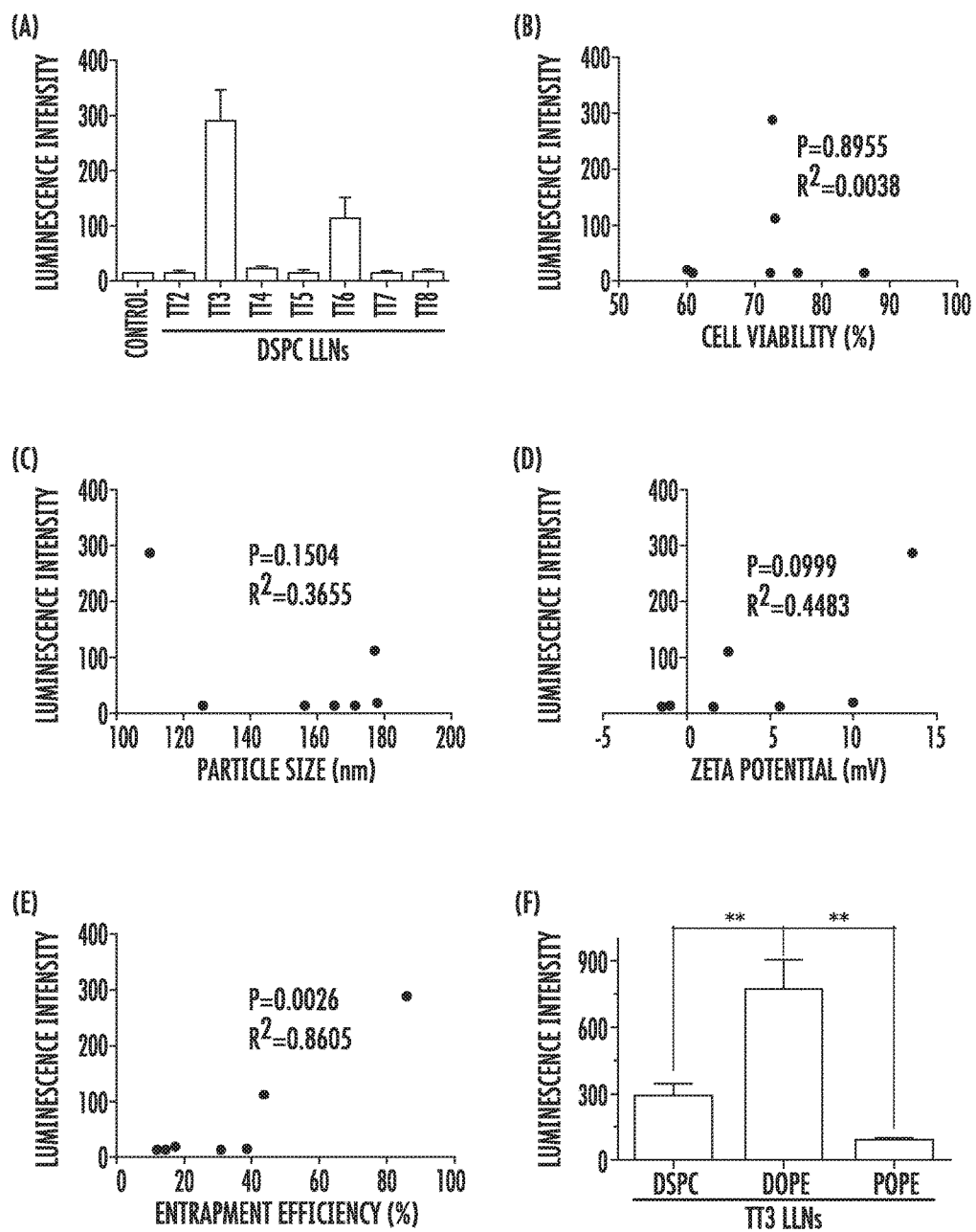
FIG. 2. Delivery efficiency of TT2-TT8 LLNs to Hep3B cells (a human hepatoma cell line) and correlation analysis between transfection efficiency and cell viability, particle size, zeta potential, and entrapment efficiency. (a) TT3 LLNs showed significantly higher expression of the firefly luciferase compared to other TT LLNs at a dose of 1.2 μg/mL of luciferase mRNA. (b-e) Correlation analysis between transfection efficiency of TT LLNs and cell viability, particle size, zeta potential, or entrapment efficiency. A significant correlation between transfection efficiency and entrapment efficiency was observed, while no significant correlation between transfection efficiency and particle size, surface charge, and cell viability. (f) Effects of helper lipids on mRNA delivery efficiency. DOPE formulated TT3 LLNs were more potent than DSPC and POPE formulated TT3 LLNs. (triplicate; **, P<0.01; t test, double-tailed).

Because the impact of the four components was unknown, FIG. 3(a) displayed the arbitrarily assigned four levels for each component based on the molar ratio (50/10/38.5/1.5) tested in FIG. 2. From the first round of experimentation, the effects of the four components (TT3>DOPE>Chol=DMG-PEG$_{2000}$) were ranked by comparing the ΔK values (Table 3).

TABLE 3

$K_n$ values for the first round of TT3-DOPE LLNs.

| | TT3 | DOPE | Cholesterol | DMG-PEG$_{2000}$ |
|---|---|---|---|---|
| $K_1$* | 1779 | 325 | 108 | 1295 |
| $K_2$* | 201 | 369 | 1229 | 407 |
| $K_3$* | 235 | 188 | 428 | 424 |
| $K_4$* | 86 | 1419 | 535 | 174 |
| ΔK** | 1693 | 1231 | 1121 | 1121 |

$K_n$* = ΣRLL$_n$/4
ΔK** = $K_{max}$ − $K_{min}$

Figure 4:
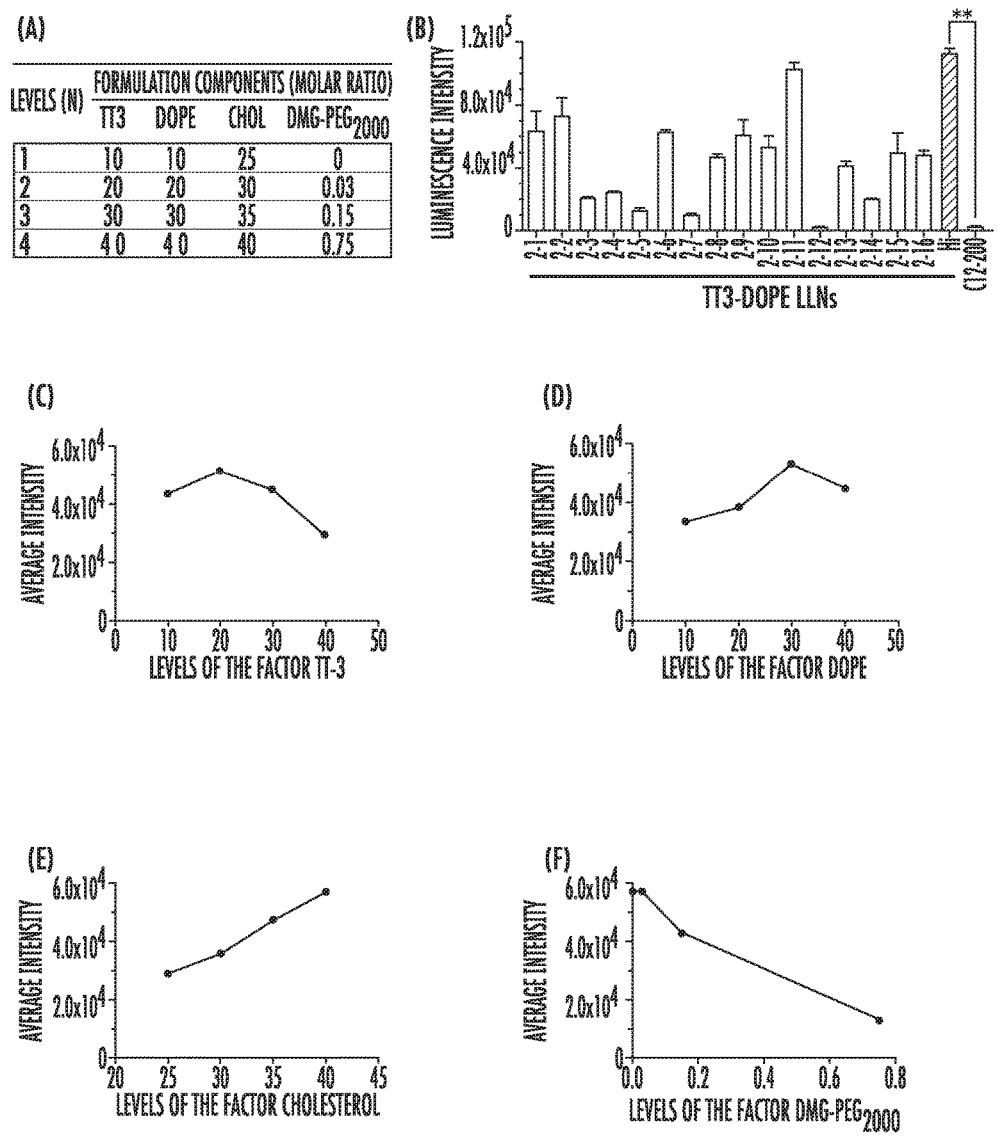
FIG. 4. A second round of orthogonal experimental design and analysis. (a) Four levels for each formulation component: TT3, DOPE, cholesterol, and DMG-PEG$_{2000}$. (b) Sixteen combinations (2-1 to 2-16) were evaluated with Hep3B cells or their relative luminescence intensity through the second orthogonal array. The most efficient formulation was validated with a designated code of Hi-TT3 LLNs (formulation ratio is TT3/DOPE/Chol/DMG-PEG$_{2000}$=20/30/40/0). (triplicate; **, P<0.01; t test, double-tailed). (c-f) The impact trend of TT3 (c), DOPE (d), cholesterol (e) and DMG-PEG$_{2000}$ (f) on delivery efficiency.

Luciferase expression of TT3 LLNs was increased over 6-fold after the first round of experimentation (173 LLNs 1-13 vs TT3-DSPC LLNs, FIG. 3(b)). In order to further test the formulation ratio and improve mRNA delivery efficiency, a second round of orthogonal testing was conducted. FIGS. 3(c)-3(f) provided guidance for assigning four levels of each component (FIG. 4(a)). The trend in FIG. 3(c) showed that TT3 with reduced levels may facilitate mRNA delivery. Hence, the ratio of TT3 was gradually decreased from 40 to 10. TT3 exhibited the highest impact on delivery efficiency in the first orthogonal array (Table 3); therefore, two levels of TT3 were overlapped with that in the first round. The ratio of DOPE was then increased from 10 to 40 and decreased the ratio of DMG-PEG$_{2000}$ from 0.75 to 0 based on the trend in FIGS. 3(d) and 3(f). One level of DOPE and DMG-PEG$_{2000}$ was overlapped with that in the first round of experimentation in order to avoid discontinuity. Lastly, because the peak of cholesterol was between 18.5 and 38.5 (FIG. 3(e)) its level was reassigned with a reduced interval.

Figure 11:
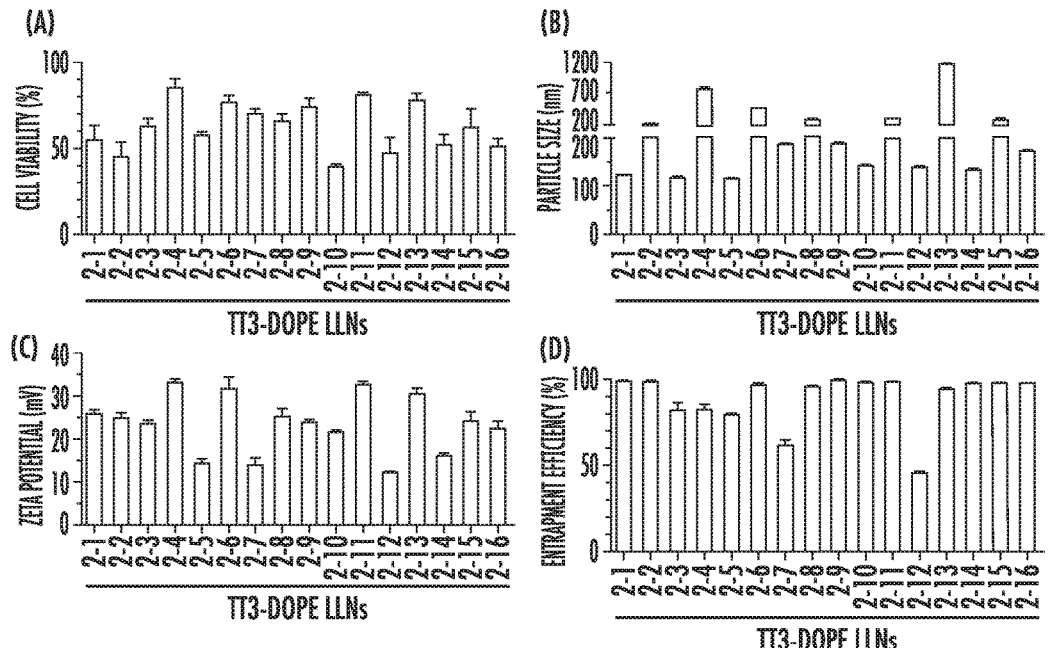
FIG. 11. The cell viability (a), particle size (b), zeta potential (c), and entrapment efficiency (d) of TT3-DOPE LLNs formulated through the second round of orthogonal array.

In the second round of orthogonal experiments, 16 formulation combinations were evaluated as described above (FIG. 4, Table 4, and FIG. 11).

TABLE 4

Orthogonal array table $L_{16}(4^4)$ for the second round of TT3-DOPE LLNs.

| TT3-DOPE LLNs | Formulation components (mole ratio) | | | | Relative luminescence intensity |
|---|---|---|---|---|---|
| | TT3 | DOPE | Cholesterol | DMG-PEG$_{2000}$ | |
| 2-1 | 10 | 20 | 35 | 0.15 | 62542 |
| 2-2 | 20 | 40 | 25 | 0.03 | 71935 |
| 2-3 | 30 | 40 | 35 | 0.75 | 19869 |
| 2-4 | 40 | 20 | 25 | 0 | 23096 |
| 2-5 | 10 | 30 | 25 | 0.75 | 11687 |
| 2-6 | 20 | 10 | 35 | 0 | 62216 |
| 2-7 | 30 | 10 | 25 | 0.15 | 9394 |
| 2-8 | 40 | 30 | 35 | 0.03 | 45962 |
| 2-9 | 10 | 10 | 40 | 0.03 | 60333 |
| 2-10 | 20 | 30 | 30 | 0.15 | 52468 |
| 2-11 | 30 | 30 | 40 | 0 | 101863 |
| 2-12 | 40 | 10 | 30 | 0.75 | 1917 |
| 2-13 | 10 | 40 | 30 | 0 | 40410 |
| 2-14 | 20 | 20 | 40 | 0.75 | 18962 |
| 2-15 | 30 | 20 | 30 | 0.03 | 49102 |
| 2-16 | 40 | 40 | 40 | 0.15 | 47049 |

FIG. 4(b)-4(f) displayed the relative intensity of luciferase expression and the impact trend of the four components. The predicted best formulation was identified by selecting the highest values of these four components (Table 5, highlighted in bold), which was TT3/DOPE/Chol/DMG-PEG$_{2000}$=20/30/40/0 (named Hi-TT3 LLNs).

TABLE 5

$K_n$ values for the second round of TT3-DOPE LLNs.

| | TT3 | DOPE | Cholesterol | DMG-PEG$_{2000}$ |
|---|---|---|---|---|
| $K_1$* | 43743 | 33465 | 29028 | 56896 |
| $K_2$* | 51395 | 38426 | 35974 | 56833 |
| $K_3$* | 45057 | 52995 | 47647 | 42863 |
| $K_4$* | 29506 | 44816 | 57052 | 13109 |
| ΔK** | 21889 | 19529 | 18025 | 43788 |

$K_n$* = ΣRLL$_n$/4
ΔK** = $K_{max}$ − $K_{min}$

The most efficient formulation in the second round of formulation experimentation was validated with a designated code of Hi-TT3 LLNs (formulation ratio is TT3/DOPE/Chol/DMG-PEG$_{2000}$=20/30/40/0).

Hi-TT3 LLNs were further evaluated by their luciferase expression level (FIG. 4(b)), which showed comparable delivery efficiency to the formulation of m LLNs 2-11 (TT3/DOPE/Chol=30/30/40) (FIG. 4(b) and Table 4). Cationic lipids have potential toxicity (Lv, H. et, al. *J. Controlled Release* 2006, 114, 100-109); therefore, Hi-TT3 LLNs with the lower percentage of TT3 were selected for further studies. Importantly, Hi-TT3 LLNs increased delivery efficiency over 20-fold compared to the best formulation (TT3 LLNs 1-13) identified in the first round of orthogonal experiments and over 350-fold compared to the original start-point TT3-DSPC LLNs (FIG. 4(b)). More importantly, Hi-TT3 LLNs were over 65-fold more efficient than C12-200-DSPC LLNs (see structure below), a previously reported material (Love Kevin, I. et. al. *Proc. Natl. Acad. Sci. U.S.A.* 2010, 107, 1864-1869).

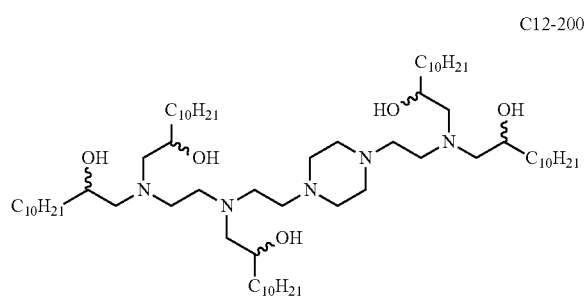

C12-200

Figure 10:
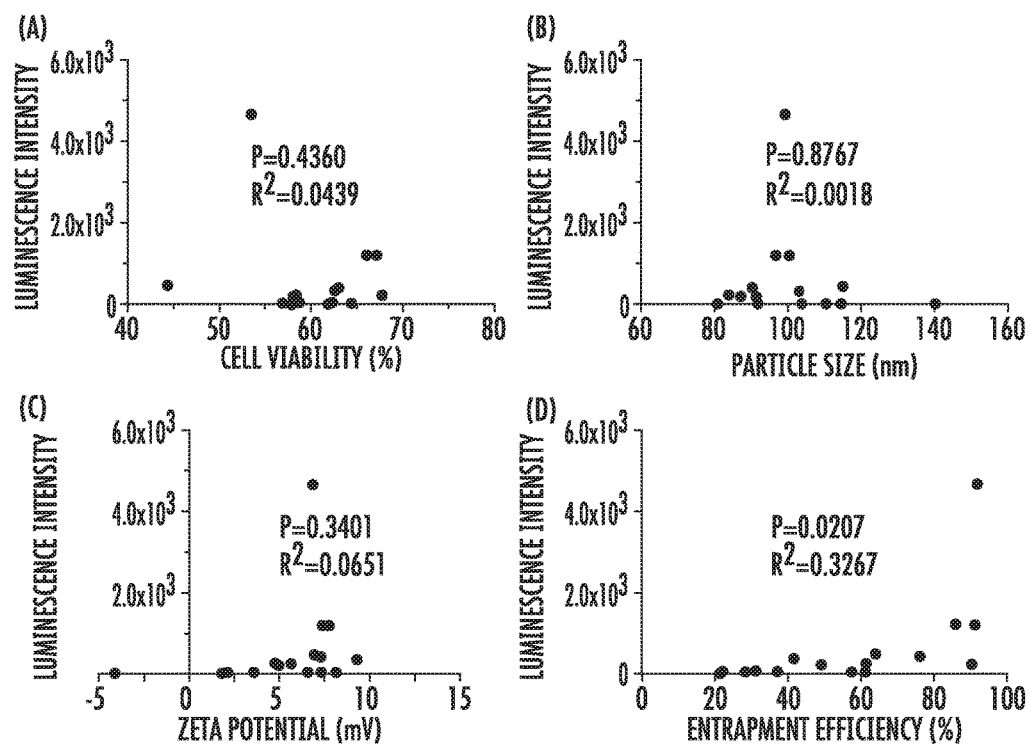
FIG. 10. The correlation between transfection efficiency of TT3-DOPE LLNs formulated through the first orthogonal array and cell viability (a), particle size (b), zeta potential (c), and entrapment efficiency (d).
Figure 12:
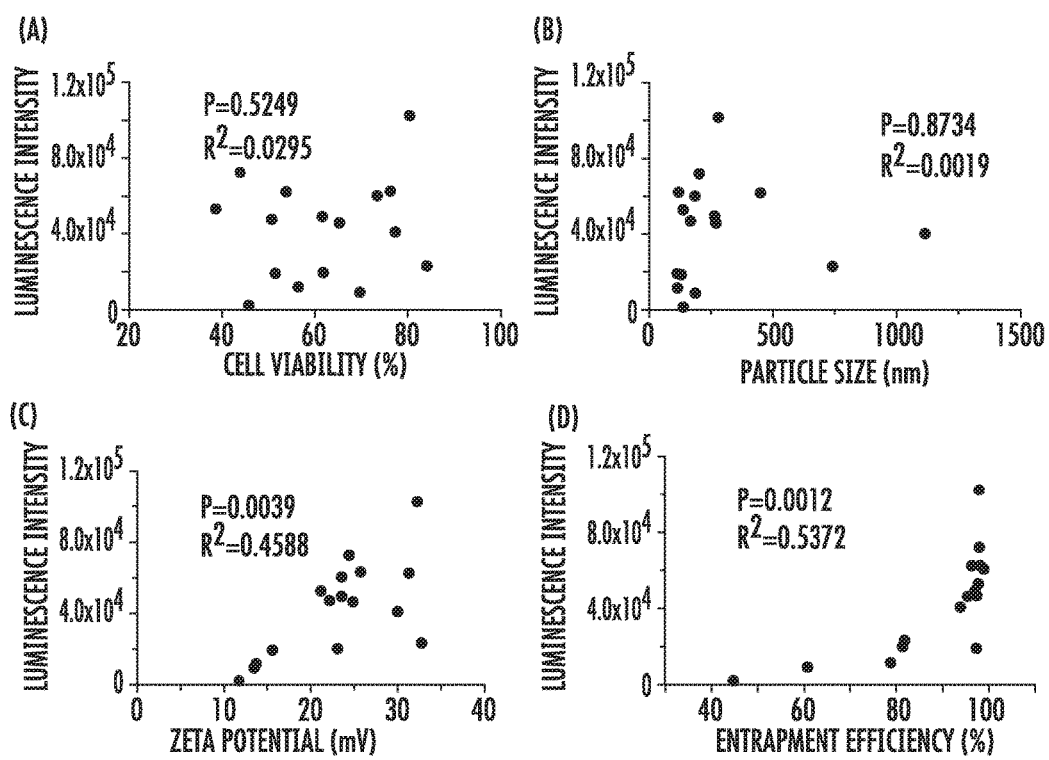
FIG. 12. The correlation between transfection efficiency of TT3-DOPE LLNs formulated through the second round of orthogonal array and their corresponding cell viability (a), particle size (b), zeta potential (c), and entrapment efficiency (d).

These results indicate that an orthogonal experimental design represents a powerful approach to the goal of developing improved nanoparticle formulations. Consistent with previous findings (FIG. 10), significant correlation was observed between transfection efficiency and entrapment efficiency, while there was no significant correlation with particle size and cell viability in the two rounds of orthogonal experiments (FIG. 12). Interestingly, zeta potential also showed significant correlation with transfection efficiency in the second round of orthogonal experiments (FIG. 12).

Figure 5:
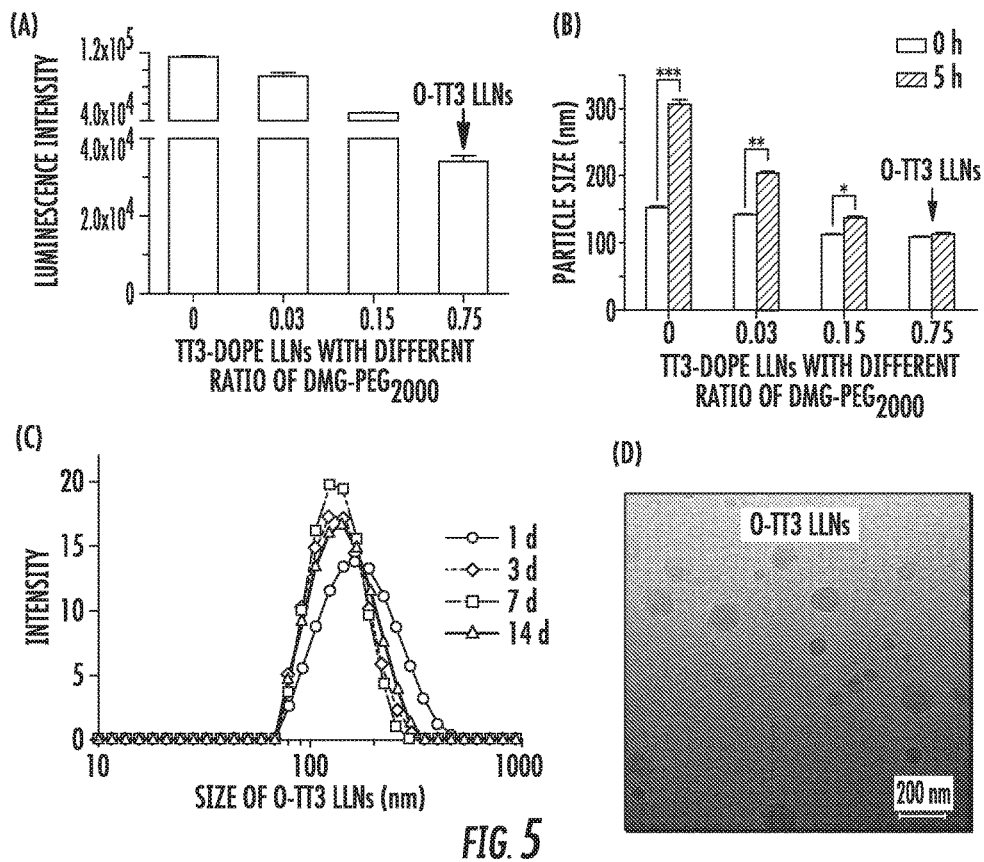
FIG. 5. Impact of PEGlyation on TT3 LLNs. The ratio of DMG-PEG$_{2000}$ was negatively correlated with delivery efficiency in Hep3B cells (a) and particle size (b). TT3 LLNs were increasingly stable with addition of DMG-PEG$_{2000}$. (triplicate; *, P<0.05; ; P<0.01; *, P<0.001; t test, double-tailed). (c) O-TT3 LLNs were stable for at least 2 weeks. (d) A representative Cryo-TEM image of O-TT3 LLNs. Scale bar: 200 nm.
Figure 6:
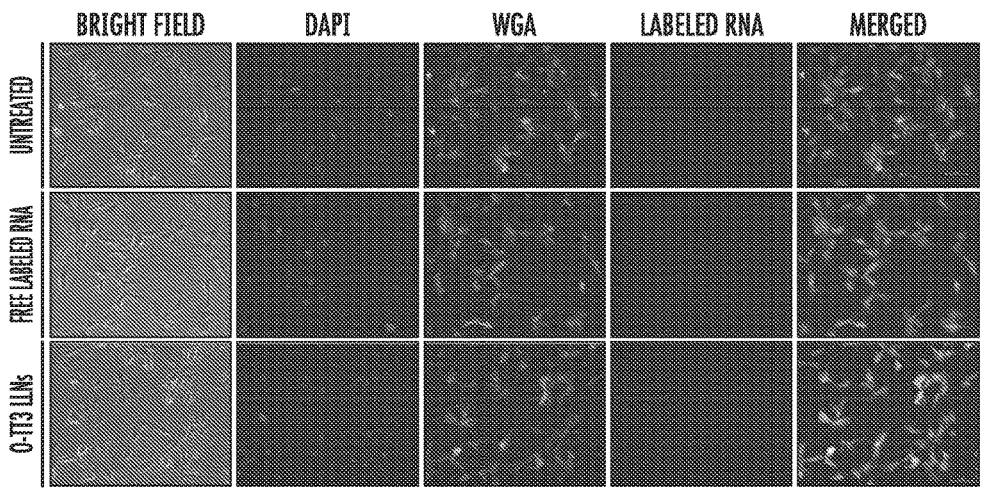
FIG. 6. Cellular uptake of O-TT3 LLNs, Cell nuclei and membranes of Hep3B cells were stained with DAPI (second column) and WGA (third column), respectively. Alexa-Fluor 647-labeled RNA (fourth column). Scale bar: 50 μm.

Previous studies report that PEGlyation of polymer-based nanoparticles significantly affects the stability and cellular uptake (Mishra, S. et. al. *Ear. J. Cell Biol.* 2004, 83, 97-111; Otsuka, et. al. *Adv. Drug Delivery Rev.* 2003, 55, 403-419). Interestingly, Hi-TT3 LLNs are not stable without the incorporation of DMG-PEG$_{2000}$ in the formulation. The impact of DIG-PEG$_{2000}$ on delivery efficiency, particle size and stability was also investigated. Consistent with reports in the literature, (Mishra, S. et. al. *Eur. J. Cell Biol.* 2004, 83, 97-111; Otsuka, H. et. al. *Adv. Drug Delivery Rev.* 2003, 55, 403-419) the results showed that the ratio of DMG-PEG$_{2000}$ was negatively correlated with delivery efficiency and particle size; that is the higher ratio of DMG-PEG$_{2000}$, the lower the luciferase expression and the smaller the particles is (FIGS. 5($a$) and 5($b$)). The particle size of TT3 LLNs increased dramatically 5 h after formulation with a low ratio of DMG-PEG$_{2000}$ (FIG. 5($b$)). When formulated with the molar ratio TT3/DOPE/Chol/DMG-PEG$_{2000}$=20/30/40/0.75 (named O-TT3 LLNs), these nanoparticles were stable for a minimum of 2 weeks (FIG. 5($c$)). In order to balance delivery efficiency with particle stability, the formulation O-TT3 LLNs was chosen for further studies. Cryo-EM image showed the spherical morphology of O-TT3 LLNs (FIG. 5($d$)). To visualize the cellular uptake of O-TT3 LLNs, Hep3B cells were treated using O-TT3 LLNs loaded with Alexa-Fluor 647-labeled RNA and FLuc mRNA (weight ratio: 1/1). Three hours after treatment, cells were fixed with formaldehyde. Cell membranes and nuclei were then stained by Alexa fluor 488 conjugate of wheat germ agglutinin (FIG. 6, third column) and NucBlue fixed cell ready probes reagent (FIG. 6, second column), respectively. Compared to untreated and free RNA-treated cells, significant cellular uptake of TT3 LLNs was observed (FIG. 6). Reflecting all of the above results, O-TT3 LLNs formulation was selected (TT3/DOPE/Chol/DMG-PEG$_{2000}$=20/30/40/0.75) for in vivo studies.

Figure 13:
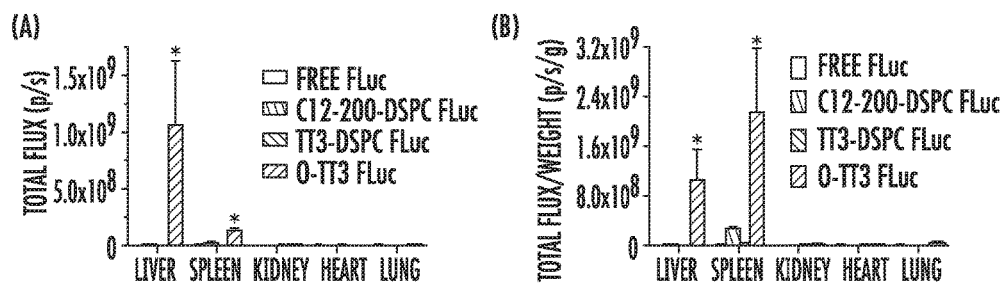
FIG. 13. Bioluminescence signal (6 hours after administration in C57BL/6 mice). Free FLuc mRNA served as a negative control. Total bioluminescence signal (a) and normalized bioluminescence signal with tissue weight (b). Statistically significant difference was observed in the groups (*: P<0.05; O-TT3 FLuc vs C12-200-DSPC FLuc; O-TT3 FLuc vs TT3-DSPC FLuc).

To understand biodistribution of O-TT3 LLNs in vivo, O-TT3 FLuc LLNs were injected intravenously at an mRNA dose of 0.5 mg/kg with control groups of free FLuc mRNA, C12-200-DSPC LLNs, and the original TT3-DSPC LLNs. Six hours post administration, bioluminescence intensities of dissected organs were measured using the IVIS imaging system. O-TT3 LLNs-treated group showed significantly higher bioluminescence signal in the liver and spleen compared to C12-200-DSPC LLNs, and TT3-DSPC LLNs-treated groups. No signal was detected in the kidney, lung, and heart (FIG. 13). These in vivo results further validated that in vitro optimizations of TT3 LLNs was an effective approach.

Figure 7:
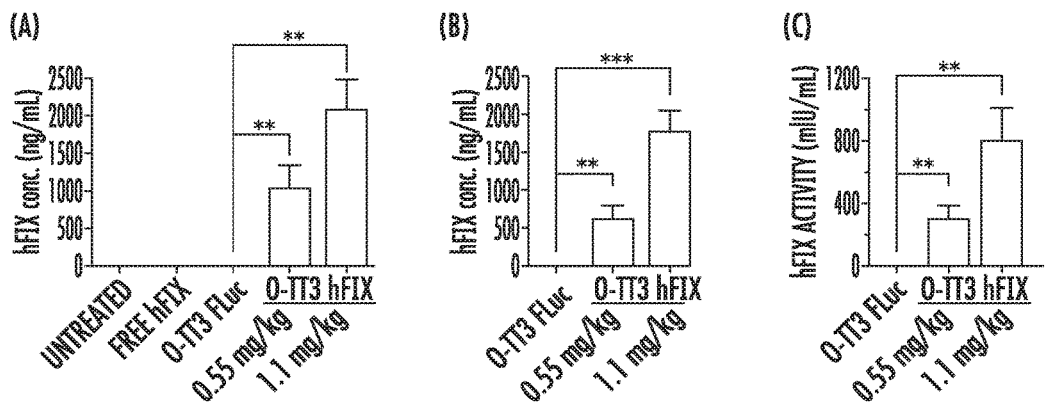
FIG. 7 hFIX level in wild-type (a) and FIX knockout (b) mice 6 h after intravenous administration. (O-TT3 FLuc, FLuc mRNA formulated O-TT3 LLNs; O-TT3 hFIX, human FIX mRNA formulated O-TT3 LLNs). (c) Human FIX protein activity. MIX activity is 304 mlU/mL (0.55 mg/kg) and 791 mlU/mL (1.1 mg/kg) in O-TT3 hFIX LLNs treated group, while no detectable activity was found in O-TT3 FLuc LLNs treated FIX-knockout mice. (n=3, , P<0.01; *, P<0.001; t test, double-tailed).
Figure 14:
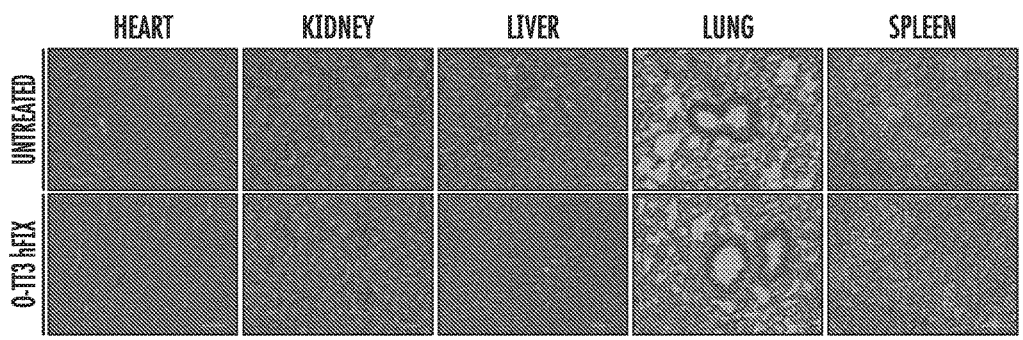
FIG. 14. Histological analysis of major organs (heart, kidney, liver, lung, and spleen) after treatment of O-TT3 hFIX. Untreated groups served as negative controls. No significant alteration of histology was observed in the O-TT3 LLNs treated groups compared to the control groups.

To further study the delivery efficiency of O-TT3 LLNs in vivo, an mRNA-encoding human factor IX (hFIX), a blood clotting factor, and therapeutically relevant protein, was selected (Coppola, A. et. al. *J. Blood med.* 2010, 1, 183-195), Deficiency of hFIX protein leads to the inherited genetic disorder, hemophilia B, which impairs the process of hemostasis and results in serious complications, including joint and muscle hemorrhage (Coppola, A. et. al. *J, Blood med.* 2010, 1, 183-195; Monahan, P. F.; White, G. C., 2nd. *Curr. Opin. Hematol.* 2002, 9, 430-436; Sabatino, D. E. et. al. *Progress in molecular biology and translational science* 2012, 105, 151-209). In this study, O-TT3 LLNs were formulated with hFIX mRNA and then injected the formulation intravenously in wild-type mice. Six hours after administration, the level of hFIX was measured by a well-established chromogenic ELISA assay (Barzel, A. et. al. *Nature* 2015, 517, 360-364). Wild-type mice produced 1020 ng/mL hFIX at a dose of 0.55 mg/kg and 2057 ng/mL at a dose of 1.1 mg/kg, respectively. No hFIX was detected in the plasma of mice injected with untreated, free hFIX mRNA- or TT3 LLNs-treated groups (FIG. 7($a$)). Meanwhile, no significant alterations in clinical appearance were observed in the O-TT3 LLNs treated groups compared to the control groups. Histopathology analysis was consistent with these observations, which suggested that O-TT3 LLNs were well tolerated at the current dose (FIG. 14). Next, the delivery efficiency of O-TT3 LLNs in FIX-knockout mice was tested (Wang, L. et. al. *Proc. Natl. Acad. Sci. U.S.A.* 1997, 94, 11563-11566). Compared to O-TT3 FLuc LLNs, O-TT3 hFIX LLNs induced significant production of hFIX in a dose-dependent manner (608 ng/mL at a dose of 0.55 mg/kg and 1740 ng/mL at a dose of 1.1 mg/kg) in the FIX-knockout mice (FIG. 7($b$)). Lastly, hFIX activity was quantified using a well described chromogenic assay, in which the coagulation factor IX is activated by activated Factor eleven (FXIa) with simultaneous activation of Factor ten (FX) in the presence of Factor eight (FVIII), phospholipid and Ca$^{2+}$ followed by hydrolysis of a chromogenic FXa substrate (Barzel, A. et. al. *Nature* 2015, 517, 360-364). The normal plasma level of hFIX in humans ranges from 500 to 1500 mIU/mL (van Hylckama Vlieg, A. et. al. *Blood* 2000, 95, 3678-3682; Srivastava, A. et, al. Treatment Guidelines Working Group on Behalf of The World Federation Of, H. *Haemophilia* 2013, 19, e1-47). As shown in FIG. 7($c$), the plasma level of hFIX was 304 mIU/mL at a dose of 0.55 mg/kg and 791 mIU/mL at a dose of 1.1 mg/kg in the O-TT3 MIX LLNs treated group, while no detectable signal was found in O-TT3 FLuc LLNs treated FIX-knockout mice. Taken together, O-TT3 hFIX LLNs were capable of restoring the hFIX to normal physiological values in FIX-knockout mice, which demonstrates that this delivery system has the potential for therapeutic applications.

In summary, a new type of lipid-like compounds ($N^1,N^3$, $N^5$-tris(2-aminoethyl)benzene-1,3,5-tricarboxamide derivatives (TT2-TF8)) were developed, composed of a phenyl ring, three amide linkers and three amino lipid chains. An orthogonal experimental design for formulation experimentation was utilized, which is an efficient approach to the rapid evaluation of multiple formulation parameters and the identification of the best formulation ratio with significantly reduced experimental numbers (32 out of 512). More importantly, this approach improved the transfection efficiency over two orders of magnitude after two rounds of experiments. In addition, the experimental array obtained through orthogonal methods represents the independency of all formulation combinations, thus offering a series of reliable data to perform correlation analysis. The analysis results indicate that entrapment efficiency of mRNA plays a key role for cellular transfection. Zeta potential may correlate with mRNA delivery efficiency for certain LLNs formulations. These results validate the usefulness of the orthogonal experiment design in order to determine formulations for multicomponent nanoparticles for mRNA delivery. Meanwhile, PEGylation of TT3 LLNs improved particle stability and reduced particle size but hindered delivery efficiency, which is consistent with observations of other polymer-based drug delivery systems reported in the literature (Mishra, S. et. al, $Eur. J. Cell Biol.$ 2004, 83, 97-111; Otsuka, H. et. al. $Adv. Drug Delivery Rev.$ 2003, 55, 403-419). After the ratio of DMG-PEG$_{2000}$ was determined, O-TT3 LLNs showed over 110-fold higher delivery efficiency compared to the start-point TT3-DSPC LLNs, and O-TT3 LLNs were stable for over 2 weeks. Moreover, O-TT3 LLNs showed much higher delivery efficiency of FLuc mRNA both in vitro and in vivo, compared to a C12-200-DSPC LLNs reported previously (Love Kevin, T. et. al. $Proc. Natl. Acad. Sci. U.S.A.$ 2010, 107, 1864-1869). Lastly, the delivery efficiency of O-TT3 LLNs was evaluated for a therapeutically relevant mRNA encoding hFIX (1662 nucleotides), which possesses comparable length to mRNA-encoding luciferase (1929 nucleotides). In the case that O-TT3 LLNs are utilized to deliver mRNAs with significantly different length, the formulation ratio can be further revised, if necessary. Our results showed that O-TT3 LLNs efficiently delivered hFIX mRNA in both wild-type and FIX-knockout mice. Most importantly, O-TT3 LLNs fully recovered the level of hFIX (791 mIU/mL at 1.1 mg/kg) to normal physiological values (500-1500 mIU/mL) in FIX-knockout mice. These results demonstrate that O-TT3 LLNs produce an mRNA delivery system for use in many therapeutic applications, for example, protein replacement, gene engineering, and immunotherapy.

Methods and Experimental Details

Materials. mRNAs encoding Firefly luciferase (FLuc mRNA) and human factor IX mRNA (hFIX mRNA) were purchased from TriLink Biotechnologies, Inc (San Diego, Calif.). Alexa fluor 488 conjugate of wheat germ agglutinin, NucBlue Fixed cell ready probes DAPI, ProLong diamond antifade mountant reagent, Ribogreen reagent and fetal bovine serum (FBS) were purchased from Life Technologies (Grand Island, N.Y.). Alexa-Fluor 647-labeled RNA was purchased from integrated DNA Technologies. 1,2-distearoyl-sn-glycero-3-phosphocholine (DSPC), 1,2-dioleoyl-sn-glycero-3-phosphoethanolamine (DOPE), and 1-palmitoyl-2-oleoyl-sn-glycero-3-phosphoethanolamine (POPE) were purchased from Avanti Polar Lipids, Inc. 3-(4,5-dimethylthiazol-2-yl)-2,5-diphenyltetrazolium bromide (MTT) was purchased from Amresco (Solon, Ohio). Bright-Glo luciferase assay substrate was from Promega (Madison, Wis.). Buffered formaldehyde (10%, pH 7.4) was purchased from Ricca Chemical (Arlington, Tex.), Goat anti-hFIX HRP antibody was purchased from Enzyme Research Laboratories (South Bend, Ind.). O-Phenylenediaminedihydrochloride (15 mg substrate per tablet), cholesterol, human factor IX, monoclonal anti-human factor IX antibody, and other chemicals were purchased from Sigma-Aldrich.

Synthesis of TT2-TT8. To a suspension of compound 1 (0.1 mmol) in 10 mL of anhydrous tetrahydrofuran was added triethylamine (0.4 mmol) under nitrogen protection. The mixture was stirred for 30 min at WT. After adding dodecyl aldehyde (0.9 mmol) and NaBH(OAc)$_3$, the reaction mixture was stirred at RT for 48 h. After the solvent was removed, the residue was purified by column chromatography using a CombiFlash Rf system with a Redi Sep Gold Resolution silica column (Teledyne Isco) with gradient elution from 100% CH$_2$Cl$_2$ to CH$_2$Cl$_2$/MeOH/NH$_4$OH (75/22/3 by volume) to give TT2-TT8.

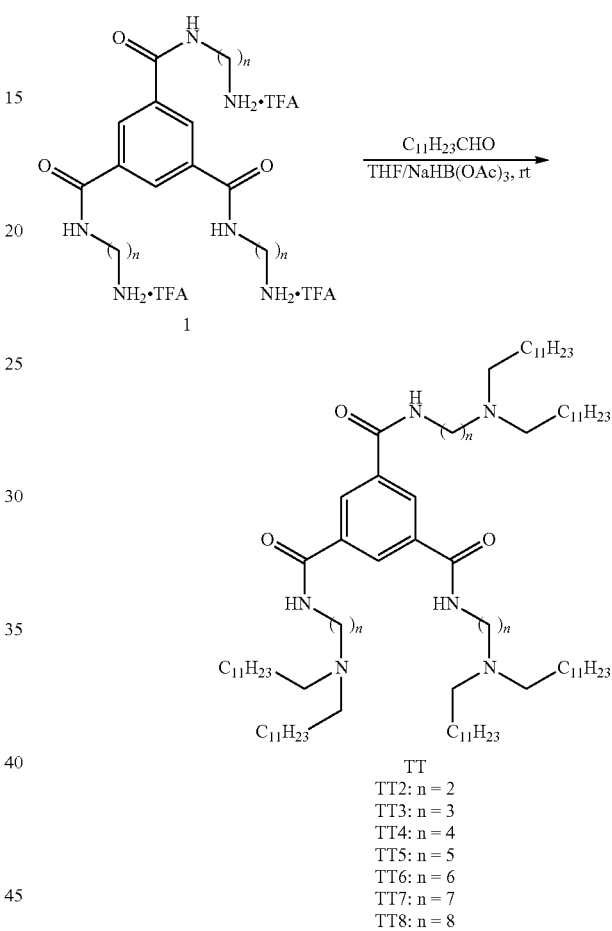

TT
TT2: n = 2
TT3: n = 3
TT4: n = 4
TT5: n = 5
TT6: n = 6
TT7: n = 7
TT8: n = 8

Formulation of mRAA-loaded TT LLNS. TT2-TT8 were formulated with the helper lipid (1,2-distearoyl-sn-glycero-3-phosphocholine (DSPC), 2-dioleoyl-sn-glycero-3-phosphoethanolamine (DOPE) or 1-palmitoyl-2-oleoyl-sn-glycero-3-phosphoethanolamine (POPE)), cholesterol, 1,2-dimyristoyl-sn-glycerol, methoxypolyethylene glycol (DMG-PEG$_{2000}$) (molar ratio 50/10/38.5/1.5 or based on the orthogonal design Table 2 or Table 4) and FLuc mRNA via pipetting for in vitro studies or via a microfluidic based mixing device (Precision NanoSystems) for in vivo studies (Marks, J. R. et. al. $J. Am. Chem. Soc.$ 2011, 133, 8995-9004). After formulation, the freshly formed snRNA-LLNs were used immediately for cell transfection. For in vivo studies, the freshly prepared LLNs were then dialyzed against PBS buffer using Slide-A-Lyzer dialysis cassettes (3.5 K MWCO, Life Technologies, Grand island, N.Y.). Particle size and zeta potential of LLNs were measured using a NanoZS Zetasizer (Malvern, Worcestershire, U.K.) at a scattering angle of 173° and a temperature of 25° C.

Entrapment efficiency of LLNs was determined using the Ribogreen assay reported previously (Love Kevin, T. et. al. *Proc. Natl. Acad. Sci. U.S.A.* 2010, 107, 1864-1869; Chen, D. et. al. *J. Am. Chem. Soc.* 2012, 134, 6948-6951).

TT LLNs-Mediated Luciferase Transfection Assay. The human hepatocellular carcinoma cell line Hep3B was purchased from American Type Culture Collection (Manassas, Va.) and maintained at 37° C. with 5% $CO_2$ in Eagle's Minimum Essential Medium (MEM) supplemented with 10% heat inactivated FBS. Hep3B cells were seeded ($2 \times 10^4$ cells per well) into each well of white 96-well plates in 150 μL of culture medium, allowed to attach overnight in growth medium, and transfected by addition of 20 μL, of FLuc mRNA-loaded TT LLNs to growth medium. Transfections were performed in triplicate. After 6 h of transfection, culture medium containing TT LLNs was carefully removed, and 50 μL of serum-free EMEM and 50 μL of Bright-Glo luciferase substrate were mixed and added to each well. Five minutes later, the relative luminescence intensity was measured with the SpectraMax M5 microplate reader (Molecular Devices, LLC., Sunnyvale, Calif.). Free Flue mRNA served as a negative control.

Orthogonal Array Experimental Design. In order to identify a preferred molar ratio of the formulation components, an orthogonal array experiment design was utilized. Four formulation components were assigned in the following orthogonal experiments with a fixed TT/mRNA ratio (10/1). TT3S-DOPE LLNs 1-1 to 1-16 were prepared according to the orthogonal array design table $L_{16}(4)^4$ and used to transfect Hep3B cells (Table 2). The average luminescence intensity ($K_n$) of each factor in the same level (n=1, 2, 3, and 4) and the difference (ΔK) between the highest and lowest values of each factor were used to evaluate the impact of the levels and factors to the transfection efficiency, respectively. On the basis of the result of the first round of nanoparticle formulation, the levels of each factor were further refined, and the second round orthogonal experiment with 16 formulations TT3-DOPE LLNs 2-1 to 2-16 was conducted (Table 4). A similar analysis was performed as described above.

Cryo-Transmission Electron Microscopy (Cryo-TEM). Cryo-TEM samples were prepared by applying a small aliquot (3 μL) of O-TT3 LLNs to a specimen grid. After blotting away excess liquid, the grid was immediately plunged into liquid ethane to rapidly form a thin film of amorphous ice using Vitrobot Mark IV system (FEI, Hillsboro, Oreg.). The grid was transferred under liquid nitrogen in cryo-transfer station to a Gatan 626 cryo-transfer holder (Gatan, Pleasanton, Calif.). Cryo-transfer holder was loaded to a Tecnai F20 S/TEM (FEI, Hillsboro, Oreg.) and maintained at −173° C. Cryo-TEM images were recorded under low dose conditions at a magnification of 18500× on a postcolumn 1k×1k CCD camera.

Cytotoxicity Assay. Hep3B cells were grown in 96-well plates in 150 μL of medium 24 h prior to treatment at a density of $2 \times 10^4$ cells/well, After 6 h incubation with free FLuc mRNA or LLNs, 17 μL of MTT (5 mg/mL solution in PBS) was added to each well and the cells were then incubated for 4 h at 37° C. Then the medium was removed, and 150 μL of dimethyl sulfoxide was added. After shaking for 10 min, the absorbance at a wavelength of 570 nm was measured on a SpectraMax M5 microplate reader. Cell viability of TT LLNs was normalized by untreated cells.

Cellular Uptake of O-TT3 LLNs. Cells were plated on sterile glass coverslips (22 mm) in a 6-well plate at $8 \times 10^4$ cells/well. After overnight culture, cells on the coverslips were treated with PBS. Alexa-Fluor 647-labeled RNA or O-TT3-LLN containing nue, mRNA and Alexa-Fluor 647-labeled RNA (weight ratio 1/1) for 3 h. Cells were then rinsed three times with PBS and fixed with 4% formaldehyde for 10 min at RT. After washing twice with PBS, cells were incubated with Alexa-Fluor 488 conjugate of wheat germ agglutinin (1 μg/μL) and NucBlue fixed cell ready probes DAPI at RT for 10 min to stain membranes and nucleus. The cells were finally mounted onto glass slides (75×25 mm) with a drop of ProLong diamond antifade mountant reagent. All images were acquired using an ECLIPSE Ti inverted fluorescence microscopy (Nikon, Japan).

Biodistribution of O-TT3 LLNs. All procedures used in animal studies conducted at The Ohio State University were approved by the Institutional Animal Care and Use Committee (IACUC) and were also consistent with local, state and federal regulations as applicable. C57BL/6 mice (6-8 weeks old from the Jackson Laboratory) were administered intravenously via tail vein injection of free FLuc mRNA, C12-200-DSPC LLNs, TT3-DSPC LLNs, or O-TT3 LLNs at a dose of 0.5 mg/kg (mRNA concentration, n=3). After 6 h, mice were i.p. injected with 150 μL of the D-luciferin substrate (30 mg/mL) and euthanized in a $CO_2$ chamber 8 min after injection. Bioluminescence signals in the dissected liver, spleen, kidney, heart and lung were immediately measured using a Xenogen IVIS imaging system (Caliper, Alameda, Calif.), and signal strength of individual tissues was normalized against tissue weight.

In Vivo hFIX Expression and Histological Analysis. (Day, S. M. et. al. *Thromb. Haemostasis* 2004, 92, 486-494) C57BL/6 mice were administered intravenously via tail vein injection with free hFIX mRNA, O-TT3 FLuc (an irrelevant mRNA-loaded LLNs as a control), or O-TT3 hFIX at the indicated dosage. Six hours post administration, blood samples were collected and mixed with an anticoagulant solution (3.2% sodium citrate anticoagulant containing 0.17 mg/mL of corn trypsin inhibitor) in a ratio of 9:1, which was then centrifuged for 15 min at 2500 g. hFIX protein level was measured by enzyme-linked immunosorbent (ELISA) assay. Briefly, a 96-well immunoplate was coated overnight at 4° C. with 50 μL/well of mouse anti-hFIX antibody (1:1000 dilution) in 100 mM of bicarbonate/carbonate coating buffer (pH 9.2). After blocking with 200 μL of 6% BSA at RT for 3 h, each well was incubated with 50 μl of diluted mouse serum at RT for 2 h. Human FIX bounded to the wells was detected by incubating with 100 μL goat anti-hFIX HRP antibody diluted 1:4000 at RT for 1 h. After that, 100 μL of substrate O-phenylenediaminedihydrochloride at 2 mg/mL was added at RT for 8 min and then the reaction was immediately stopped by adding 50 μL of 3 M $H_2SO_4$. The absorbance at 492 nm was determined using the SpectraMax 5 microplate reader. Levels of human FIX were calculated through a standard curve generated from the standard human FIX. The same protocol was used for FIX-knockout mice. Additionally, hFIX bioactivity was determined by using a chromogenic kit according to the manufacturer's protocol (Rossix, Molndal, Sweden). Histopathology on the heart, kidney, liver, lung, and spleen were processed, stained with hematoxylin and eosin (H&E), and imaged using an ECLIPSE Ti inverted fluorescence microscopy (Nikon, Japan).

General Synthetic Procedures and Spectral Data

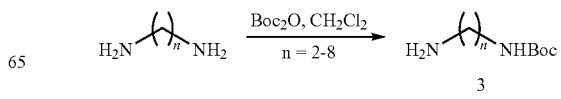

3

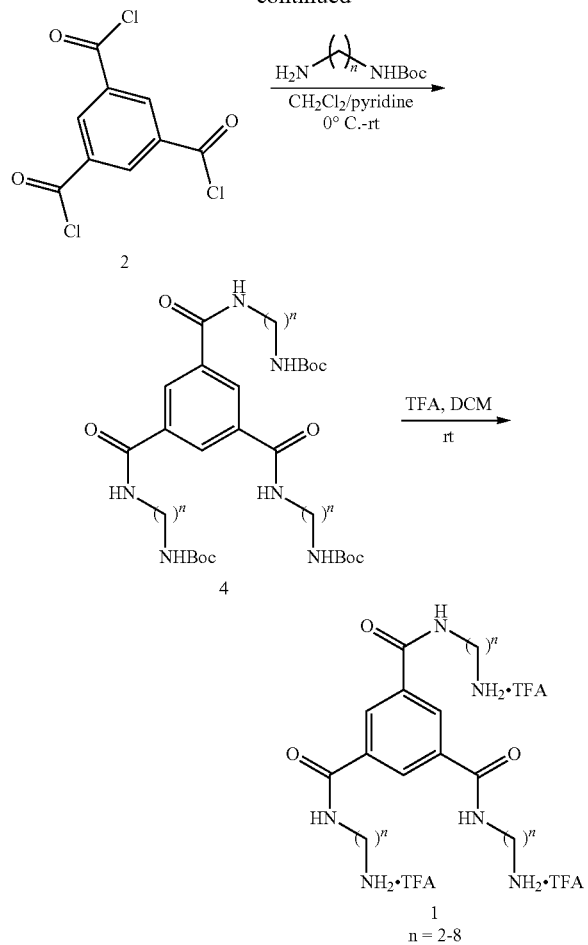

Synthesis of compound 3. To a solution of diamine (75 mmol) in CHCl$_3$ (70 mL) was added a solution of Boc$_2$O (14.4 mmol) in CHCl$_3$ (30 mL) via an additional funnel over 2.5 h. The resulting suspension was stirred and 100 mL of NaHCO$_3$ (1N) was slowly added to form a bi-layer solution. The organic layer was washed with 100 mL of 1N NaHCO$_3$ and 20 mL of brine, and then dried over solid MgSO$_4$ for 2 h. The solution was then filtered, evaporated and dried under high vacuum in order to afford compound 3. Yield: n=2, 91%; n=3, commercially available reagent; n=4, 63%; n=5, 95%; n=6, commercially available reagent; n=7, 95%; n=8, 86%.

Synthesis of compound 4. (See Matsuura, K.; Murasato, K. Kimizuka, N. *J. Am. Chem. Soc.* 2005, 127, 10148-10149). To a solution of compound 2 (1.88 mmol) in CH$_2$Cl$_2$ (30 mL) was added 10 mL of pyridine and cooled in an ice bath. A solution of compound 3 (7.52 mmol) in CH$_2$Cl$_2$ (30 mL) was added dropwise with stirring. The reaction mixture was then allowed to warm to RT, diluted with 100 mL of CH$_2$Cl$_2$ and washed twice with 50 mL of water, 50 mL of saturated NaHCO$_3$, and 50 mL of brine. The solution was dried over solid MgSO$_4$ for 2 h and concentrated. The residue was purified by column chromatography using a CombiFlash Rf system with a RediSep Gold Resolution silica column (Teledyne Isco) with gradient elution from 100% CH$_2$Cl$_2$ to CH$_2$Cl$_2$/MeOH/NH$_4$OH (75/22/3 by volume) to give compound 4. Yield: n=2, 74%; n=3, 68%; n=4, 65%; n=5, 69%; n=6, 81%; n=7, 37%; n=8, 61%.

Synthesis of compound 1. To a suspension of compound 4 (1.41 mmol) in CH$_2$Cl$_2$ (20 mL) was added trifluoroacetic acid (TFA, 1.41 mmol). The mixture was stirred at RT for 1 h and monitored with thin layer chromatography (TLC). Upon completion of the reaction, the solvent was evaporated and the residue was dissolved in MeOli and concentrated. After solidification in EtOAc, compound 1 was dried under an oil pump and afforded in quantitative yield.

$^1$H NMR spectra were recorded at 300 or 400 MHz on the Bruker instrument. $^1$H NMR chemical shifts were reported as δ values in ppm relative to TMS. Mass spectra were obtained on a Micromass Q-TOF micro Mass Spectrometer.

$N^1,N^3,N^5$-tris(2-(didodecylamino)ethyl)benzene-1,3,5-tricarboxamide (TT2): yield (82%). $^1$H NMR (300 MHz, CDCl3, δ) 8.88 (3H, br), 8.56 (3H, s), 3.81 (6H, in), 3.32 (6H, m), 3.04-3.08 (12H, m), 1.69 (12H, s), 1.20-1.30 (108H, m), 0.88 (18H, tri, J=6.9 Hz). MS (m/z): [M+H]$^+$ calcd. for C$_{87}$H$_{169}$N$_6$O$_3$, 1346; found, 1346.

$N^1,N^3,N^5$-tris(3-(didodecylamino)propyl)benzene-1,3,5-tricarboxamide (TT3): yield (50%). $^1$H NMR (300 MHz, CDCl3, δ) 8.53 (3H, br), 8.40 (3H, s), 3.57 (6H, m), 2.67-3.60 (6H, tri, J=5.4 HZ), 2.58-2.48 (12H, tri, J=7.5 Hz), 1.90-1.70 (12H, m), 1.57-1.38 (12H, m), 1.35-1.17 (96H, 0.89 (18H, tri, J=6.9 Hz). MS (m/z) [M+H]$^+$ calcd. for C$_{90}$H$_{175}$N$_6$O$_3$, 1388; found, 1388.

$N^1,N^3,N^5$-tris(4-(didodecylamino)butyl)benzene-1,3,5-tricarboxamide (TT4): yield (31%). $^1$H NMR (300 MHz, CDcl3, δ) 8.33 (3H, s), 7.39 (3H, br), 3.5-3.42 (6H, m), 2.65-2.46 (18H, m), 1.75-1.55 (12H, m), 1.52-1.37 (12H, m), 1.35-1.17 (102H, m), 0.90 (18H, tri, J=6.9 Hz). MS (m/z): [M+H]$^+$ calcd. for C$_{93}$H$_{81}$N$_6$O$_3$, 1430; found, 1430.

$N^1,N^3,N^5$-tris(5-(didodecylamino)pentyl)benzene-1,3,5-tricarboxamide (TT5): yield (45%). $^1$H NMR (300 MHz, CDCl3, δ) 8.40 (3H, s), 6.62 (3H, s), 3.56-3.45 (6H, m), 2.47-2.39 (18H, m), 1.76-1.65 (18H, m), 1.52-1.37 (24H, m), 1.35-1.20 (90H, m), 0.89 (18H, tri, J=6.9 Hz). MS (m/z): [M+H]$^+$ calcd. for C96H$_{187}$N$_6$O$_3$, 1472; found, 1472.

$N^1,N^3,N^5$-tris(6-(didodecylamino)hexyl)benzene-1,3,5-tricarboxamide (TT6): yield (53%). $^1$H NMR (300 MHz, CDCl3, δ) 8.38 (3H, s), 6.52 (3H, br), 3.52-3.45 (6H, m), 2.47-2.39 (18H, m), 1.72-1.63 (18H, m), 1.54-1.36 (30H, m), 1.32-1.21 (90H, m), 0.90 (18H, tri J=6.9 Hz), MS (m/z): [M+H]$^+$ calcd. for C$_{99}$H$_{193}$N$_6$O$_3$, 1515; found, 1515.

$N^1,N^3,N^5$-tris(7-(didodecylamino)heptypbenzene-1,3,5-tricarboxamide (TT7): yield (75%). $^1$H NMR (300 MHz, CDCl3, δ) 8.40 (3H, s), 6.72 (3H, s), 3.48 (6H, m), 2.50 (18H, m), 1.70-1.56 (6H, m), 1.55-1.34 (30H, m), 1.37-1.27 (108H, m), 0.89 (18H, tri, J=6.9 Hz). MS (m/z): [M+H]$^+$ calcd. for C$_{102}$H$_{199}$N$_6$O$_3$, 1557; found, 1557.

$N^1,N^3,N^5$-tris(8-(didodecylamino)octyl)benzene-1,3,5-tricarboxamide (TT8): yield (quantitative). $^1$H NMR (300 MHz, CDCl3, δ) 8.40 (3H, s), 6.86 (3H, br), 3.47 (6H, m), 2.82-2.52 (18H, m), 1.73-1.42 (30H, m), 1.42-1.17 (120H, m), 0.90 (18H, tri, J=6.9 Hz). MS (m/z): [M+H]$^+$ calcd. for C$_{105}$H$_{205}$N$_6$O$_3$, 1599; found, 1599.

Example 2. Comparison of of 1,3,5-triazinane-2,4, 6-triose Derivatives LLNs to $N^1,N^3,N^5$-tris(2-aminoethyl)benzene-1,3,5-tricarboxamide Lipid-Like Nanoparticles (LLNs)

In this example, the use of 1,3,5-triazinane-2,4,6-trione derivatives (TNT) lipid like-particles was compared to the TT particles ($N^1,N^3,N^5$-tris(2-aminoethyl)benzene-1,3,5-tricarboxamide—discussed in Example 1). Scheme 2 and 3 show the generic synthetic routes of designed LLN. Compound 1 with various terminal epoxides underwent ring opening reactions to give compound TNT-a-d. Reductive amination reactions between 2 and various aldehydes afforded the desired compound TBT-2-8 (Scheme 3—note that TBT and TT refer to the same structures)

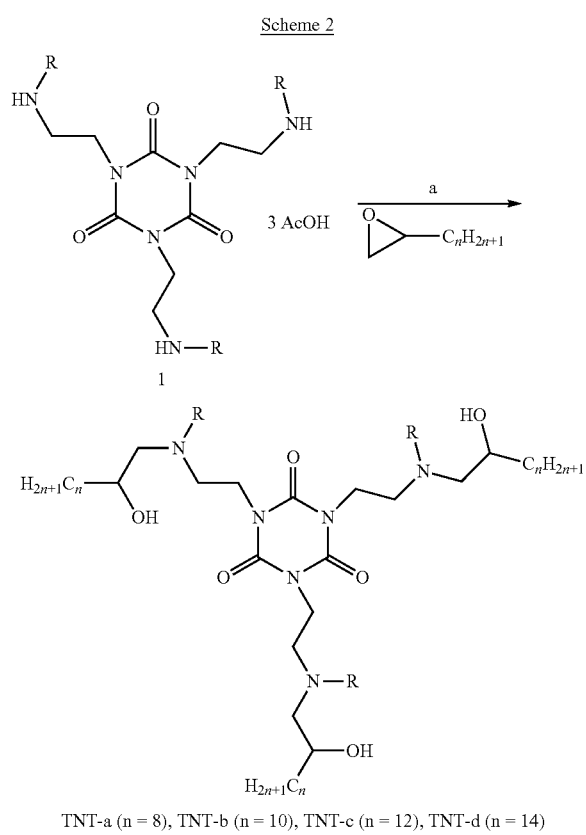

Scheme 2

TNT-a (n = 8), TNT-b (n = 10), TNT-c (n = 12), TNT-d (n = 14)

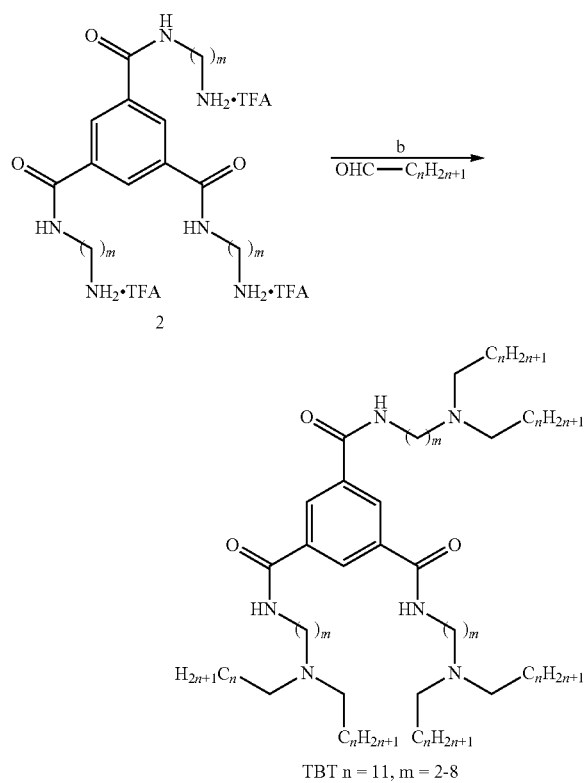

Scheme 3

TBT n = 11, m = 2-8

Figure 15:
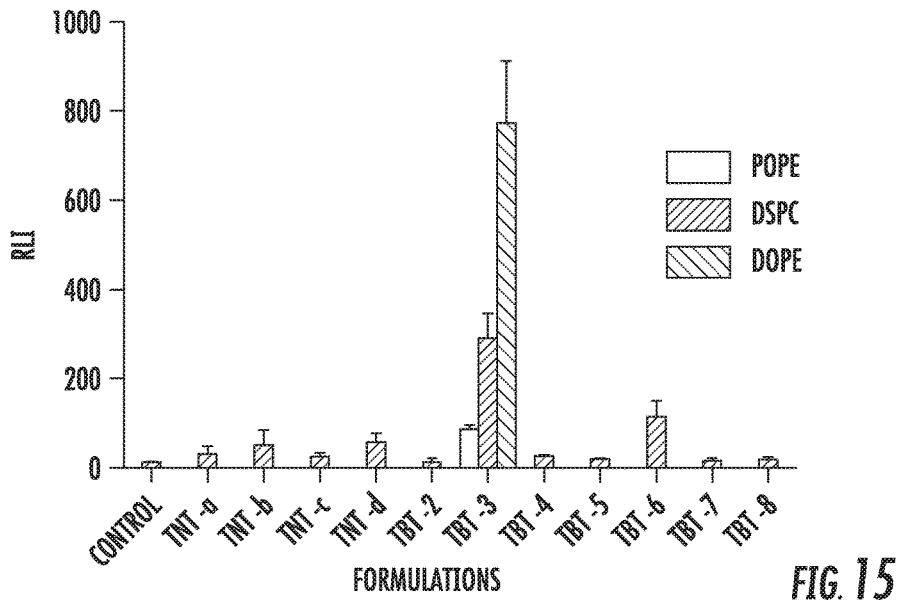
FIG. 15. In vitro expression of luciferase in Hep3B cells with formulated TNT-a to TNT-d and TBT-2 to TBT-8.
Figure 16:
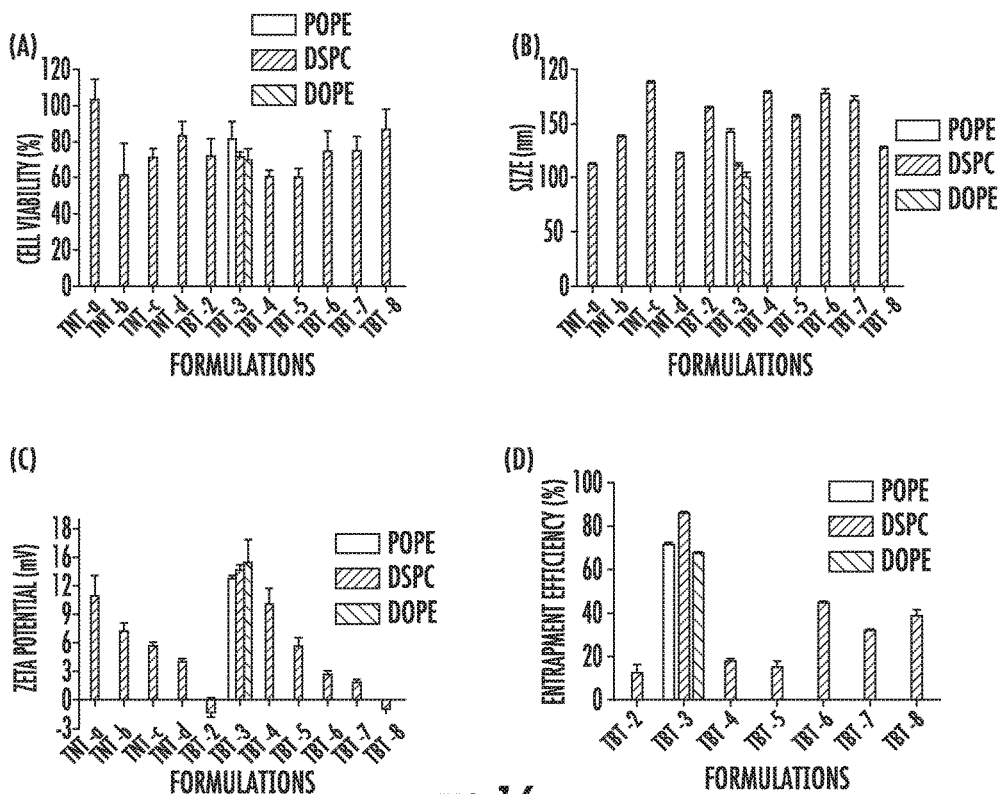
FIG. 16. The cytotoxicity (A), particle size (B), zeta potential (C) and entrapment efficiency (D) of formulated TNT-a to TNT-d and TBT-2 to TRT-8.

Screening of LLN:

TNT-a to TNT-d and TBT-2 to TBT-8 were evaluated with an in vitro luciferase transfection assay. These materials were first formulated with DSPC, cholesterol, PEG2K-C14, and mRNA encoding luciferase. TBT-3 displayed significant expression of the firefly luciferase protein in Hep3B cells (FIG. 15), whereas the TNT structures did not display significant expression of luciferase. The cytotoxicity, particle size, zeta potential and entrapment efficiency were also measured (FIG. 16).

Example 3. Use of Lipid-Like Nanoparticles (LLNs) in a Gene-Editing System for Hemophilia B Hemophilia is an inherited genetic disorder with an incidence of 1:5000 live born males (Coppola A, et al. Journal of blood medicine. 2010; 1:183-95; Monahan P E, et al. Current opinion in hematology. 2002; 9(5):430-6; Sabatino D E, et al. Animal models of hemophilia. Progress in molecular biology and translational science. 2012; 105: 151-209). The disorder affects an estimated 20,000 patients in the US and over 400,000 patients worldwide, one quarter of which is affiliated with hemophilia B (HB) due to FIX mutations. Patients with hemophilia suffer life-threatening bleeding complications and debilitating joint diseases. Based on the level of clotting factor activity, HB is usually classified into three groups: mild hemophilia B (6% up to 40% of FIX in the blood); moderate hemophilia B (1% to 5% of FIX in the blood); severe hemophilia B (<1%). Current therapy is to infuse FIX protein concentrates in order to treat or to prevent bleeding. Yet, approximately 75% of patients with hemophilia have limited or no access to treatment. Moreover, therapeutic efficacy has always been hampered by the development of antibodies against FIX in 30% of patients with severe HB. Therefore, new treatment strategies are in urgent demand in order to improve therapeutic benefits and patient compliance.

Genome engineering holds enormous potential for treating a wide variety of genetic disorders (Kim H, Kim J S. Nat Rev Genet. 2014; 15(5):321-34; Damian M, Porteus Mol Ther. 2013; 21 (4):720-2). A number of genome editing technologies have emerged in the past decade, including zinc-finger nucleases (ZFNs), transcription activator-like effector nucleases (TALENs), and the RNA-guided CRISPR/Cas nuclease system. The first two technologies use a strategy of tethering endonuclease catalytic domains to DNA binding proteins for inducing targeted DNA double-stranded breaks (DSBs) at specific genomic loci.

CRISPR is an abbreviation of clustered, regularly interspaced, short palindromic repeats (CRISPR), which is part of adaptive immunity in bacteria and archaea. The CRISPR genomic loci encode the Cas9 endonuclease, which forms a targeted RNA-guided endonuclease with specific RNA (sgRNA) complex (Shalem, et al. Science. 2014; 343(6166): 84-7; Chen S, et al. Cell. 2015; 160(6):1246-60; Mali P, et al. Nat Methods. 2013; 10(10):957-63; Mali P, et al. Science. 2013; 339(6121):823-6; O'Connell M R, et al. Nature. 2014; 516(7530):263-6; Ran F A, et al. Nature. 2015; 520(7546): 186-91; Ran F A, et al. Cell. 2013; 154(6):1380-9; Sander J D, Joung J K. 2014; 32(4)347-55; Sternberg S H, et al. Nature. 2014; 507 (7490):62-7; Yin H, et al. Nat Biotechnol, 2014; 32(6):551-3). Cas9/sgRNA recognizes the protospacer-adjacent motif (PAM) sequence and the complementary 20 nucleotide genomic sequence. Cas9 cuts approximately 3 nucleotides upstream of the PAM in order to induce double-stranded DNA breaks (DSBs), which are repaired by error-prone non-homologous end-joining (NHEJ) or precise homology-directed repair (HOR), Compared to ZFNs and TALENs, the CRISPR/Cas nuclease system is easy to design, highly specific, and well-suited for high throughput and multiplexed gene editing for a variety of cell types and organisms (Kim H, Kim J. Nat Rev Genet. 2014; 15(5):321-34; Damian M, Porteus M H Mol Ther, 2013; 21 (4):720-2).

Efficient delivery of the components of Cas9/sgRNA can induce gene cutting at the mutated gene site and correct specific gene mutations, achieving a cure of genetic disorders. However, the challenge is formidable and poses important challenges, including efficiency specificity, and safety. Current repair rate is less than 1% of total cells with mutations reported in the literature. Therefore, improvements in the delivery of the Cas9/sgRNA system are required for potential clinical therapeutic application of genome editing for gene corrections. Delivery of plasmid-encoding Cas9 through hydrodynamic injection and AAV vectors has been demonstrated in the literature and has successfully corrected mutated genes in mouse models (Hsu P D, et al. Nat Biotechnol. 2013; 31 (9):827-32; Zuris J A, et al. Nat Biotechnol. 2015; 33(1):73-80). However, potential DNA damage is a significant safety issue if Cas9 is present for an extended period of time. Recently, messenger RNA (mRNA) therapeutics has demonstrated a potential for expressing functional proteins (Tavernier G, et al. J Control Release. 2011; 150(3):238-47; Pascolo S. et al. Handb Exp Pharmacol. 2008(183):221-35; Phua K K, et al, J Control Release. 2013; 166(3):227-33; Mcivor R S. Mol Ther. 2011; 19(5):622-3; Sahin U, et al. Nat Rev Drug Discov. 2014; 13(10):759-60; Su X, et al. Mol Pharm. 2011; 8(3):774-87). Hence, Cas9 protein can be translated through a non-viral delivery of Cas9 mRNA, which would allow for the short-term expression and eventually complete clearance of the nuclease from the body.

In this example, lipid nanoparticles and AAV vectors are used for the delivery of Cas9/sgRNA system. Lipid nanoparticles deliver mRNA encoding Cas9 and express Cas9 protein. AAV vectors express gRNA and provide repair template DNA. Combination of the two delivery tools as a gene editing system maximizes delivery efficiency and minimizes potential toxicity.

Methods
Synthesis and Characterization of Lipid Nanoparticles

Lipid and lipid-like materials have shown great promise for RNA delivery. The objective of this aim is to develop new lipids with high triRNA delivery efficiency and low toxicity. Thus, N1,N3,N5-tris(2-aminoethyl)benzene-1,3,5-tricaboxamide (TBT (also referred to as TT in Example 1 above)) derivatives (Scheme 4) were designed. These compounds are composed of a phenyl ring, an amide linker, and three amino lipid chains. TBT-E series are biodegradable with an ester bond in the structure.

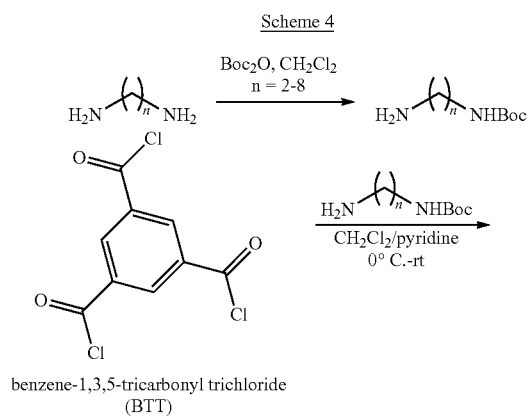

Scheme 4

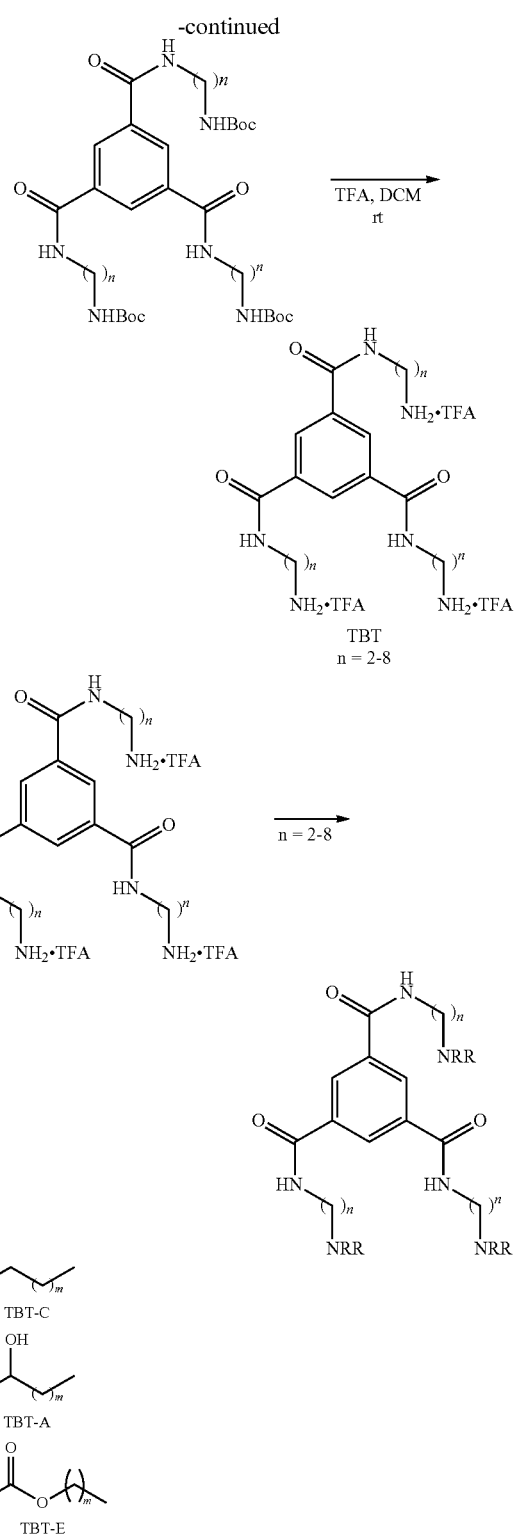

TBT lipids (see TT lipids discussed in Example 1) are synthesized with three types of lipid tails on the TBT backbones including carbon chains, hydroxyl and ester groups (TBT-C, TBT-A, TBT-E). The two substrates (TBT and functional lipids) undergo ring-opening reactions, reductive amination, or Michael addition reactions (Love Kevin T, et al. Proc Natl Acad Sci USA. 2010; Akins A, et al. Nat Biotech. 2008; 26(5):561-9). The reaction solution is concentrated with silica gel and purified using flash chromatography in order to afford the desired products. Structures of new lipids are confirmed by nuclear magnetic resonance (NMR) and mass spectrometry.

Example 4. $N^1,N^3,N^5$-tris(2-aminoethyl)benzene-1,3,5-triearboxamide LLNs and Gene Editing In Vitro The top LLN formulations are used to evaluate their delivery efficiency of mRNA encoding Cas9 via a well-established western blot assay. The best $N^1,N^3,N^5$-tris(2-aminoethyl)benzene-1,3,5-tricarboxamide (TT or TBT) formulation is utilized to quantify the percentage of gene cutting using a Hep3B reporter cell line stably expressing a GFP reporter and a GFP targeting sgRNA (sgGFP). Cells are transfected with TBT and AAV vector encoding sgGFP. Cutting of GFP gene causes the loss of GFP signal, which is measured by fluorescence-activated cell sorting analysis (FACS). A T7E1 assay is used to quantify the percentage of gene cutting.

Example 5. Gene Editing Efficiency and Safety Profiles in a Hemophilia B Mouse Model Delivery efficiency of mRNA encoding Cas9 in C57BU6 mice is measured. Briefly, eight-week-old female C57BL/6 mice are classified into four groups: PBS, mRNA alone, lipid alone, and lipid-mRNA groups (5 animals per group). The dose is determined from in vitro potency. After administration, liver Cas9 protein levels at different time points (at 4, 8, 12 and 24 hr) are measured by western blot (Barzel A. et al. Nature, 2015; 517(7534):360-4). Biodistribution of the top-performing material is also measured. C57BL/6 mice is administered intravenously via tail vein injection for luciferase mRNA expression experiments. The mice are sacrificed at the time point from the above studies; the pancreas, spleen, liver, kidneys, ovaries/uterus, heart, lungs, and thymus as well as a section of the adipose tissue and muscle tissue is then dissected. The tissues is examined with an IVIS imaging system from Caliper.

Figure 17:
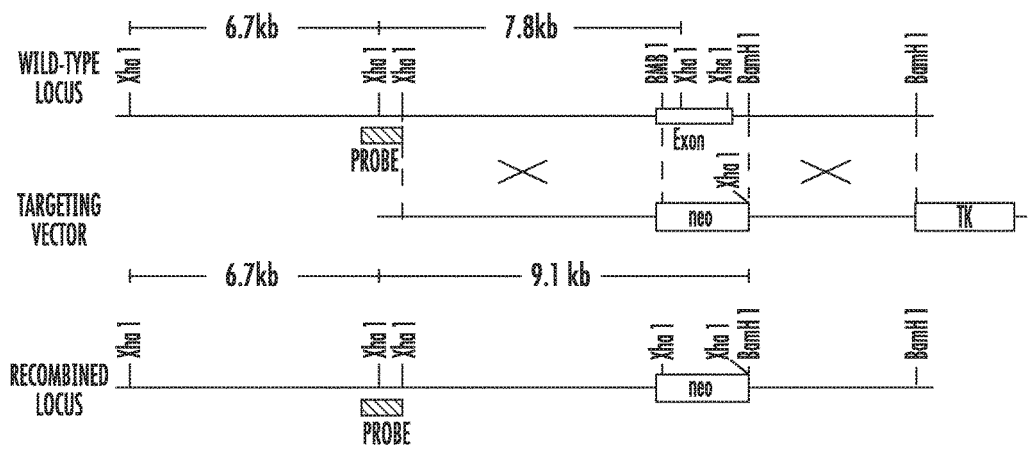
FIG. 17. A schematic illustration of a hemophilia B mouse model. A portion of the mouse factor IX gene showing the last exon, the targeting vector, and the expected recombined locus is depicted. The targeting construct contains a PGK-neo cassette, flanked by DNA fragments upstream and downstream the putative exon 8. The predicted product of successful homologous recombination is shown at the bottom.
Figure 18:
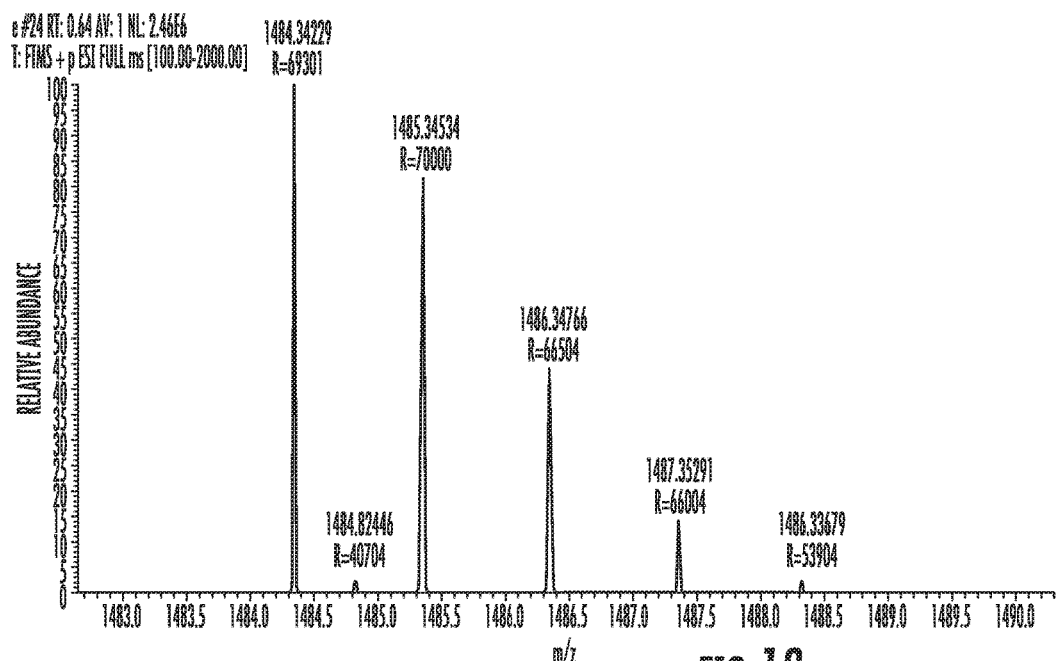
FIG. 18. Mass spectrometry analysis of compound III-1.
Figure 19:
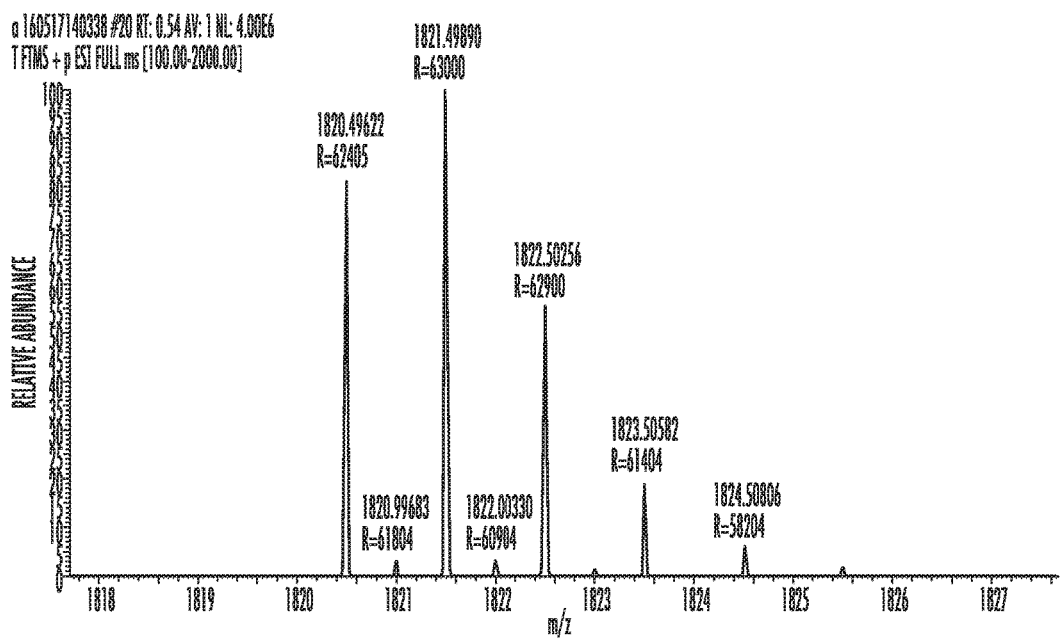
FIG. 19. Mass spectrometry analysis of compound IV-1.

A hemophilia B mouse model has been established (FIG. 17). AAV vector is constructed using Gibson assembling. AAV9 virus is prepared and purified. In order to determine whether lipid nanoparticles can deliver Cas9 mRNA in HB mice, after tail vein injections of Cas9 mRNA nanoparticles, the expression level of Cas9 protein in total liver lysates is measured by western blot. To measure the half-life of Cas9 mRNA in vivo, total RNA of liver is extracted and measured by qPCR.

CRISPR design and analysis is performed using the website http://crispr.mit.edu developed by Dr. Feng Zhang at MIT. An AAV9 vector has been designed with a U6-sgRNA expression cassette and an HOR template (AAV9-HOR). In order to investigate whether combination of $N^1,N^3,N^5$-tris(2-aminoethyl)benzene-1,3,5-tricarboxamide (TT or TBT) and AAV9-HOR is able to induce gene cutting in vivo, these are administered in the hemophilia B mice (n=5 for each group including PBS, AAV9-HOR, TBT, and TBT/AAV9-HOR). These mice possess a PGK-neo cassette at the last exon of FIX (corresponding to human factor IX exon 8), coding for a large portion of the catalytic domain of factor IX (FIG. 17). To enable repair of the FIX gene, an AAV vector is designed with a U6-sgRNA expression cassette and an HOR template (AAV9-HOR), which consists of about 1.0 kb homologous sequence to the FIX genomic region on each side of the PGK-neo cassette (FIG. 17).

These are packaged using an AAV9, which has shown the highest efficiency to target the liver compared to other AAV subtypes (Zincarelli C, et al. Mol Ther. 2008; 16(6):1073-80). 7 days after administration, efficacy is evaluated in HB mice using a number of bioassays including: a tail-bleeding model, whole blood rotation thromboelastometry (ROTEM), activated partial thromboplastin time (aPTT), and platelet-poor plasma (PPP) thrombin generation assays (Barzel A. et al. Nature, 2015; 517(7534):360-4; Suwanmanee T, et al. Mol Ther. 2014; 22(3):567:74). In order to quantify gene repair rate in vivo, qRTLPCR is performed using primers spanning exons 8 and compare with wild type mice. To further examine genome editing in the liver, deep sequencing of the FIX locus in liver genomic DNA is conducted. The percentage of indels at predicted sgRNA target region in the group treated with TBT/AAV9-HDR is also measured.

In addition to efficacy, safety is an important factor for the application of gene corrections in human therapeutics. Cas9/sgRNA may cause indels at off-target genomic sites. In order to investigate potential off-target effects using TBT/AAV9-HDR system in vivo, a deep sequencing is conducted at the top five predicted off-target sites. To understand the potential toxicity and immunogenicity of the system, a single-dose and repeat dose tolerability study in mice is performed (Dong Y, et al. PNAS USA, 2014; 111 (11):3965-60). The clinical signs and body weight in treated groups compared to the control group is measured. Cytokine induction and serum chemistry parameters (alanine transaminase-ALT, aspartate transaminase-AST, and cholesterol) after administration of the materials is also measured (Dahlman J E et al. Nat Nanotechnol. 2014: 9(8):648-55). Lastly, the histology of tissue samples of treated groups in comparison to the control group is analyzed.

Briefly, C57BL/6 mice are administered with the top-performing material via tail vein injection. Blood and tissue samples are collected from the animals. Histopathology on liver, spleen, kidneys, heart, and lungs is processed and evaluated. Immunoassays are used to measure the levels of cytokines in a 96-well plate using Bio-Plea Prom™ assays formatted on magnetic beads. 30 different cytokines are analyzed: IL-1, IL-2, IL-3, IL-4, IL-5, IL-9, IL-10, IL-12 (p40), IL-12 (p70), Exotaxin. G-CSF, GM-CSF, IFN-y, KC, MCP-1, MIP-1a, MIP-1b, RANTES, TNG-a, IL-18, FGF-basic, LIF, MCSF, MIG, MIP-2, PDGF-bb and VEGF. Clinical chemistry of ALT, AST, and total bilirubin is measured by ELISA.

A T7E1 assay has been established to analyze the percentage of gene cutting. Cas9 and sgRNAs were transfected in vitro. After genome DNA preparation and PCR reactions, subsequent T7E1 assay was performed to check the cutting of the target gene. B11 and B12, two sgRNAs induced a percentage of 27.4% and 40.2% cutting, respectively (not shown). NC is negative control with a non-targeting sgRNA expressed.

Example 7. Delivery of mRNAs Using Compound TT3

Formulation of mRNA-loaded TT LLNs. TT3 was formulated with the helper lipid 1, 2-dioleoyl-sn-glycero-3-phosphoetha.nolamine (DOPE) cholesterol, 1,2-dimyristoyl-sn-glycerol, methoxypolyethylene glycol (DMG-PEG$_{2000}$) and FLuc mRNA or Cas9 mRNA via pipetting for in vitro studies or via a microfluidic based mixing device (Precision NanoSystems) for in vivo studies (Marks, J. R. et. al. *J. Am. Chem. Soc.* 2011, 133, 8995-9004). After formulation, the freshly formed mRNA-LLNs were used immediately for cell transfection. For in vivo studies, the freshly prepared LLNs were then dialyzed against PBS buffer using Slide-A-Lyzer dialysis cassettes (3.5 K MWCO, Life Technologies, Grand Island, N.Y.). Particle size and zeta potential of LLNs were measured using a NanoZS Zetasizer (Malvern, Worcestershire, U.K.) at a scattering angle of 173° and a temperature of 25° C. Entrapment efficiency of LLNs was determined using the Ribogreen assay reported previously (Love Kevin, T. et. al. *Proc. Natl. Acad. Sci. U.S.A.* 2010, 107, 1864-1869; Chen, D. et. al. *J. Am. Chem. Soc.* 2012, 134, 6948-6951).

Figure 20:
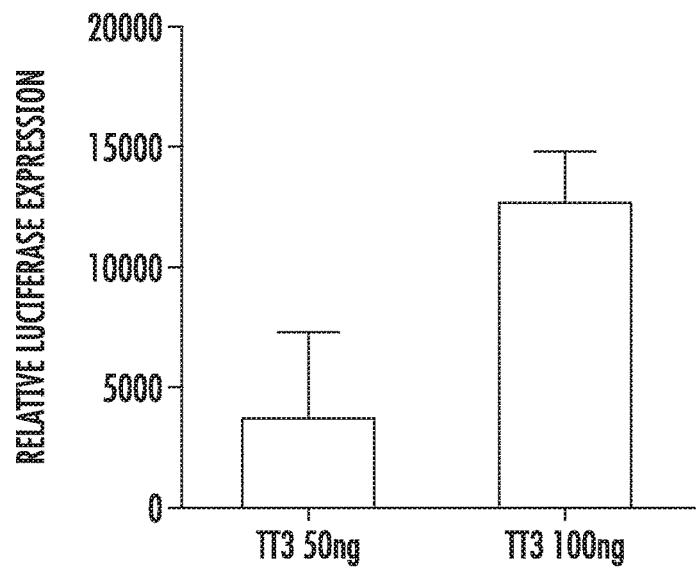
FIG. 20. TT3 LLNs deliver plasmid DNA encoding firefly luciferase.
Figure 21:
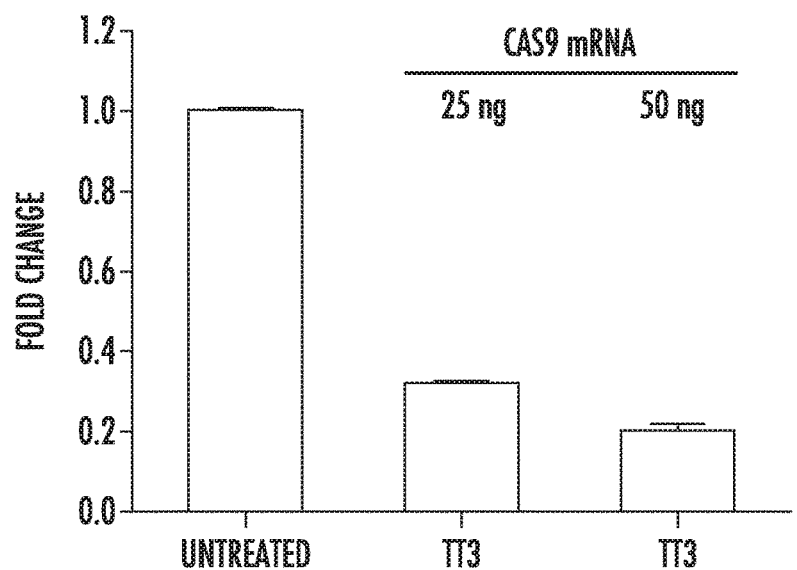
FIG. 21. TT3 LLNs deliver mRNA encoding Cas9.

TT LLNs-Mediated Transfection Assay. The human hepatocellular carcinoma cell line Hep3B was purchased from American Type Culture Collection (Manassas, Va.) and maintained at 37° C. with 5% $CO_2$ in Eagle's Minimum Essential Medium (EMEM) supplemented with 10% heat inactivated FBS. Hep3B cells were seeded ($2\times10^4$ cells per well) into each well of white 96-well plates in 150 μL of culture medium, allowed to attach overnight in growth medium, and transfected by addition of 20 μL of FLuc mRNA-loaded TT LLNs to growth medium. After 6 h of transfection, culture medium containing TT LLNs was carefully removed, and 50 μL of serum-free EMEM and 50 μL of Bright-Glo luciferase substrate were mixed and added to each well. Five minutes later, the relative luminescence intensity was measured with the SpectraMax M5 microplate reader (Molecular Devices, Sunnyvale, Calif.), Free FLuc mRNA served as a negative control (See FIG. 20). In FIG. 21, Cas9 mRNA was delivered via the O-TT3 LLN and the fold change in signal was examined to determine the DNA cleavage due to Cas9 delivery.

Example 8. Synthesis of Active Compounds

Scheme 5: Generic Synthetic Routes of Designed LLN

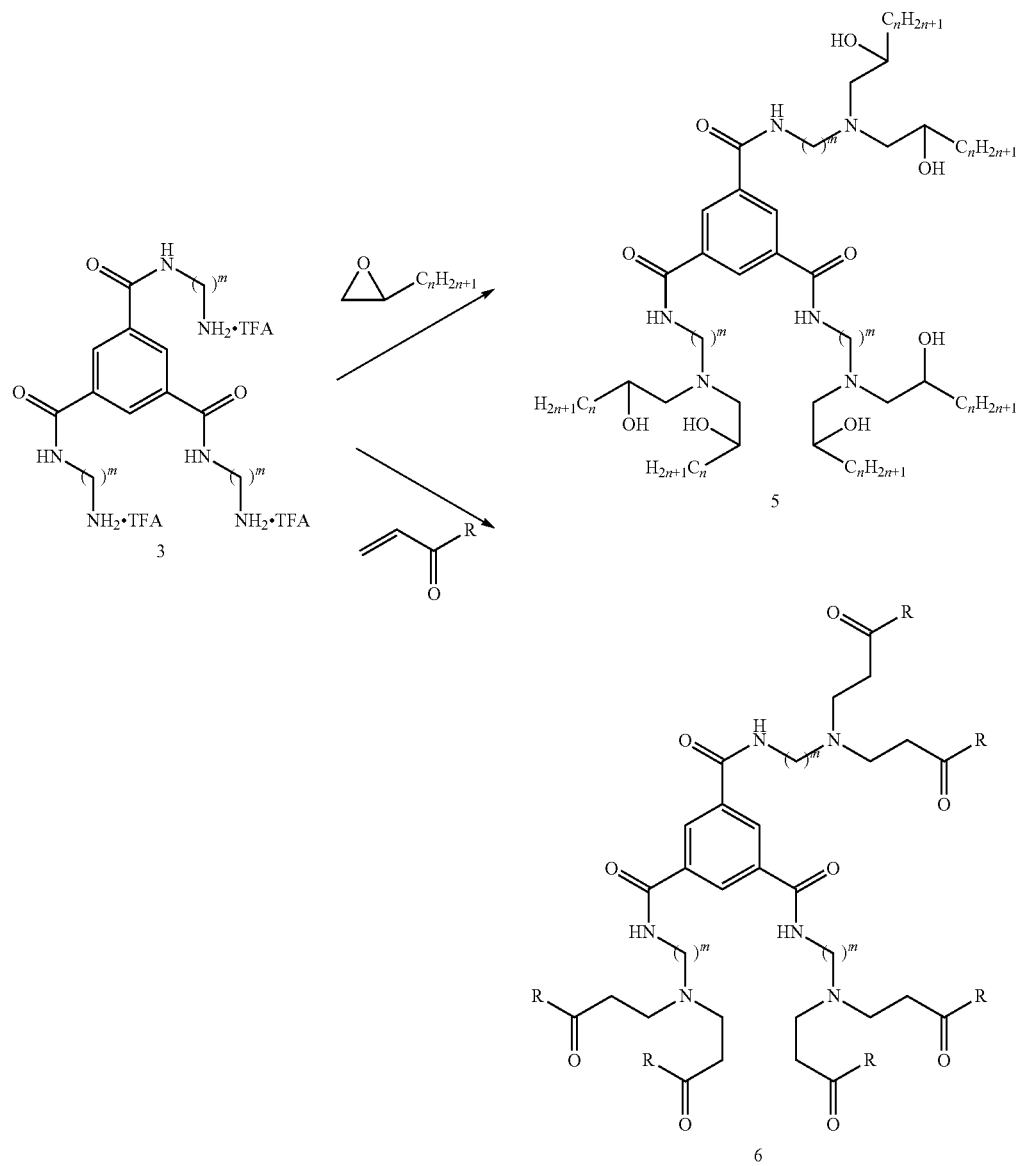

R = $OC_nH_{2n+1}$ or $NHC_nH_{2n+1}$

General Procedures for Reactions. To a mixture of starting materials was added triethylamine at room temperature. The reaction mixture was heated to 90 degree overnight. The reaction solution was concentrated with silica gel and purified using flash column chromatography.

Nonlimiting examples of LLN compounds, according to Scheme 5, include, but are not limited to:

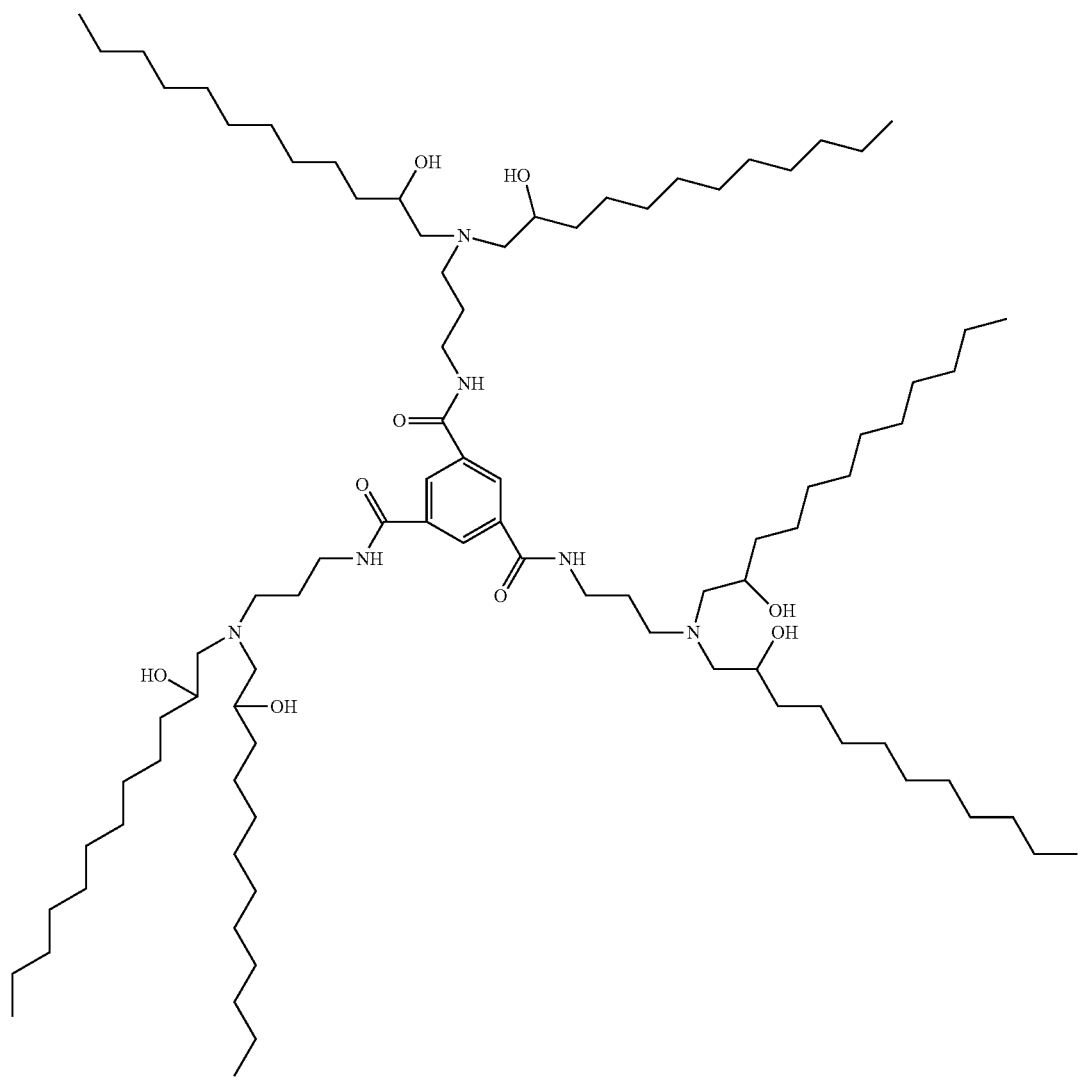

Compound III-1

Chemical Formula: $C_{90}H_{174}N_6O_9$
Exact Mass: 1483.3342

-continued

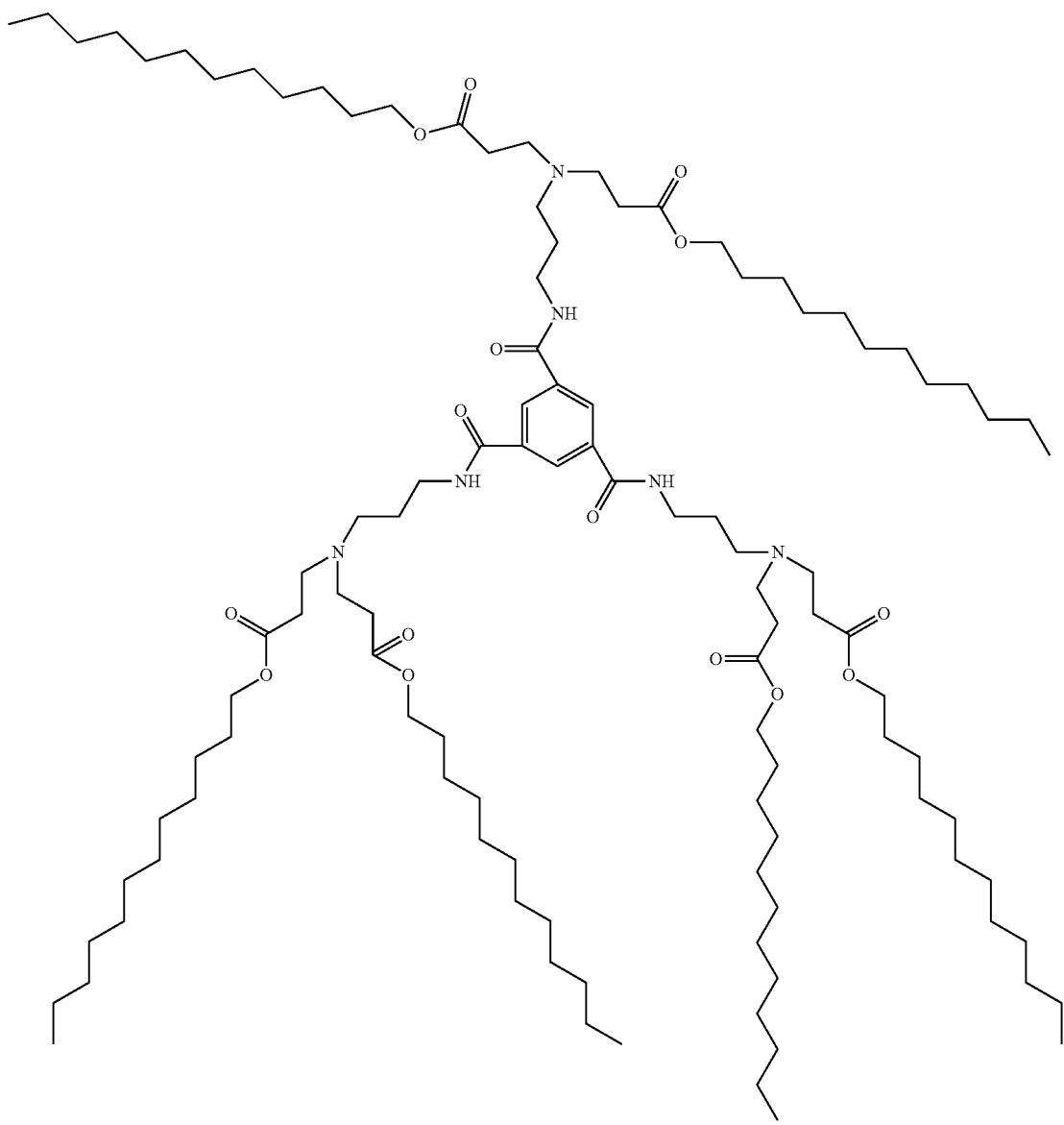 [SMILES: CCCCCCCCCCCCOC(=O)CCN(CCCNC(=O)c1cc(C(=O)NCCCN(CCC(=O)OCCCCCCCCCCCC)CCC(=O)OCCCCCCCCCCCC)cc(C(=O)NCCCN(CCC(=O)OCCCCCCCCCCCC)CCC(=O)OCCCCCCCCCCCC)c1)CCC(=O)OCCCCCCCCCCCC]

Compound IV-1

Chemical Formula: $C_{108}H_{198}N_6O_{15}$
Exact Mass: 1819.4915

Those skilled in the art will appreciate that numerous changes and modifications can be made to the preferred embodiments of the invention and that such changes and modifications can be made without departing from the spirit of the invention. It is, therefore, intended that the appended claims cover all such equivalent variations as fall within the true spirit and scope of the invention.

We claim:
1. A compound of Formula I:

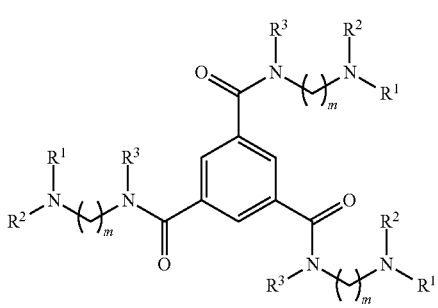

Formula I and salts thereof; wherein
each $R^1$ is independently unsubstituted alkyl;
each $R^2$ is independently unsubstituted alkyl;
each $R^3$ is independently hydrogen or substituted or unsubstituted alkyl; and
each m is independently 3, 4, 5, 6, 7, or 8;
wherein at least one $R^1$ is unsubstituted $C_{10-12}$ alkyl.

2. The compound of claim 1, wherein at least one $R^1$ is $C_{11}H_{23}$.

3. The compound of claim 1, wherein at least one $R^2$ is $C_{11}H_{23}$.

4. The compound of claim 1, wherein at least one $R^3$ is hydrogen.

5. The compound of claim 1, wherein at least one m=3.

6. The compound of claim 1, having the structure:

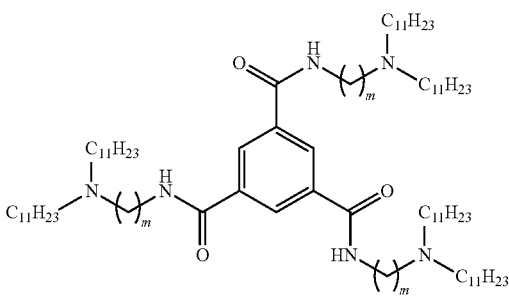

and salts thereof, wherein m=3.

7. The compound of claim 1, wherein at least one $R^1$ is $C_{12}H_{25}$.

8. The compound of claim 1, wherein at least one $R^2$ is $C_{12}H_{25}$.

9. The compound of claim 1, having the structure:

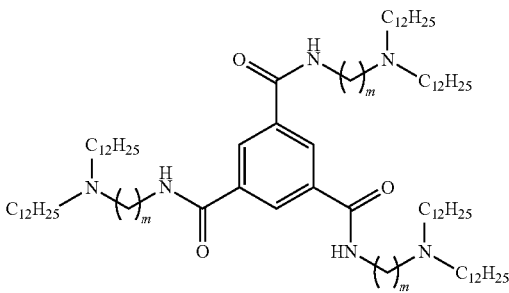

and salts thereof, wherein m=3.

10. A nanoparticle comprising:
a compound of Formula I;

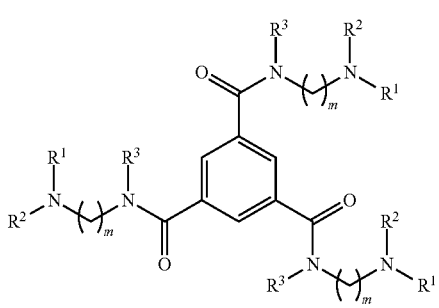

Formula I and salts thereof; wherein
each $R^1$ is independently substituted or unsubstituted alkyl;
each $R^2$ is independently substituted or unsubstituted alkyl;
each $R^3$ is independently hydrogen or substituted or unsubstituted alkyl; and
each m is independently 1, 2, 3, 4, 5, 6, 7, or 8;
a non-cationic lipid;
a polyethylene glycol-lipid; and
a sterol.

11. The nanoparticle of claim 10, wherein the compound of Formula I is:

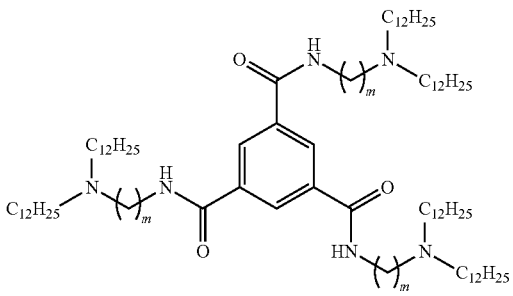

and salts thereof, wherein m=3.

12. The nanoparticle of claim 10, wherein the phosphatidylethanolamine lipid is selected from 1,2-dioleoyl-sn-glycero-3-phosphoethanolamine (DOPE), 1-palmitoyl-2-oleoyl-sn-glycero-3-phosphoethanolamine (POPE), 1,2-di stearoyl-sn-glycero-3-phosphocholine (DSPC), 1-stearoyl-2-oleoyl-sn-glycero-3-phosphoethanolamine (SOPE), or combinations thereof.

13. The nanoparticle of claim 12, wherein the phosphatidylethanolamine lipid is 1,2-dioleoyl-sn-glycero-3-phosphoethanolamine (DOPE).

14. The nanoparticle of claim 10, wherein the polyethylene glycol-lipid is selected from 1,2-dimyristoyl-sn-glycerol, methoxypolyethylene glycol (DMG-PEG), DLPE-PEGs, DMPE-PEGs, DPPC-PEGs, and DSPE-PEGs.

15. The nanoparticle of claim 14, wherein the polyethylene glycol-lipid is 1,2-dimyristoyl-sn-glycerol, methoxypolyethylene glycol (DMG-PEG).

16. The nanoparticle of claim 10, wherein the sterol is selected from cholesterol, campesterol, ergosterol, or sitosterol.

17. The nanoparticle of claim 16, wherein the sterol is cholesterol.

18. A method for the delivery of an agent into a cell comprising;
introducing into the cell a composition comprising;
a nanoparticle comprising;
a compound of Formula I;

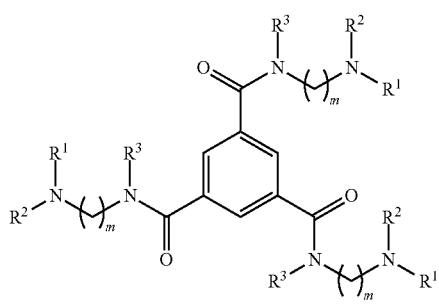

Formula I and salts thereof; wherein
each $R^1$ is independently substituted or unsubstituted alkyl;
each $R^2$ is independently substituted or unsubstituted alkyl;
each $R^3$ is independently hydrogen or substituted or unsubstituted alkyl; and
each m is independently 1, 2, 3, 4, 5, 6, 7, or 8;
a non-cationic lipid;
a polyethylene glycol-lipid;
a sterol; and
an agent.

19. The method of claim 18, wherein the agent is a polynucleotide.

20. A compound of Formula I:

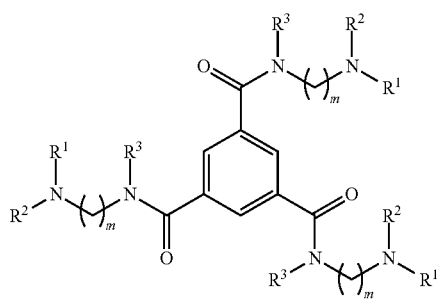

Formula I and salts thereof; wherein
each $R^1$ is independently substituted or unsubstituted alkyl;
each $R^2$ is independently substituted or unsubstituted alkyl;
each $R^3$ is independently hydrogen or substituted or unsubstituted alkyl; and
each m is independently 1, 2, 3, 4, 5, 6, 7, or 8;
wherein at least one $R^1$ is $C_{12}H_{25}$.

21. The compound of claim 20, wherein at least one $R^2$ is $C_{12}H_{25}$.

* * * * *